US008022098B2

(12) United States Patent
Chou et al.

(10) Patent No.: US 8,022,098 B2
(45) Date of Patent: *Sep. 20, 2011

(54) DEUTERATED AMINOCYCLOHEXYL ETHER COMPOUNDS AND PROCESSES FOR PREPARING SAME

(75) Inventors: Doug Ta Hung Chou, Vancouver (CA); Bertrand M. C. Plouvier, Vancouver (CA); Peter Pang, Richmond (CA); James Gee Ken Yee, Vancouver (CA); Jeffery Jerome Wheeler, Surrey (CA); Aregahegn S. Yifru, Somerville, MA (US); Allen W. Davidoff, Calgary (CA)

(73) Assignee: Cardiome Pharma Corp., Vancouver, BC (CA)

( * ) Notice: Subject to any disclaimer, the term of this patent is extended or adjusted under 35 U.S.C. 154(b) by 0 days.

This patent is subject to a terminal disclaimer.

(21) Appl. No.: 12/713,605

(22) Filed: Feb. 26, 2010

(65) Prior Publication Data

US 2010/0152276 A1     Jun. 17, 2010

Related U.S. Application Data

(60) Division of application No. 11/581,225, filed on Oct. 13, 2006, now Pat. No. 7,705,036, which is a continuation-in-part of application No. 11/455,280, filed on Jun. 15, 2006, now Pat. No. 7,754,897, said application No. 11/581,225 is a continuation-in-part of application No. PCT/US2006/023668, filed on Jun. 15, 2006, said application No. 11/581,225 is a continuation-in-part of application No. PCT/US2005/011124, filed on Mar. 31, 2005.

(60) Provisional application No. 60/748,248, filed on Dec. 7, 2005, provisional application No. 60/690,989, filed on Jun. 15, 2005, provisional application No. 60/559,405, filed on Apr. 1, 2004, provisional application No. 60/586,992, filed on Jul. 8, 2004.

(51) Int. Cl.
*A61K 31/40* (2006.01)
*C07D 207/00* (2006.01)

(52) U.S. Cl. ........................................ 514/424; 548/541

(58) Field of Classification Search .................. 514/424; 548/541
See application file for complete search history.

(56) References Cited

U.S. PATENT DOCUMENTS

| | | | | |
|---|---|---|---|---|
| 4,684,728 A | 8/1987 | Möhring et al. | ............. | 544/182 |
| 5,032,687 A | 7/1991 | Diehl et al. | ............. | 564/1 |
| 5,215,919 A | 6/1993 | Miya et al. | ............. | 435/280 |
| 5,728,873 A | 3/1998 | Kleemiss et al. | ............. | 564/1 |
| 5,846,514 A | 12/1998 | Foster et al. | ............. | 424/1.81 |
| 6,503,921 B2 | 1/2003 | Naicker et al. | ............. | 514/291 |
| 6,613,739 B1 | 9/2003 | Naicker et al. | ............. | 514/11 |
| 6,617,475 B2 | 9/2003 | Studer et al. | ............. | 568/648 |
| 6,939,878 B2 | 9/2005 | Naicker et al. | ............. | 514/291 |
| 7,053,087 B1 | 5/2006 | Beatch et al. | ............. | 514/237.8 |
| 7,056,942 B2 | 6/2006 | Hildesheim et al. | ............. | 514/411 |
| 7,057,053 B2 | 6/2006 | Beatch et al. | ............. | 548/541 |
| 7,259,184 B2 | 8/2007 | Beatch et al. | ............. | 514/424 |
| 7,345,087 B2 * | 3/2008 | Beatch et al. | ............. | 514/424 |
| 7,786,119 B2 | 8/2010 | Cheu et al. | ............. | 514/252.03 |
| 2003/0073617 A1 | 4/2003 | Li et al. | ............. | 514/2 |
| 2003/0130170 A1 | 7/2003 | Li et al. | ............. | 514/2 |
| 2003/0186400 A1 | 10/2003 | Asako et al. | ............. | 435/146 |
| 2004/0082043 A1 | 4/2004 | Yadav et al. | ............. | 435/148 |
| 2006/0094880 A9 | 5/2006 | Barrett et al. | ............. | 546/236 |
| 2007/0015924 A1 | 1/2007 | Jung et al. | ............. | 548/541 |
| 2007/0088075 A1 | 4/2007 | Chou et al. | ............. | 514/424 |
| 2009/0069404 A1 | 3/2009 | Czarnik | ............. | 514/424 |
| 2009/0088464 A1 | 4/2009 | Choi et al. | ............. | 514/424 |
| 2009/0105256 A1 | 4/2009 | Choi et al. | ............. | 514/237.2 |
| 2010/0152464 A1 | 6/2010 | Plouvier et al. | ............. | 548/544 |
| 2010/0217014 A1 | 8/2010 | Jung et al. | ............. | 548/544 |
| 2010/0273724 A1 | 10/2010 | Cheu et al. | ............. | 514/21.7 |

FOREIGN PATENT DOCUMENTS

| | | |
|---|---|---|
| CA | 710830 A | 6/1965 |
| DE | 27 53 556 A1 | 6/1979 |
| EP | 0 014 263 B1 | 8/1980 |
| EP | 0 317 780 B1 | 5/1989 |
| WO | WO 96/23894 A1 | 8/1996 |
| WO | WO 97/33552 A1 | 9/1997 |
| WO | WO 99/50225 A1 | 10/1999 |
| WO | WO 00/23023 A1 | 4/2000 |
| WO | WO 01/96335 A1 | 12/2001 |
| WO | WO 2004/014973 A2 | 2/2004 |
| WO | WO 2004/099137 | * 11/2004 |
| WO | WO 2004/099137 A1 | 11/2004 |
| WO | WO 2005/016242 A2 | 2/2005 |
| WO | WO 2005/094897 A2 | 10/2005 |
| WO | WO 2005/097087 A2 | 10/2005 |
| WO | WO 2005/113011 A2 | 12/2005 |
| WO | WO 2006/088525 A1 | 8/2006 |
| WO | WO 2006/138673 A2 | 12/2006 |

OTHER PUBLICATIONS

Adam et al., "Spectral and Chemical Properties of Dimethyldioxirane as Determined by Experiment and ab Initio Calculations," *J. Org. Chem.* 52(13): 2800-2803, 1987.

Alimardanov et al., "Use of DOE for Rapid Development of a Red-Al Reduction Process for the Synthesis of 3,4-Isopropylidenedioxypyrrolidine Hydrotosylate," *Organic Process Research & Development* 8(6): 834-837, 2004.

Anderson et al., "Sulfonation with Inversion by Mitsunobu Reaction: An Improvement on the Original Conditions," *J. Org Chem.* 61(22): 7955-7958, 1996.

Asunskis and Shechter, "Reactions of Conjugated Nitro Olefins with Phosphoranes and with Dimethylsulfoxonium Methylide to Give Ylides and Nitrocyclopropanes, Respectively," *J. Org. Chem.*33(3): 1164-1168, 1968.

Augy-Dorey et al., "Synthesis of Carbocyclic Analogues of Lipid X," *Tetrahedron* 49(36): 7997-8006, 1993.

Bodenan et al., "Acid-Catalyzed Ring Opening of 2-Substituted Aziridines with Alcohols," *Synthesis*: 288-292, Mar. 1992.

(Continued)

*Primary Examiner* — Joseph Kosack
(74) *Attorney, Agent, or Firm* — Seed IP Law Group PLLC

(57) ABSTRACT

This invention is directed to deuterated aminocyclohexyl ether compounds and processes for preparing same and methods of using same.

10 Claims, No Drawings

OTHER PUBLICATIONS

Bogatskii et al., "Effect of Polymethylene- and Polyhydroxyethylene-bis-(2-Amino-1,3-Diazepinium) Iodides on Cell and Model Membranes," *Byulleten' Éksperimental'noi Biologii i Meditsiny* 94(8): 52-54, Aug. 1982 [English translation included from the Department of Chemistry of Macrocyclic Complexones, Physicochemical Institute, Academy of Sciences of the Ukrainian SSR, Odessa, pp. 1071-1074.].

Brown and Krishnamurthy, "Forty Years of Hydride Reductions," *Tetrahedron* 35(64): 567-607, 1979.

Brown et al., "The Direct and Enantioselective Organocatalytic α-Oxidation of Aldehydes," *J. Am. Chem. Soc.* 125(36): 10808-10809, 2003.

Bryce and Gardiner, "Stereospecific Synthesis of the Cyclopenta[e]phenanthridine Ring System: Tetracyclic and Pentacyclic Analogues of *Cephalotaxus* Alkaloids," *Tetradedron* 44(2): 599-612, 1988.

Cassidei et al., "Oxygen-17 and Carbon-13 Identification of the Dimethyldioxirane Intermediate Arising in the Reaction of Potassium Caroate with Acetone," *J. Org. Chem.* 52(4): 699-700, 1987.

Chelucci et al., "Synthesis of 1-Substituted 2-[(2S)-2-Pyrrolidinyl]pyridine from L-Proline," *Synthesis*: 1121-1122, Dec. 1990.

Chiu et al., "Molecular dynamics computations and solid state nuclear magnetic resonance of the gramicidin cation channel," *Biophys. J.* 60: 974-978, Oct. 1991.

Christoffers et al., "Synthesis, resolution, and absolute configuration of *trans*-1-amino-2-dimethylaminocyclohexane," *Tetrahedron* 57: 1765-1769, 2001.

Curci et al., "Selective Oxidation of *O*-Isopropylidene Derivatives of Diols to 2-Hydroxy Ketones Employing Dioxiranes," *Tetrahedron Letters* 37(1): 115-118, 1996.

Curtis and Walker, "Quantification of arrhythmias using scoring systems: an examination of seven scores in an in vivo model of regional myocardial ischaemia," *Cardiovascular Research* 22: 656-665, 1988.

D'Accolti et al., "Selective Oxidation of Optically Active *sec,sec*-1,2-Diols by Dioxiranes. A Practical Method for the Synthesis of Homochiral α-Hydroxy Ketones in High Optical Purity," *J. Org. Chem.* 58(14): 3600-3601, 1993.

Daverio and Zanda, "Enantioselective reductions by chirally modified alumino- and borohydrides," *Tetradron: Asymmetry* 12: 2225-2259, 2001.

Engman and Cava, "BIS(p-Methoxyphenyl)telluroxide, a Novel Organotellurium Aldol Catalyst," *Tetrahedron Letters* 22(52): 5251-5252, 1981.

Fráter et al., "Regioselective Synthesis of (±)-Gabaculine Hydrochloride," *Tetrahedron Letters* 25(3): 281-284, 1984.

Godchot and Mousseron, "Sur le dédoublement du 2-aminocyclohexanol en ses antipodes optiques," *Bull. Soc. Chim. Fr.* 51: 1277-1282, 1932.

Greenwald, "PEG drugs: an overview," *Journal of Controlled Release* 74: 159-171, 2001.

Hamon and Tuck, "Asymmetric Synthesis of (S)-1-Methyl-2-cylohexen-1-ol, a Constituent of the Aggregation Pheromone of *Dendroctonus pseudotsugae*," *Tetrahedron* 56: 4829-4835, 2000.

Hayashi et al., "Asymmetric Ring Opening Reactions of Symmetrical *N*-Acylaziridines with Thiols Catalyzed by Chiral Dialkyl Tartrate—Diethylzinc Complexes," *Tetrahedron* 52(23): 7817-7832, 1996.

Henrot et al., "Aminoacids as Chiral Synthons: Preparation of Enantiomerically Pure (R) and (S) Malic Acids and Its Application to the Synthesis of 3-Hydroxy 4-Butanolide," *Synthetic Communications* 16(2): 183-190, 1986.

Higuchi and Shiobara, "Quantitative Determination of Nifedipine in Human Plasma by Selected Ion Monitoring," *Biomedical Mass Spectrometry* 5(3): 220-223, 1978.

Howard and Walker, "Electrical Stimulation Studies with Quinacainol, a Putative 1C Agent, in the Anaesthetised Rat," *Proc. West. Pharmacol. Soc.* 33: 123-127, 1990.

Iida et al., "Synthesis of $^{13}$C-Labelled Compounds having a Urea Unit, and Observation of $^{13}$C-Isotope Effect in Their Infrared Spectra," *J. Labelled Cpd. Radiopharm.* XXXIX(1): 69-77, 1997.

Jacobsen, "Asymmetric Catalysis of Epoxide Ring-Opening Reactions," *Acc. Chem. Res.* 33(6): 421-431, 2000.

Johansen et al., "Synthesis of carbon-14 and stable isotope labelled NN414: a potent potassium channel opener," *J. Labelled Cpd. Radiopharm.* 47: 127-138, 2004.

Joshi et al., "Enantioselective Ring Cleavage of *meso*-Epoxides with B-Halodiisopinocampheylboranes," *J. Am. Chem. Soc.* 110: 6246-6248, 1988.

Kahl et al., "Radioimmunoassay for the Calcium Release Channel Agonist Ryanodine," *Analytical Biochemistry* 218: 55-62, 1994.

Kepler et al., "Synthesis of 5,5-Diphenylhydantoin-2,4,5-$^{13}C_3$," *Journal of Labelled Compounds* 10(4): 683-687, Oct.-Dec. 1974.

Kinugasa et al., "Desymmetrization of *meso*-1,2-Diols via Chiral Lewis Acid-Mediated Ring-Cleavage of 1,3-Dioxolane Derivatives," *J. Am. Chem. Soc.* 119(38): 9067-9068, 1997.

Kodukulla et al., "Synthesis, Chemical Transformation and Antimicrobial Activity of a Novel Class of Nitroolefins: 1,3-Diaryl-2-nitroprop-1-enes," *Synthetic Communications* 24(6): 819-832, 1994.

Kubo et al., "A Facile Synthesis of 1,2,3,4-Tetrahydroisoquinolines Through Cyclization of *O-N*-Acetals," *Synthesis*: 824-827, Sep. 1987.

Liu and Yao, "One-pot synthesis of *trans*-β-alkylstyrenes," *Tetrahedron Letters* 42: 6147-6150, 2001.

Luurtsema et al., "Synthesis and PET-Studies of (R)- and (S)-[$^{11}$C]Verapamil for Measuring PGP Function in MDR1A(+/+)/B(+/+) and MDR1A(-/-)/B(-/-) Mice," *J. Labelled Cpd. Radiopharm.* 44(Suppl. I): S313-S315, 2001.

Maestro et al., "Enzymatic resolution of (±)-*trans*-2-aminocyclohexanol and (±)-*trans*-2-aminocyclopentanol," *Tetrahedron: Asymmetry* 8(18): 3153-3159, 1997.

Martichonok and Whitesides, "Stereoselective α-Sialylation with Sialyl Xanthate and Phenylsulfenyl Triflate as a Promotor," *J. Org. Chem.* 61(5): 1702-1706, 1996.

Martinelli et al., "Selective monosulfonylation of internal 1,2-diols catalyzed by di-*n*-butyltin oxide," *Tetrahedron Letters* 41: 3773-3776, 2000.

Martínez et al., "Highly Enantioselective Ring Opening of Epoxides Catalyzed by (salen)Cr(III) Complexes," *J. Am. Chem. Soc.* 117(21): 5897-5898, 1995.

Matsumoto et al., "Diastereoselective Synthesis of a Key Intermediate for the Preparation of Tricyclic β-Lactam Antibiotics," *Tetrahedron Letters* 40: 5043-5046, 1999.

Matsunaga et al., "Catalytic Enantioselective *meso* -Epoxide Ring Opening Reaction with Phenolic Oxygen Nucleophile Promoted by Gallium Heterobimetallic Multifunctional Complexes," *J. Am. Chem. Soc.* 122(10): 2252-2260, 2000.

McCleland et al., "Mechanistic Studies of the Zirconium—Triisopropanolamine-Catalyzed Enantioselective Addition of Azide to Cyclohexene Oxide," *J. Org. Chem.* 63(19): 6656-6666, 1998.

Mello et al., "Enzymic Regioselectivity in the Hydroxylation of Cholesterol Catalyzed by a Membrane-Spanning Metalloporphyrin," *J. Org. Chem.* 53(16): 3891-3893, 1988.

Mello et al., "Oxidations by Methyl(trifluoromethyl)dioxirane. 2. Oxyfunctionalization of Saturated Hydrocarbons," *J. Am. Chem. Soc.* 111(17): 6749-6757, 1989.

Momiyama and Yamamoto, "Catalytic Enantioselective Synthesis of α-Aminooxy and α-Hydroxy Ketone Using Nitrosobenzene," *J. Am. Chem. Soc.* 125(20): 6038-6039, 2003.

Mottet et al., "A Simple and Efficient Preparation of Propargylic β-Keto Esters through Transesterification," *J. Org. Chem.* 64(4): 1380-1382, 1999.

Moustafa et al., "Comparative Study on the para-Metabolic Oxidation of Phenytoin and Decadeuteriophenytoin," *Arzneim.-Forsch/Drug Res.* 40(II, 10): 1076-1078, 1990.

Mowry and Butler, "Fumaronitrile," *Organic Syntheses, Coll.* 4: 486, 1963, 3 pages.

Murray and Jeyaraman, "Dioxiranes: Synthesis and Reactions of Methyldioxiranes," *J. Org. Chem.* 50(16) 2847-2853, 1985.

Nachtsheim and Frahm, "Die asymmetrische Synthese von cis-1R,2R- und cis-1S,2S-2-Arylcyclohexanaminen," *Arch. Pharm. (Weinheim)* 322(4): 187-197, Apr. 1989.

Nagai, "Optical Rotatory Dispersion of Nitrobenzene Derivatives. VII. Application of Modified Curtius Rearrangement for Determining the Free Carboxylic Position in Some Partial Esters of 3-Nitrophthalic and 4-Nitrohemimellitic Acid," *Chem. Pharm. Bull.* 23(8): 1841-1844, 1975.

Nagel and Nedden, "Preparative and Structural Chemistry of Chiral 3-(Diphenylphosphanyl)-pyrrolidines and Their Palladium(II) Complexes," *Chem. Ber./Recueil* 130: 385-397, 1997.

Nakamura et al., "Recent developments in asymmetric reduction of ketones with biocatalysts," *Tetrahedron: Asymmetry* 14(60): 2659-2681, 2003.

Nakane et al., "7-Oxabicyclo[2.2.1]heptyl Carboxylic Acids as Thromboxane $A_2$ Antagonists: Aza ω-Chain Analogues," *J. Med. Chem.* 33(9) 2465-2476, 1990.

Naylor et al., "4-[(Alkylylamino)methyl]furo[3,2-c]pyridines: A New Series of Selective κ-Receptor Agonists," *Journal of Medicinal Chemistry* 37(14): 2138-2144, 1994.

Ohkuma et al., "Stereoselective Hydogenation of Simple Ketones Catalyzed by Ruthenium(II) Complexes," *Journal of Organic Chemistry* 61(15): 4872-4873, 1996.

Ohtaka and Kajiwara, "Synthesis of [$^{13}C_2$]nifedipine," *J. Labelled Cpd. Radiopharm.* 46: 1177-1179, 2003.

Pallavicini et al., "Resolution of 5-hydroxymethyl-2-oxazolidinone by preferential crystallization and investigations on the nature of the racemates of some 2-oxazolidinone derivatives," *Tetrahedron: Asymmetry* 15: 1659-1665, 2004.

Paquette et al., "Systematic Analysis of the Intramolecular Competition Associated with the Ring Closing Metathesis of Ene-Diene Systems of Differing Chain Length with a Pair of Ruthenium Catalysts," *Helvetica Chimica Acta* 85: 3033-3051, 2002.

Pasumansky and Singaram, "Recent Advances in the Chemistry of Lithium Aminoborohydrides," *AldrichimicaActa* 38(2): 61-65, 2005.

Raiford and Fox, "Condensation of Vanillin Substitution Products with Nitromethane," *J. Org. Chem.* 9: 170-174, 1944.

Rampe et al., "Deuterated analogs of verapamil and nifedipine. Synthesis and biological activity," *Eur. J. Med. Chem.* 28: 259-263, 1993.

Rao et al., "Cycloaddition of citral dienamines to β-nitrostyrenes: A stereochemical consideration," *Indian Journal of Chemistry* 29B: 207-214, Mar. 1990.

Schaus et al., "Practical Synthesis of Enantiopure Cyclic 1,2-Amino Alcohols via Catalytic Asymmetric Ring Opening of Meso Epoxides," *J. Org. Chem.* 62(12): 4197-4199, 1997.

Schlichter and Frahm, "Asymmetric Reductive Amination of Cycloalkanones, XIII: Enantioselective Amidoamination: A New Regiospecific Strategy for the Synthesis of Chiral Cyclohexane-1,2-diamino-Derivatives," *Arch. Pharm. (Weinheim)* 326: 429-436, 1993.

Srebnik et al., "Chiral Synthesis via Organoboranes 23. Enantioselective Ring Opening of *meso*-Epoxides with β-Halodiisopinocampheylboranes. The First General Synthesis of Optically Active 1,2-Halohydrins," *Israel Journal of Chemistry* 29: 229-237, 1989.

Tasker et al., "Potent and Selective Non-Benzodioxole-Containing Endothelin-A Receptor Antagonists," *J. Med. Chem* 40(3): 322-330, 1997.

Toshima and Tatsuta, "Recent Progress in *O*-Glycosylation Methods and Its Application to Natural Products Synthesis," *Chem. Rev.* 93(4): 1503-1531, 1993.

Tsuda et al., "A stereocontrolled construction of 2-azido-2-deoxy-1,2-*trans*-β-glycosidic linkages utilizing 2-azido-2-deoxyglycopyranosyl diphenyl phosphates," *Tetrahedron Letters* 44: 6453-6457, 2003.

Tuck et al., "A Simple Procedure for the Deuteriation of Phenols," *J. Labelled Cpd. Radiopharm.* 43: 817-823, 2000.

Urban et al., "Process Research and Large-Scale Synthesis of a Novel 5,6-Dihydro-(9H)-pyrazolo[3,4-c]-1,2,4-triazolo[4,3-α]pyridine PDE-IV Inhibitor," *Organic Process Research & Development* 5(6): 575-580, 2001.

Ursini et al., "Enzymatic Method of Preparation of Optically Active *trans*-2-Amino Cyclohexanol Derivatives," *Synthetic Communications* 29(8): 1369-1377, 1999.

Varma et al., "Microwave-Assisted Henry Reaction: Solventless Synthesis of Conjugated Nitroalkenes," *Tetrahedron Letters* 38(29): 5131-5134, 1997.

Ward, "Chiral Separations," *Anal. Chem.* 74(12): 2863-2872, Jun. 15, 2002.

Wimalasena and May, "Mechanistic Studies on Dopamine β-Monooxygenase Catalysis: N-Dealkylation and Mechanism-Based Inhibition by Benzylic-Nitrogen-Containing Compounds. Evidence for a Single-Electron-Transfer Mechanism," *J. Am. Chem. Soc.* 109(13): 4036-4046, 1987.

Yadav et al., "Efficient Enantioselective Reduction of Ketones with *Daucus carota* Root," *J. Org. Chem.* 67(11): 3900-3903, 2002.

\* cited by examiner

DEUTERATED AMINOCYCLOHEXYL ETHER COMPOUNDS AND PROCESSES FOR PREPARING SAME

CROSS REFERENCE TO RELATED APPLICATIONS

This application is a division of U.S. patent application Ser. No. 11/581,225, filed Oct. 13, 2006 (now allowed); which is a continuation-in-part of U.S. patent application Ser. No. 11/455,280, filed Jun. 15, 2006 (now allowed), which claims priority to U.S. Provisional Patent Application No. 60/748,248, filed Dec. 7, 2005 and to U.S. Provisional Patent Application No. 60/690,989, filed Jun. 15, 2005, wherein each of these applications is incorporated by reference herein in its entirety.

U.S. patent application Ser. No. 11/581,225, filed Oct. 13, 2006 (now allowed) is also a continuation-in-part of PCT Patent Application No. PCT/US06/23668, filed Jun. 15, 2006 (now expired), which claims priority to U.S. Provisional Patent Application No. 60/690,989, filed Jun. 15, 2005, and to U.S. Provisional Patent Application No. 60/748,248, filed Dec. 7, 2005, wherein each of these applications is incorporated by reference herein in its entirety.

U.S. patent application Ser. No. 11/581,225, filed Oct. 13, 2006 (now allowed) is also a continuation-in-part of PCT Patent Application No. PCT/US05/11124, filed Mar. 31, 2005 (now expired), which claims priority to U.S. Provisional Patent Application No. 60/559,405, filed Apr. 1, 2004, and to U.S. Provisional Patent Application No. 60/586,992, filed Jul. 8, 2004, wherein each of these applications is incorporated by reference herein in its entirety.

U.S. patent application Ser. No. 11/581,225, filed Oct. 13, 2006 (now allowed) also claims priority, under 35 U.S.C. 119(e), to U.S. Provisional Patent Application No. 60/748,248, filed Dec. 7, 2005, wherein the application is incorporated by reference herein in its entirety.

FIELD OF INVENTION

The present invention is generally directed towards deuterated aminocyclohexyl ether compounds and methods for their preparation. In particular, this invention is directed to deuterated-trans-(1R,2R)-aminocyclohexyl ether compounds, deuterated-trans-(1S,2S)-aminocyclohexyl ether compounds, deuterated cis-(1R,2S)-aminocyclohexyl ether compounds, and deuterated cis-(1S,2R)-aminocyclohexyl ether compounds, as well as various intermediates, substrates and stereoisomers and methods for their preparation. The deuterated compounds of the invention are useful as standards in determining the biological efficacy of the corresponding non-deuterated compounds. The deuterated compounds of the invention are also useful in treating arrhythmia in humans.

BACKGROUND OF THE INVENTION

Deuterated drugs are widely used in studies of metabolism of drugs and toxic substances in humans and other animals. The deuterated forms of drugs often have different actions than the protonated forms. Some deuterated drugs show different transport processes. Most are more resistant to metabolic changes, especially those changes mediated by cytochrome P450 systems. Deuteration may also change the pathway of drug metabolism (metabolic switching). Changed metabolism may lead to increased duration of action and lower toxicity. It may also lead to lower activity, if the drug is normally changed to the active form in vivo. Deuteration can also lower the genotoxicity of the anticancer drug tamoxifen and other compounds. Deuteration increases effectiveness of long-chain fatty acids and fluoro-D-phenylalanine by preventing their breakdown by target microorganisms.

Deuterium (D) is a nonradioactive isotope which contains one additional neutron than the normally abundant isotope of hydrogen which does not contain any neutrons. Deuterium behaves similarly to ordinary hydrogen, but it can be distinguished from ordinary hydrogen by its mass using mass spectrometry or infrared spectrometry. Consequently, deuterated compounds have been long used in pharmaceutical research to investigate the in vivo metabolic fate of the compounds by evaluation of the mechanism of action and metabolic-pathway of the non deuterated parent compound. Such metabolic studies are important in the design of safe, effective therapeutic drugs.

Incorporation of deuterium for a hydrogen atom in a drug can give rise to an isotope effect that can alter the pharmacokinetics of the drug. This effect is usually insignificant if the label is placed in a molecule at the metabolically inert position of the molecule. For instance, deuteration, as exemplified by deuterated Rapamycin (see U.S. Pat. No. 6,503,921), Cyclosporine (see U.S. Pat. No. 6,613,739) or Nifedipine (see U.S. Pat. No. 5,846,514) has been reported to alter the pharmacokinetics of a drug. Forster et al. (Isotechnica, AB) have shown that deuteration can enhance duration of action.

Deuterium-labeling of a drug can alter its physico-chemical properties such as pKa and lipid solubility. These changes may influence the fate of the drug at different steps along its passage through the body. Absorption, distribution, metabolism or excretion can be changed. Absorption and distribution are processes that depend primarily on the molecular size and the lipophilicity of the substance.

Drug metabolism can give rise to large isotopic effect if the breaking of a chemical bond to a deuterium atom is the rate limiting step in the process. While some of the physical properties of a deuterium-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. In any reaction in which the breaking of this bond is the rate limiting step, the reaction will proceed slower for the molecule with the heavy isotope due to kinetic isotope effect. A reaction involving breaking a C-D bond can be up to 700 percent slower than a similar reaction involving breaking a C—H bond.

More caution has to be observed when using deuterium-labeled drugs. If the C-D bond is not involved in any of the steps leading to the metabolite, there may not be any effect to alter the behavior of the drug. If deuterium is placed at a site involved in the metabolism of a drug, an isotope effect will be observed only if breaking of the C-D bond is the rate limiting step. There are evidences to suggest that whenever cleavage of an aliphatic C—H bond occurs, usually by oxidation catalyzed by a mixed-function oxidase, replacement of the hydrogen by deuterium will lead to observable isotope effect. It is also important to understand that the incorporation of deuterium at the site of metabolism slows its rate to the point where another metabolite produced by attack at a carbon atom not substituted by deuterium becomes the major pathway by a process called "metabolic switching".

It is also observed that one of the most important metabolic pathways of compounds containing aromatic systems is hydroxylation leading to a phenolic group in the 3 or 4 position to carbon substituents. Although this pathway involves cleavage of the C—H bond, it is often not accompanied by an isotope effect, because the cleavage of this bond is mostly not involved in the rate-limiting step. The substitution of hydrogen by deuterium at the stereo center will induce a greater effect on the activity of the drug.

Clinically relevant questions with respect to deuterium-labeled drugs include the toxicity of the drug and its metabolite derivatives, the changes in distribution or elimination (enzyme induction), lipophilicity which will have an effect on absorption of the drug. Replacement of hydrogen by deuterium at the site involving the metabolic reaction will lead to increased toxicity of the drug. Replacement of hydrogen by deuterium at the aliphatic carbons will have an isotopic effect to a larger extent. Deuterium placed at an aromatic carbon atom, which will be the site of hydroxylation, may lead to an observable isotope effect, although this is less often the case than with aliphatic carbons. In few cases, such as in penicillin, the substitution on the aromatic ring will induce the restriction of rotation of the ring around the C—C bond leading to a favorable stereo-specific situation to enhance the activity of the drug.

Side-effects with acute deuterium dosing have been shown to be transitory with no demonstrated evidence of permanent deleterious action. The threshold of deuterium toxicity has been defined in animals and is far in excess of concentrations conceivably used in human studies. The possibility that deuterium may have additional beneficial pharmacological applications can therefore not be excluded.

PCT Published Patent Application, WO 2004/099137 discloses a class of aminocyclohexyl ether compounds as being useful in the treatment of arrhythmias. One class of compounds disclosed therein are particularly effective in the treatment and/or prevention of arrhythmia, particularly atrial fibrillation.

There exists, therefore, a need to prepare deuterated compounds which can be used, inter alia, as standards or tracer molecules in biological or bioanalytical assays in order to determine the biological effectiveness and metabolic pathway for a class of compounds disclosed in PCT Published Patent Application WO 99/50225.

SUMMARY OF THE INVENTION

In one aspect, this invention is directed to compounds of formula (I):

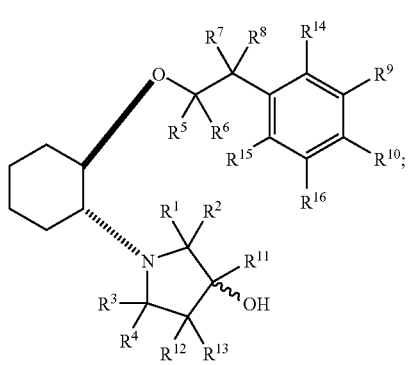

wherein:
$R^1, R^2, R^3, R^4, R^5, R^6, R^7, R^8, R^{11}, R^{12}, R^{13}, R^{14}, R^{15}$ and $R^{16}$ are each independently hydrogen or deuterium;

$R^9$ and $R^{10}$ are each independently hydroxy, methoxy or —OCD$_3$; and
at least one deuterium is present;
as an isolated stereoisomer or as a mixture of stereoisomers; or a pharmaceutically acceptable salt thereof.

In another aspect, this invention is directed to compounds of formula (I), as described above, wherein:
$R^1$ and $R^2$ are both hydrogen or are both deuterium;
$R^3$ and $R^4$ are both hydrogen or are both deuterium;
$R^5$ and $R^6$ are both hydrogen or are both deuterium;
$R^7$ and $R^8$ are both hydrogen or are both deuterium;
$R^9$ and $R^{10}$ are each independently hydroxy, methoxy or —OCD$_3$;
$R^{11}$ is hydrogen or deuterium;
$R^{12}$ and $R^{13}$ are both hydrogen or are both deuterium; and
$R^{14}, R^{15}$ and $R^{16}$ are each hydrogen;
wherein at least one of the following applies:
a) $R^1$ and $R^2$ are both deuterium;
b) $R^3$ and $R^4$ are both deuterium;
c) $R^5$ and $R^6$ are both deuterium;
d) $R^7$ and $R^8$ are both deuterium;
e) $R^9$ is —OCD$_3$;
f) $R^{10}$ is —OCD$_3$;
g) $R^{11}$ is deuterium; or
h) $R^{12}$ and $R^{13}$ are both deuterium;
as an isolated stereoisomer or as a mixture of stereoisomers; or a pharmaceutically acceptable salt thereof.

In another aspect, this invention is directed to pharmaceutical compositions comprising a pharmaceutically acceptable excipient and a compound of formula (I), as described above, as an isolated stereoisomer or as a mixture of stereoisomers, or a pharmaceutically acceptable salt thereof.

In another aspect, this invention is directed to methods of treating arrhythmia in a human, wherein the methods comprise administering to the human in need thereof a therapeutically effective amount of a compound of formula (I), as described above, as an isolated stereoisomer or as a mixture of stereoisomers, or a pharmaceutically acceptable salt thereof.

In another aspect, this invention is directed to methods of preparing compounds of formula (I), as described above, where $R^{14}, R^{15}$ and $R^{16}$ are each hydrogen, as an isolated stereoisomer or as a mixture of stereoisomers, or a pharmaceutically acceptable salt thereof.

In another aspect, this invention is directed to methods of determining the concentration of a compound in a biological matrix, wherein the method comprises contacting a compound of formula (I), as described above, where $R^{14}, R^{15}$ and $R^{16}$ are each hydrogen, as an isolated stereoisomer or as a mixture of stereoisomers, or a pharmaceutically acceptable salt thereof, with a biological matrix containing a compound of formula (I):

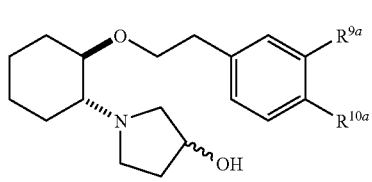

wherein each $R^{9a}$ and $R^{10a}$ are independently hydroxy or methoxy; as an isolated stereoisomer or as a mixture of stereoisomers, or a pharmaceutically acceptable salt thereof; and determining the concentration of the compound of formula (1) in the biological matrix.

In another aspect, this invention is directed to compounds of formula (II):

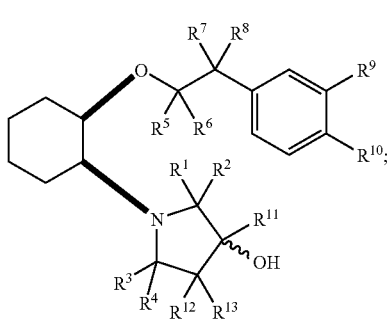

(II)

wherein:
R$^1$, R$^2$, R$^3$, R$^4$, R$^5$, R$^6$, R$^7$, R$^8$, R$^{11}$, R$^{12}$ and R$^{13}$ are each independently hydrogen on deuterium;
R$^9$ and R$^{10}$ are each independently hydroxy, methoxy or —OCD$_3$; and
at least one deuterium is present;
as an isolated stereoisomer or as a mixture of stereoisomers; or a pharmaceutically acceptable salt thereof.

In another aspect, this invention is directed to compounds of formula (II) described above, wherein:
R$^1$ and R$^2$ are both hydrogen or are both deuterium;
R$^3$ and R$^4$ are both hydrogen or are both deuterium;
R$^5$ and R$^6$ are both hydrogen or are both deuterium;
R$^7$ and R$^8$ are both hydrogen or are both deuterium;
R$^9$ and R$^{10}$ are each independently hydroxy, methoxy or —OCD$_3$;
R$^{11}$ is hydrogen or deuterium; and
R$^{12}$ and R$^{13}$ are both hydrogen or are both deuterium;
wherein at least one of the following applies:
  a) R$^1$ and R$^2$ are both deuterium;
  b) R$^3$ and R$^4$ are both deuterium;
  c) R$^5$ and R$^6$ are both deuterium;
  d) R$^7$ and R$^8$ are both deuterium;
  e) R$^9$ is —OCD$_3$;
  f) R$^{10}$ is —OCD$_3$;
  g) R$^{11}$ is deuterium; or
  h) R$^{12}$ and R$^{13}$ are both deuterium;
as an isolated stereoisomer or as a mixture of stereoisomers; or a pharmaceutically acceptable salt thereof.

In another aspect, this invention is directed to pharmaceutical compositions comprising a pharmaceutically acceptable excipient and a compound of formula (II), as described above, as an isolated stereoisomer or as a mixture of stereoisomers, or a pharmaceutically acceptable salt thereof.

In another aspect, this invention is directed to methods of treating arrhythmia in a human, wherein the methods comprise administering to the human in need thereof a therapeutically effective amount of a compound of formula (II), as described above, as an isolated stereoisomer or as a mixture of stereoisomers, or a pharmaceutically acceptable salt thereof.

In another aspect, this invention is directed to methods of preparing compounds of formula (II), as described above, as an isolated stereoisomer or as a mixture of stereoisomers, or a pharmaceutically acceptable salt thereof.

In another aspect, this invention is directed to methods of determining the concentration of a compound in a biological matrix, wherein the method comprises contacting a compound of formula (II), as described above, as an isolated stereoisomer or as a mixture of stereoisomers, or a pharmaceutically acceptable salt thereof, with a biological matrix containing a compound of formula (2):

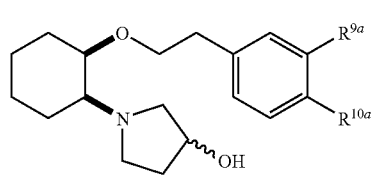

(2)

wherein each R$^{9a}$ and R$^{10a}$ are independently hydroxy or methoxy; as an isolated stereoisomer or as a mixture of stereoisomers, or a pharmaceutically acceptable salt thereof; and determining the concentration of the compound of formula (2) in the biological matrix.

These and other aspects of the invention will be apparent upon reference to the following detailed description. To this end, various references are set forth herein which describe in more detail certain background information, procedures, compounds and/or compositions, and are each hereby incorporated by reference in their entirety.

DETAILED DESCRIPTION OF THE INVENTION

An understanding of the present invention may be aided by reference to the following explanation of conventions used herein and definitions:

The compounds of formula (I) and the compounds of formula (II) have an ether oxygen atom at position 1 of a cyclohexane ring, and an amine nitrogen atom at position 2 of the cyclohexane ring, with other positions numbered in corresponding order as shown below in Structure (Aa) and Structure (Ab), respectively, below:

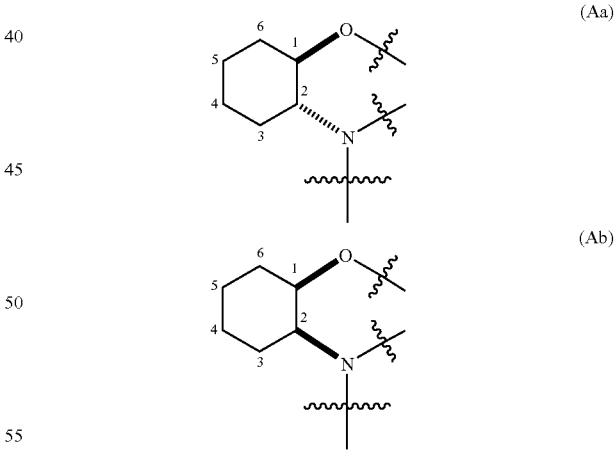

The bonds from the cyclohexane ring to the 1-oxygen and 2-nitrogen atoms in the Structure (Aa) above are disposed in the trans relationship. Therefore, the stereochemistry of the amine and ether substituents of the cyclohexane ring in Structure (Aa) is (1R,2R)-trans or (1S,2S)-trans. The bonds from the cyclohexane ring to the 1-oxygen and 2-nitrogen atoms in the Structure (Ab) above are disposed in the cis relationship. Therefore, the stereochemistry of the amine and ether substituents of the cyclohexane ring in Structure (Ab) is (1R,2S)-cis or (1R,2S)-cis.

Following the standard chemical literature description practice and as used in this specification, a solid full bond, as illustrated above in Structure (Aa) and a dashed full bond, as illustrated above in Structure (Aa), means that the substituents, in this case the amine and ether substituents, are in a trans-configuration with respect to the plane of the ring.

Following the standard chemical literature description practice and as used in this specification, a solid full bond, as illustrated above in Structure (Ab) and a solid full bond, as illustrated above in Structure (Ab), means that the substituents, in this case the amine and ether substituents, are in a cis-configuration with respect to the plane of the ring.

Following the standard chemical literature description practice and as used in this specification, a full wedge bond, as exemplified below in Structure (Ac), means that the substituent bonded to the ring by this bond, in this case the ether substituent, is above the ring plane as illustrated on the page in a two dimensional representation, and a dashed wedge bond, as exemplified below in Structure (Ac), means that the substituent bonded to the ring by this bond, in this case the amine substituent, is below the ring plane as shown on the page in a two dimensional representation. In contrast, two full wedge bonds, as exemplified below in Structure (Ad), means that both substituents bonded to the ring by these bonds, in this case both the ether and the amino substituent, are above the ring plane as illustrated on the page in a two dimensional representation:

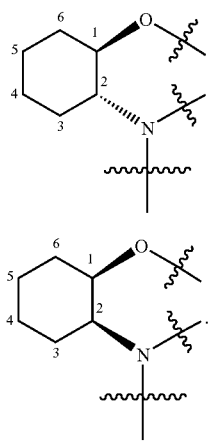

In a similar manner, as exemplified below in Structure (Ae), the ether substituent is below the ring plane and the amino substituent is above the ring plane, as shown on the page in a two dimensional representation. In contrast, as exemplified below in Structure (Af), both the ether and the amino substituent are below the ring plane as illustrated on the page in a two dimensional representation:

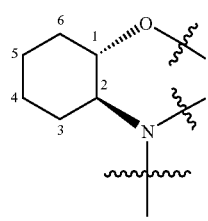

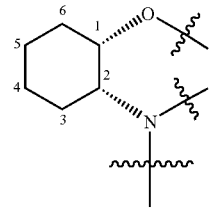

Following the standard chemical literature description practice and as used in this specification, a wavy bond, as illustrated below in the compound of formula (B), indicates that the substituent, in this case the —OR substituent, is either below the plane of the ring or above the plane of the ring:

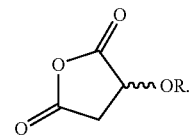

As indicated above, the compounds of the present invention contain at least two asymmetric carbon atoms and thus exist as enantiomers and diastereoisomers. For the present invention, the words diastereomer and diastereoisomer and related terms are equivalent and interchangeable. Unless otherwise indicated, the present invention includes all enantiomeric and diastereoisomeric forms of the aminocyclohexyl ether compounds of formula (I) and formula (II). Pure stereoisomers, mixtures of enantiomers and/or diastereoisomers, and mixtures of different compounds of the invention are included within the present invention. Thus, compounds of formula (I) and compounds of formula (II) may occur as racemates, diastereomeric mixtures and as individual diastereoisomers, or enantiomers, unless a specific stereoisomer enantiomer or diastereoisomer is identified, with all isomeric forms being included in the present invention. For the present invention, a racemate or diastereomeric mixture does not imply a 50:50 mixture of stereoisomers only. Other enantiomerically or diastereomerically enriched mixtures of varying ratios of stereoisomers are also contemplated. Unless otherwise noted, the phrase "stereoisomerically substantially pure" generally refers to those asymmetric carbon atoms that are described or illustrated in the structural formulae for that compound.

The definition of stereoisomeric purity (or optical purity or chiral purity) and related terminology and their methods of determination (e.g., Optical rotation, circular dichroism etc.) are well known in the art (see e.g., E. L. Eliel and S. H. Wilen, in Stereochemistry of Organic Compounds; John Wiley & Sons: New York, 1994; and references cited therein). The phrase "stereoisomerically substantially pure" generally refers to the enrichment of one of the stereoisomers (e.g., enantiomers or diastereoisomers) over the other stereoisomers in a sample, leading to chiral enrichment and increase in optical rotation activity of the sample. Enantiomer is one of a pair of molecular species that are mirror images of each other and not superimposable. They are "mirror-image" stereoisomers. Diastereoisomers generally refer to stereoisomers not related as mirror-images. Enantiomeric excess (ee) and diastereoisomeric excess (de) are terms generally used to refer the stereoisomeric purity (or optical purity or chiral purity) of a sample of the compound of interest. Their definition and methods of determination are well known in the art and can be found e.g., in E. L. Eliel and S. H. Wilen, in *Stereochemistry of Organic Compounds*; John Wiley & Sons: New York, 1994; and references cited therein. "Stereoselectively making" refers to preparing the compound having enantiomeric excess (ee) or diastereoisomeric excess (de).

For the present invention, enantiomeric excess (ee) or diastereoisomeric excess (de) in the range of about 50% to about 100% is contemplated. A preferred range of enantiomeric excess (ee) or diastereoisomeric excess (de) is about 60% to about 100%. Another preferred range of enantiomeric excess (ee) or diastereoisomeric excess (de) is about 70% to about 100%. A more preferred range of enantiomeric excess (ee) or diastereoisomeric excess (de) is about 80% to about 100%. Another more preferred range of enantiomeric excess (ee) or diastereoisomeric excess (de) is about 85% to about 100%. An even more preferred range of enantiomeric excess (ee) or diastereoisomeric excess (de) is about 90% to about 100%. Another even more preferred range of enantiomeric excess (ee) or diastereoisomeric excess (de) is about 95% to about 100%. It is understood that the phrase "about 50% to about 100%" includes but is not limited to all the possible percentage numbers and fractions of a number from 50% to 100%. Similarly, the phrase "about 60% to about 100%" includes but is not limited to all the possible percentage numbers and fractions of a number from 60% to 100%; the phrase "about 70% to about 100%" includes but is not limited to all the possible percentage numbers and fractions of a number from 70% to 100%; the phrase "about 80% to about 100%" includes but is not limited to all the possible percentage numbers and fractions of a number from 80% to 100%; the phrase "about 85% to about 100%" includes all but is not limited to the possible percentage numbers and fractions of a number from 85% to 100%; the phrase "about 90% to about 100%" includes but is not limited to all the possible percentage numbers and fractions of a number from 90% to 100%; the phrase "about 95% to about 100%" includes all but is not limited to the possible percentage numbers and fractions of a number from 95% to 100%.

As an example, and in no way limiting the generality of the above, a compound of formula (I):

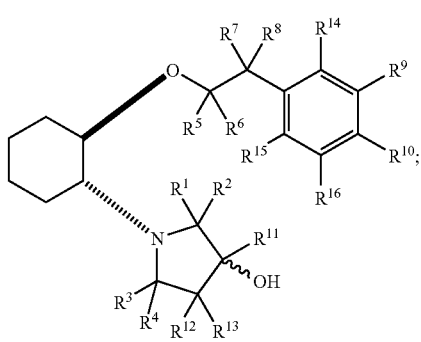

as described above in the Summary of the Invention, includes at least three chiral centers (the cyclohexyl carbon bonded to the oxygen at the 1 position, the cyclohexyl carbon bonded to the nitrogen at the 2 position, and the pyrrolidinyl carbon bonded to the hydroxyl at the 3 position of the pyrrolidinyl) and therefore has at least four separate stereoisomers, which are (1R,2R)-2-[(3R)-hydroxypyrrolidinyl]-1-(substituted phenethoxy)cyclohexane; (1R,2R)-2-[(3S)-hydroxypyrrolidinyl]-1-(substituted phenethoxy)cyclohexane; (1S,2S)-2-[(3R)-hydroxypyrrolidinyl]-1-(substituted phenethoxy)cyclohexane; and (1S,2S)-2-[(3S)-hydroxypyrrolidinyl]-1-(substituted phenethoxy)cyclohexane; and, unless the context make plain otherwise as used in this specification, for example, a compound of formula (I) refers to a composition that includes a component that is either one of the possible pure enantiomeric or diastereoisomeric forms of the indicated compound or is a mixture of any two or more of the pure enantiomeric or diastereoisomeric forms, where the mixture can include any number of the enantiomeric or diastereoisomeric forms in any ratio.

Similarly, a compound of formula (II):

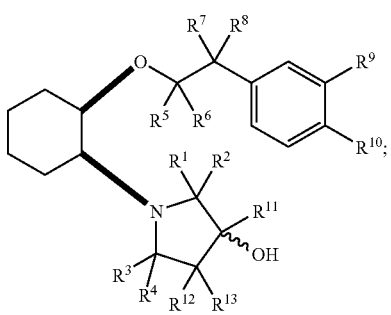

as described above in the Summary of the Invention, also includes at least three chiral centers and therefore has at least four separate stereoisomers, which are (1S,2R)-2-[(3R)-hydroxypyrrolidinyl]-1-(substituted phenethoxy)cyclohexane; (1S,2R)-2-[(3S)-hydroxypyrrolidinyl]-1-(substituted phenethoxy)cyclohexane; (1S,2R)-2-[(3R)-hydroxypyrrolidinyl]-1-(substituted phenethoxy)cyclohexane; and (1S,2R)-2-[(3S)-hydroxypyrrolidinyl]-1-(substituted phenethoxy)cyclohexane; and, unless the context make plain otherwise as used in this specification, for example, a compound of formula (II) refers to a composition that includes a component that is either one of the possible pure enantiomeric or diastereoisomeric forms of the indicated compound or is a mixture of any two or more of the pure enantiomeric or diastereoisomeric forms, where the mixture can include any number of the enantiomeric or diastereoisomeric forms in any ratio.

Certain chemical groups named herein are preceded by the shorthand notation "$C_x$-$C_y$," where x and y indicate the lower and upper, respectively, number of carbon atoms to be found in the indicated chemical group. For example; $C_1$-$C_8$acyl describes an acyl group, as defined below, having a total of 1 to 8 carbon atoms. Occasionally, certain chemical groups named herein are preceded by the shorthand notation "$C_z$," where z indicates the total number of carbons to be found in the indicated chemical group. The total number of carbons in the shorthand notation does not include carbons that may exist in substituents of the group described.

In accordance with the present invention and as used herein, the following terms are defined to have following meanings, unless explicitly stated otherwise: "Acid addition salts" generally refer to but are not limited to those salts which retain the biological effectiveness and properties of the free bases and which are not biologically or otherwise undesirable, formed with inorganic acids such as but not limited to hydrochloric acid, hydrobromic acid, sulfuric acid, nitric acid, phosphoric acid and the like, or acceptable Lewis acids, or organic acids such as but not limited to acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like, and include but not limited to those described in for example: "Handbook of Pharmaceutical Salts, Properties, Selection, and Use", P. Heinrich Stahl and Camille G. Wermuth (Eds.), Published by VHCA (Switzerland) and Wiley-VCH (FRG), 2002.

"Acyl" refers to branched or unbranched hydrocarbon fragments terminated by a carbonyl —(C=O)— group containing the specified number of carbon atoms. Examples include acetyl (Ac)[$CH_3C(=O)$—, a $C_2$acyl] and propionyl [$CH_3CH_2C(=O)$—, a $C_3$acyl].

"Biological matrix" refers to an environment that may or may not be isolated from a warm-blooded animal. Non-limiting examples of biological matrices are: urine, feces, blood, serum, plasma, saliva, perspiration, tissue fluid, cellular cytoplasm, hepatocytes, microsomes, S9 fractions, tissues, such as muscle tissue, hepatic tissue, cardiac tissue, renal tissue and other bodily environments and/or matrices of a warm-blooded animal, preferably a human. A biological matrix may be present in solution or in solid form or a mixture thereof and may be present in or as part of a living organism or may be isolated from a living organism such that it forms a sample therefrom.

"Pharmaceutically acceptable excipients" for therapeutic use are well known in the pharmaceutical art, and are described, for example, in *Remingtons Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. In addition, antioxidants and suspending agents may be used.

"Pharmaceutically acceptable salt" refers to salts of the compounds of the present invention derived from the combination of such compounds and a pharmaceutically acceptable organic or inorganic acid (acid addition salts) or a pharmaceutically acceptable organic or inorganic base (base addition salts) which retain the biological effectiveness and properties of the compounds of the present invention and which are not biologically or otherwise undesirable. Examples of pharmaceutically acceptable salts include, but are not limited to, those described in, for example, "Handbook of Pharmaceutical Salts, Properties, Selection, and Use", P. Heinrich Stahl and Camille G. Wermuth (Eds.), Published by VHCA (Switzerland) and Wiley-VCH (FRG), 2002. The compounds of the present invention may be used in either the free base or salt forms, with both forms being considered as being within the scope of the present invention.

The "therapeutically effective amount" of a compound of the present invention will depend on the route of administration, the type of warm-blooded animal being treated, and the physical characteristics of the specific warm-blooded animal under consideration. These factors and their relationship to determining this amount are well known to skilled practitioners in the medical arts. This amount and the method of administration can be tailored to achieve optimal efficacy but will depend on such factors as weight, diet, concurrent medication and other factors which those skilled in the medical arts will recognize.

Compositions described herein as comprising a compound of the present invention encompass compositions that may contain more than one compound of the present invention.

The chemical naming protocol and structure diagrams used herein are a modified form of the I.U.P.A.C. nomenclature system wherein the compounds of the invention are named herein as derivatives of the central core structure, i.e., the cyclohexane structure. Thus, a compound of formula (I) wherein $R^1$, $R^2$, $R^3$, $R^4$, $R^5$ and $R^6$ are each deuterium and $R^7$, $R^8$, $R^{11}$, $R^{12}$ and $R^{13}$ are each hydrogen and $R^9$ is methoxy and $R^{10}$ is —$OCD_3$, and $R^{14}$, $R^{15}$, and $R^{16}$ are each hydrogen, i.e., a compound of the following formula:

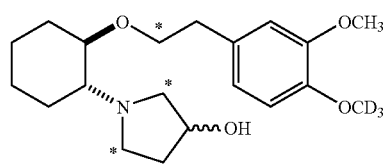

is named herein as (1R,2R/1S,2S)-2-[(3R/3S)-hydroxy-2,2,5,5-$d_4$-pyrrolidinyl]-1-(3-methoxy-4-$d_3$-methoxyphen-1,1-$d_2$-ethoxy)cyclohexane.

Utility of the Compounds of the Invention

Compounds of formula (I) and compounds of formula (II) may be used as standards to determine the concentration of the corresponding non-deuterated compounds in various biological matrices (such as plasma, serum, and urine).

The corresponding non-deuterated compounds are disclosed in PCT Published Patent Application, WO 2004/099137 and are useful in treating, inter alia, arrhythmia, particularly, atrial fibrillation and/or flutter. Of particular interest is the use of the compounds of the invention to determine the concentration of the following compounds of formula (1) and/or compounds of formula (2) in various biological matrices:

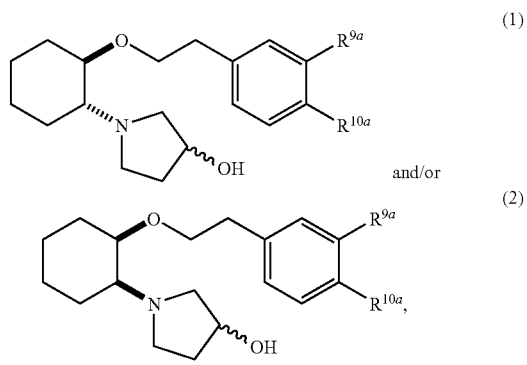

where each $R^{9a}$ and each $R^{10a}$ are independently hydroxy or methoxy, as isolated stereoisomers or as mixtures of stereoisomers; or pharmaceutically acceptable salts thereof. The stereochemistry at position 1 and 2 of the cyclohexyl group in compounds of formula (1) and formula (2) is depicted in the same manner as described herein for compounds of formula (I) and formula (II).

The use of the compounds of the invention as standards allows for the compensation of any instrumental or sample preparation error in the bioanalysis of the compounds of formula (1) and the compounds of formula (2) present in biological matrices. The compounds of the invention corresponding to the compounds of formula (1) and the compounds of formula (2), as set forth above, behave in the same manner as the compounds of formula (1) and compounds of formula (2) in such assays. However, the compounds of the invention can be differentiated from the compounds of formula (1) or the compounds of formula (2) in such assays through mass spectrometry due to the presence of one or more deuterium atoms thereon. Compounds of formula (I) and compounds of formula (II) may also be used as probes in assays for metabolic profiling, for example in cytochrome p450 enzyme assays, such as CYP2D6.

The compounds of the invention are also useful as pharmaceutical agents in the treatment of arrhythmia, particularly atrial fibrillation and/or flutter, in the same manner as described for the corresponding non-deuterated compounds disclosed in PCT Published Patent Application, WO 2004/099137.

Pharmaceutical Compositions of the Invention and Administration

For the purposes of administering a compound of the invention to a human to treat arrhythmia, the compounds of the invention, as isolated stereoisomers or as mixtures of stereoisomers; or pharmaceutically acceptable salts thereof, may be formulated as pharmaceutical compositions. Pharmaceutical compositions of the present invention comprise a compound of the invention, as an isolated stereoisomer or as a mixture of stereoisomers, or a pharmaceutically acceptable salt thereof, and a pharmaceutically acceptable excipient, carrier and/or diluent. The compound of the invention, as an isolated stereoisomer or as a mixture of stereoisomers, or a pharmaceutically acceptable salt thereof, is present in the composition in an amount sufficient to effect treatment of arrhythmia in a human, i.e., in a therapeutically effective amount.

Pharmaceutically acceptable excipients, carriers and/or diluents are familiar to those skilled in the art. For compositions formulated as liquid solutions, acceptable carriers and/or diluents include saline and sterile water, and may optionally include antioxidants, buffers, bacteriostats and other common additives. The pharmaceutical compositions of the invention can be prepared by combining a compound of the invention, as an isolated stereoisomer or as a mixture of stereoisomers, or a pharmaceutically acceptable salt thereof, with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. These compositions may also contain dispersing and surface active agents, binders, and lubricants. One skilled in this art may further formulate the compound of the invention, as an isolated stereoisomer or as a mixture of stereoisomers, or a pharmaceutically acceptable salt thereof, in an appropriate manner, and in accordance with accepted practices, such as those disclosed in *Remington's Pharmaceutical Sciences*, Gennaro, Ed., Mack Publishing Co., Easton, Pa. 1990.

Typical routes of administering the pharmaceutical compositions of the invention include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow a compound of the invention, as an isolated stereoisomer or as a mixture of stereoisomers, or a pharmaceutically acceptable salt thereof, contained therein to be bioavailable upon administration of the composition to a human.

The compounds of the invention, as isolated stereoisomers or as mixtures of stereoisomers, or pharmaceutically acceptable salts thereof, are administered in a therapeutically effective amount, which will vary depending upon a variety of factors including the activity of the specific compound employed; the metabolic stability and length of action of the compound; the age, body weight, general health, sex, and diet of the person to which the compound and/or composition of the invention is administered; the mode and time of administration; the rate of excretion; the drug combination; and the severity of the condition to be treated. Generally, a therapeutically effective daily dose is (for a 70 kg mammal) from about 0.001 mg/kg (i.e., 0.7 mg) to about 100 mg/kg (i.e., 7.0 gm); preferably a therapeutically effective dose is (for a 70 kg mammal) from about 0.01 mg/kg (i.e., 7 mg) to about 50 mg/kg (i.e., 3.5 gm); more preferably a therapeutically effective dose is (for a 70 kg mammal) from about 1 mg/kg (i.e., 70 mg) to about 25 mg/kg (i.e., 1.75 gm).

Compounds of the invention, as isolated stereoisomers or as mixtures of stereoisomers, or pharmaceutically acceptable salts thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention, as an isolated stereoisomer or as a mixture of stereoisomers, or a pharmaceutically acceptable salt thereof, and the other active agent can be administered to the human together in a single oral dosage composition such as a tablet or capsule, or each agent can be administered to the human in separate oral dosage formulations. Where separate dosage formulations are used, the compounds of the invention and one or more additional active agents can be administered to the human at essentially the same time, i.e., concurrently, or at separately staggered times, i.e., sequentially; combination therapy is understood to include all these regimens.

EMBODIMENTS OF THE INVENTION

Of the various aspects of the invention, as set forth above in the Summary of the Invention, certain embodiments are preferred:

One embodiment are the compounds of formula (I) wherein:
$R^1$ and $R^2$ are both hydrogen or are both deuterium;
$R^3$ and $R^4$ are both hydrogen or are both deuterium;
$R^5$ and $R^6$ are both hydrogen or are both deuterium;
$R^7$ and $R^8$ are both hydrogen or are both deuterium;
$R^9$ and $R^{10}$ are each independently hydroxy, methoxy or —$OCD_3$;
$R^{11}$ is hydrogen or deuterium;
$R^{12}$ and $R^{13}$ are both hydrogen or are both deuterium; and
$R^{14}$, $R^{15}$, and $R^{16}$ are all hydrogen or all deuterium.

Another embodiment are the compounds of formula (I) wherein:
$R^1$ and $R^2$ are both hydrogen or are both deuterium;
$R^3$ and $R^4$ are both hydrogen or are both deuterium;
$R^5$ and $R^6$ are both deuterium;
$R^7$ and $R^8$ are both hydrogen or are both deuterium;
$R^9$ and $R^{10}$ are each independently hydroxy, methoxy or —$OCD_3$;
$R^{11}$ is hydrogen or deuterium;
$R^{12}$ and $R^{13}$ are both hydrogen or are both deuterium; and
$R^{14}$, $R^{15}$, and $R^{16}$ are all hydrogen or all deuterium.

Another embodiment are the compounds of formula (I) wherein:
$R^1$ and $R^2$ are both hydrogen or are both deuterium;
$R^3$ and $R^4$ are both hydrogen or are both deuterium;
$R^5$ and $R^6$ are both hydrogen or are both deuterium;
$R^7$ and $R^8$ are both deuterium;
$R^9$ and $R^{10}$ are each independently hydroxy, methoxy or —$OCD_3$;
$R^{11}$ is hydrogen or deuterium;
$R^{12}$ and $R^{13}$ are both hydrogen or are both deuterium; and
$R^{14}$, $R^{15}$, and $R^{16}$ are all hydrogen or all deuterium.

Another embodiment are the compounds of formula (I) wherein:
$R^1$ and $R^2$ are both deuterium;
$R^3$ and $R^4$ are both deuterium;
$R^5$ and $R^6$ are both hydrogen or are both deuterium;
$R^7$ and $R^8$ are both hydrogen or are both deuterium;
$R^9$ and $R^{10}$ are each independently hydroxy, methoxy or —$OCD_3$;
$R^{11}$ is hydrogen or deuterium;
$R^{12}$ and $R^{13}$ are both hydrogen or are both deuterium; and
$R^{14}$, $R^{15}$, and $R^{16}$ are all hydrogen or all deuterium.

Another embodiment are the compounds of formula (I) wherein:
$R^1$ and $R^2$ are both hydrogen or are both deuterium;
$R^3$ and $R^4$ are both hydrogen or are both deuterium;
$R^5$ and $R^6$ are both hydrogen or are both deuterium;
$R^7$ and $R^8$ are both hydrogen or are both deuterium;
$R^9$ is —$OCD_3$;
$R^{10}$ is hydroxy, methoxy or —$OCD_3$;
$R^{11}$ is hydrogen or deuterium;
$R^{12}$ and $R^{13}$ are both hydrogen or are both deuterium; and
$R^{14}$, $R^{15}$, and $R^{16}$ are all hydrogen or all deuterium.

Another embodiment are the compounds of formula (I) wherein:
$R^1$ and $R^2$ are both hydrogen or are both deuterium;
$R^3$ and $R^4$ are both hydrogen or are both deuterium;
$R^5$ and $R^6$ are both hydrogen or are both deuterium;
$R^7$ and $R^8$ are both hydrogen or are both deuterium;
$R^9$ is hydroxy, methoxy or —$OCD_3$;
$R^{10}$ is —$OCD_3$;
$R^{11}$ is hydrogen or deuterium;
$R^{12}$ and $R^{13}$ are both hydrogen or are both deuterium; and
$R^{14}$, $R^{15}$, and $R^{16}$ are all hydrogen or all deuterium.

Another embodiment are the compounds of formula (I) wherein:
$R^1$ and $R^2$ are both hydrogen or are both deuterium;
$R^3$ and $R^4$ are both hydrogen or are both deuterium;
$R^5$ and $R^6$ are both hydrogen or are both deuterium;
$R^7$ and $R^8$ are both hydrogen or are both deuterium;
$R^9$ and $R^{10}$ are each independently hydroxy, methoxy or —$OCD_3$;
$R^{11}$ is deuterium;
$R^{12}$ and $R^{13}$ are both hydrogen or are both deuterium; and
$R^{14}$, $R^{15}$, and $R^{16}$ are all hydrogen or all deuterium.

Another embodiment are the compounds of formula (I) wherein:
$R^1$ and $R^2$ are both hydrogen or are both deuterium;
$R^3$ and $R^4$ are both hydrogen or are both deuterium;
$R^5$ and $R^6$ are both hydrogen or are both deuterium;
$R^7$ and $R^8$ are both hydrogen or are both deuterium;
$R^9$ and $R^{10}$ are each independently hydroxy, methoxy or —$OCD_3$;
$R^{11}$ is hydrogen or deuterium;
$R^{12}$ and $R^{13}$ are both deuterium; and
$R^{14}$, $R^{15}$, and $R^{16}$ are all hydrogen or all deuterium.

Another embodiment are the compounds of formula (I):

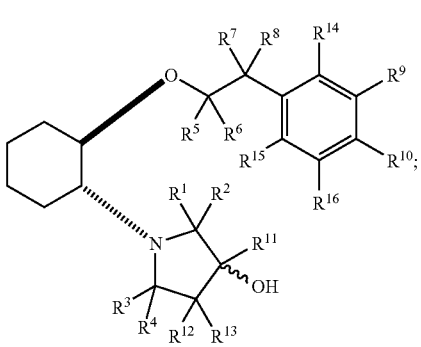

wherein:
$R^1$, $R^2$, $R^3$, $R^4$, $R^5$, $R^6$, $R^7$, $R^8$, $R^{11}$, $R^{12}$, $R^{13}$, $R^{14}$, $R^{15}$ and $R^{16}$ are each independently hydrogen or deuterium;
$R^9$ and $R^{10}$ are each independently hydroxy, methoxy or —$OCD_3$;
at least one deuterium is present and when $R^{10}$ is —$OCD_3$, then at least one of $R^1$, $R^2$, $R^3$, $R^4$, $R^5$, $R^6$, $R^6$, $R^8$, $R^{12}$ and $R^{13}$ is deuterium;
and when $R^5$, $R^6$, $R^7$, and $R^8$ are deuterium, $R^9$ and $R^{10}$ are both —$OCH_3$, then at least one of $R^3$, $R^4$, $R^{12}$ or $R^{13}$ is deuterium;
and when $R^{14}$, $R^{15}$, and $R^{16}$ are each deuterium, at least one of $R^1$, $R^2$, $R^3$, $R^4$, $R^5$, $R^6$, $R^7$, $R^8$, $R^{11}$, $R^{12}$ and $R^{13}$ is deuterium;

as an isolated stereoisomer or as a mixture of stereoisomers;
or a pharmaceutically acceptable salt thereof.

Another embodiment are the compounds of formula (I) which do not include the following compounds:

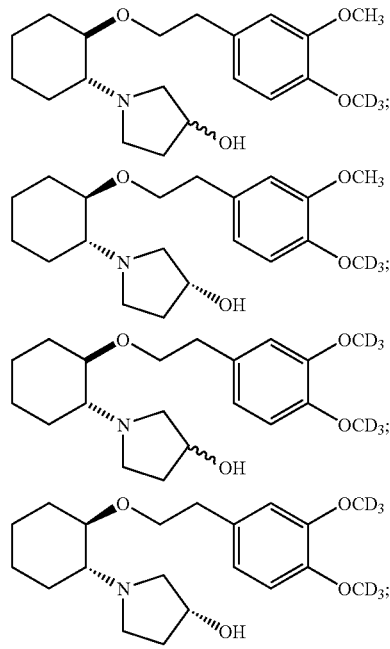

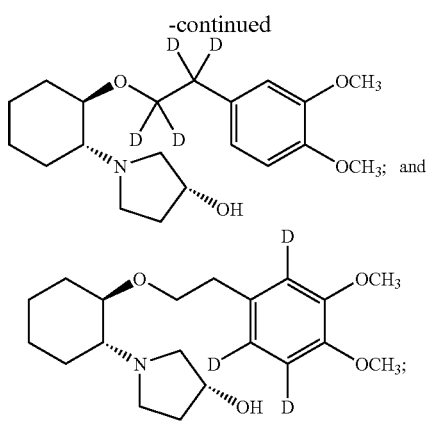

or pharmaceutically acceptable salts thereof.

Another embodiment of the invention are the compounds of formula (II) wherein:
$R^1$ and $R^2$ are both hydrogen or are both deuterium;
$R^3$ and $R^4$ are both hydrogen or are both deuterium;
$R^5$ and $R^6$ are both hydrogen or are both deuterium;
$R^7$ and $R^8$ are both hydrogen or are both deuterium;
$R^9$ and $R^{10}$ are each independently hydroxy, methoxy or —$OCD_3$;
$R^{11}$ is hydrogen or deuterium; and
$R^{12}$ and $R^{13}$ are both hydrogen or are both deuterium.

Another embodiment are the compounds of formula (II) wherein:
$R^1$ and $R^2$ are both hydrogen or are both deuterium;
$R^3$ and $R^4$ are both hydrogen or are both deuterium;
$R^5$ and $R^6$ are both deuterium;
$R^7$ and $R^8$ are both hydrogen or are both deuterium;
$R^9$ and $R^{10}$ are each independently hydroxy, methoxy or —$OCD_3$;
$R^{11}$ is hydrogen or deuterium; and
$R^{12}$ and $R^{13}$ are both hydrogen or are both deuterium.

Another embodiment are the compounds of formula (II) wherein:
$R^1$ and $R^2$ are both hydrogen or are both deuterium;
$R^3$ and $R^4$ are both hydrogen or are both deuterium;
$R^5$ and $R^6$ are both hydrogen or are both deuterium;
$R^7$ and $R^8$ are both deuterium;
$R^9$ and $R^{10}$ are each independently hydroxy, methoxy or —$OCD_3$;
$R^{11}$ is hydrogen or deuterium; and
$R^{12}$ and $R^{13}$ are both hydrogen or are both deuterium;

Another embodiment are the compounds of formula (II) wherein:
$R^1$ and $R^2$ are both deuterium;
$R^3$ and $R^4$ are both deuterium;
$R^5$ and $R^6$ are both hydrogen or are both deuterium;
$R^7$ and $R^8$ are both hydrogen or are both deuterium;
$R^9$ and $R^{10}$ are each independently hydroxy, methoxy or —$OCD_3$;
$R^{11}$ is hydrogen or deuterium; and
$R^{12}$ and $R^{13}$ are both hydrogen or are both deuterium.

Another embodiment are the compounds of formula (II) wherein:
$R^1$ and $R^2$ are both hydrogen or are both deuterium;
$R^3$ and $R^4$ are both hydrogen or are both deuterium;
$R^5$ and $R^6$ are both hydrogen or are both deuterium;
$R^7$ and $R^8$ are both hydrogen or are both deuterium;
$R^9$ is —$OCD_3$;
$R^{10}$ is hydroxy, methoxy or —$OCD_3$;
$R^{11}$ is hydrogen or deuterium; and
$R^{12}$ and $R^{13}$ are both hydrogen or are both deuterium.

Another embodiment are the compounds of formula (II) wherein:
$R^1$ and $R^2$ are both hydrogen or are both deuterium;
$R^3$ and $R^4$ are both hydrogen or are both deuterium;
$R^5$ and $R^6$ are both hydrogen or are both deuterium;
$R^7$ and $R^8$ are both hydrogen or are both deuterium;
$R^9$ is hydroxy, methoxy or —$OCD_3$;
$R^{10}$ is —$OCD_3$;
$R^{11}$ is hydrogen or deuterium; and
$R^{12}$ and $R^{13}$ are both hydrogen or are both deuterium.

Another embodiment are the compounds of formula (II) wherein:
$R^1$ and $R^2$ are both hydrogen or are both deuterium;
$R^3$ and $R^4$ are both hydrogen or are both deuterium;
$R^5$ and $R^6$ are both hydrogen or are both deuterium;
$R^7$ and $R^8$ are both hydrogen or are both deuterium;
$R^9$ and $R^{10}$ are each independently hydroxy, methoxy or —$OCD_3$;
$R^{11}$ is deuterium; and
$R^{12}$ and $R^{13}$ are both hydrogen or are both deuterium.

Another embodiment are the compounds of formula (II) wherein:
$R^1$ and $R^2$ are both hydrogen or are both deuterium;
$R^3$ and $R^4$ are both hydrogen or are both deuterium;
$R^5$ and $R^6$ are both hydrogen or are both deuterium;
$R^7$ and $R^8$ are both hydrogen or are both deuterium;
$R^9$ and $R^{10}$ are each independently hydroxy, methoxy or —$OCD_3$;
$R^{11}$ is hydrogen or deuterium; and
$R^{12}$ and $R^{13}$ are both deuterium.

The present invention also provides protonated versions of all of the compounds described in this specification that may be prepared by the method of the present invention. That is, for each compound described in this specification, the invention also includes the quaternary protonated amine form of the compound that may be prepared by the method of the present invention. These quaternary protonated amine form of the compounds may be present in the solid phase, for example in crystalline or amorphous form, and may be present in solution. These quaternary protonated amine form of the compounds may be associated with pharmaceutically acceptable anionic counter ions, including but not limited to those described in for example: "Handbook of Pharmaceutical Salts, Properties, Selection, and Use", P. Heinrich Stahl and Camille G. Wermuth (Eds.), Published by VHCA (Switzerland) and Wiley-VCH (FRG), 2002.

Preparation of the Compounds of the Invention

The present invention provides synthetic methodology for the preparation of compounds of formula (I) and compounds of formula (II) as described herein. It is understood that in the following Reaction Schemes, combinations of substituents and/or variables of the depicted formulae are permissible only if such contributions result in stable compounds.

It will also be appreciated by those skilled in the art that in the processes described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters.

Protecting groups may be added or removed in accordance with standard techniques, which are known to one of ordinary skill in the art and as described herein.

The use of protecting groups is described in detail in Green, T. W. and P. G. M. Wuts, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It is understood that one of ordinary skill in the art would be able to make the compounds of the invention by methods similar to the methods described herein or by methods known to one of ordinary skill in the art. It is also understood that one of ordinary skill in the art would be able to make in a similar manner as described below other compounds of formula (I) and compound of formula (II) not specifically illustrated below by using the appropriate starting components and modifying the parameters of the synthesis as needed. In general, starting components may be obtained from sources such as Aldrich Chemical Co., Sigma, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

When using reagents containing deuterium, it may not always be possible to obtain reagents that are completely deuterated. Using reagents with the highest possible deuteration will result in maximum desired deuteration, including complete deuteration when using 100% deuterated reagents. Alternatively, it may be possible to use partially deuterated reagents such that less deuteration of the final product is achieved. It is understood to a person of skill in the art that partially deuterated compounds, mixtures of partially deuterated compounds with completely deuterated compounds and mixtures of non-deuterated compounds with partially deuterated compounds with completely deuterated compounds may be prepared by using non-fully deuterated reagents. The reaction schemes described herein are described with respect to using 100% deuterated reagents.

In the following Reaction Schemes, the following common abbreviations are used:
Ac for $C_2$-$C_5$acyl group
AcCl for $C_2$-$C_5$acyl chloride
Bn for benzyl
DBU for 1,8-diazabicyclo(5.4.0)undec-7-ene
DME for dimethyl ether
$Et_2O$ for diethyl ether
MeOH for methanol
THF for tetrahydrofuran The synthetic procedures described herein, especially when taken with the general knowledge in the art, provide sufficient guidance to those of ordinary skill in the art to perform the synthesis, isolation, and purification of the compounds of the present invention. Further, it is contemplated that the individual features of these embodiments and examples may be combined with the features of one or more other embodiments or examples.

Methods for resolution of diastereomeric mixtures or racemic mixtures of the compounds of formula (I) and compounds of formula (II) or intermediates prepared herein are well known in the art (e.g., E.L. Eliel and S.H. Wilen, in Stereochemistry of Organic Compounds; John Wiley & Sons: New York, 1994; Chapter 7, and references cited therein). Suitable processes such as crystallization (e.g. preferential crystallization, preferential crystallization in the presence of additives), asymmetric transformation of racemates, chemical separation (e.g. formation and separation of diastereomers such as diastereomeric salt mixtures or the use of other resolving agents; separation via complexes and inclusion compounds), kinetic resolution (e.g. with titanium tartrate catalyst), enzymatic resolution (e.g., lipase mediated) and chromatographic separation (e.g., HPLC with chiral stationary phase and/or with simulated moving bed technology, or supercritical fluid chromatography and related techniques) are some of the examples that may be applied (see e.g., T. J. Ward, Analytical Chemistry, 2002, 2863-2872).

For purposes of illustration only, an asterisk (*) in the formulae in the following Reaction Schemes indicates a carbon having two deuterium atoms attached thereto.

A. Preparation of Compounds of Formula (I)

In the following Reaction Scheme 1 compounds of formula (I) where $R^{14}$, $R^{15}$, and $R^{16}$ are each hydrogen are illustrated as being prepared. It is understood that the specific stereoisomers of compounds of formula (I) can be prepared in a similar fashion utilizing the appropriately substituted chiral starting material. The present invention also encompasses the preparation of the pharmaceutically acceptable salts of the compounds of formula (I).

In general, compounds of formula (I), as set forth above in the Summary of the Invention, where $R^{14}$, $R^{15}$, and $R^{16}$ are each hydrogen, can be prepared by the method disclosed in Reaction Scheme 1 wherein $R^1$, $R^2$, $R^3$, $R^4$, $R^5$, $R^6$, $R^7$, $R^8$, $R^9$, $R^{10}$, $R^{11}$ and $R^{12}$ are as described above in the Summary of the Invention for the compounds of formula (I), R is $C_2$-$C_5$acyl and Q is a leaving group, preferably trihaloacetimidate:

REACTION SCHEME 1

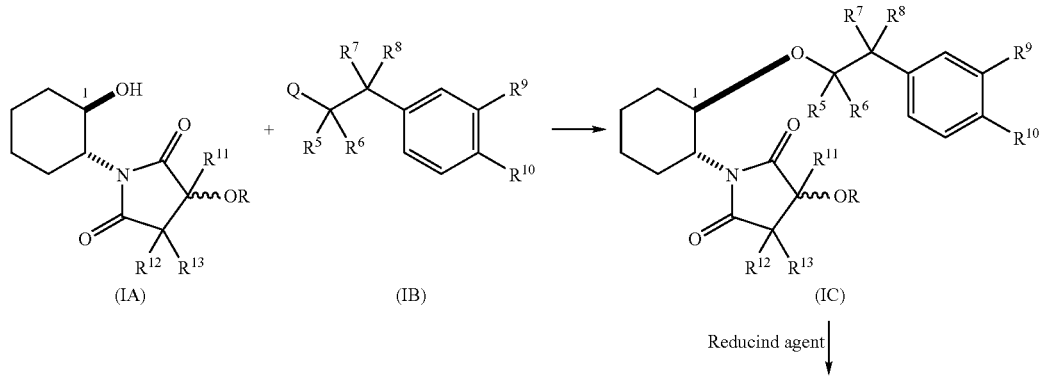

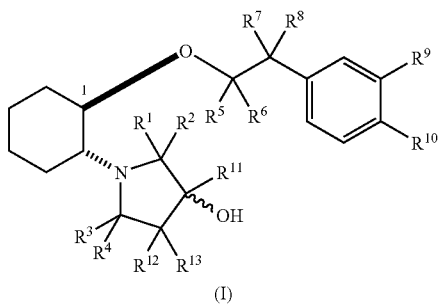

(I)

Compounds of formula (IA) and compounds of formula (IB) can be prepared by methods known to one skilled in the art or by methods disclosed herein or can be obtained commercially.

Compounds of formula (I) are prepared as illustrated above in Reaction Scheme 1 by first treating a compound of formula (IA) with a compound of formula (IB) under suitable etherification conditions such that upon reaction of the compound of formula (IA) with the compound of formula (IB), the stereochemical configuration of the carbon at the 1-position of the compound of formula (IA) is retained in the resulting compound of formula (IC). Preferably, such suitable conditions are catalytic Lewis acid conditions (e.g., $HBF_4$ etherate or $BF_3$ etherate). The compound of formula (IC) is then reduced with a suitable deuterated or non-deuterated reducing agent to yield a compound of formula (I). Salts of the compound of formula (I) can be prepared by standard methods.

Compounds of formula (IA) can be prepared as illustrated below in Reaction Scheme 1A wherein PG is an oxygen-protecting group, preferably optionally substituted benzyl; $R^2$ is selected to form a compound of formula (IF) upon treatment with the compound of formula (ID), followed by cyclization, and is selected, but is not limited to, from the following radicals wherein the ⌇ line in the following represents the ⌇ bond between $R^2$ and the OR group in compounds of formula (IE):

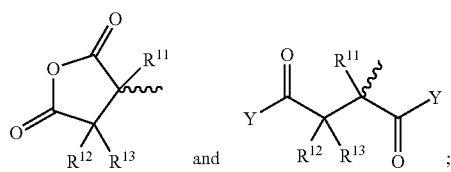

where each Y is halo; R is H, $C_2$-$C_5$ acyl or an oxygen-protecting group; and $R^{11}$, $R^{12}$ and $R^{13}$ are as defined above in the Summary of the Invention:

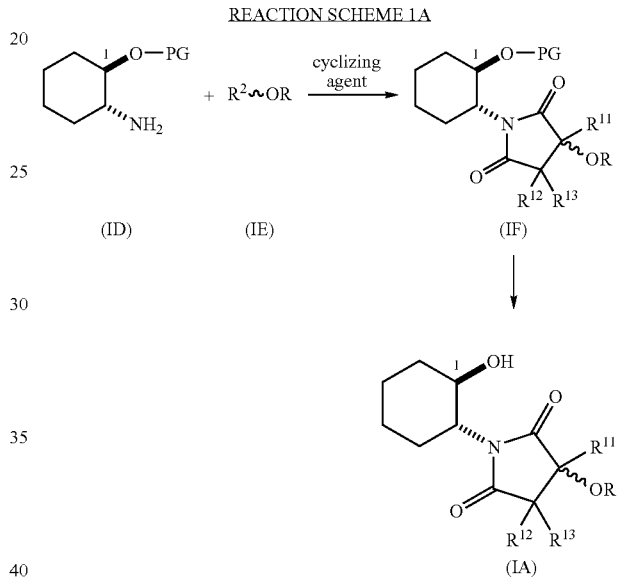

REACTION SCHEME 1A

In general, the compounds of formula (IA) are prepared in Reaction Scheme 1A by first treating a compound of formula (ID) with a compound of formula (IE) in an aprotic solvent, such as toluene, dichloromethane, or ethyl acetate, followed by the treatment with an cyclizing agent, such as a $C_2$-$C_5$ acyl halide or $C_2$-$C_5$ acyl anhydride, at temperatures of between about 0° C. to reflux temperature, preferably at reflux temperature, to form a compound of formula (IF). Alternatively, a compound of formula (ID) is first treated with a compound of formula (IE) in an aprotic solvent to yield a corresponding intermediate, which is then treated with a cyclizing agent to form compounds of formula (IF). Compounds of formula (IF) are then subjected to standard deprotection conditions known to one skilled in the art, such as hydrogenation in the presence of a catalyst under appropriate conditions, to form the compound of formula (IA), which is isolated from the reaction mixture by standard isolation techniques.

The following Reaction Schemes 2-16 illustrate various aspects of the methods of preparing compounds of formula (I) having the following trans stereochemistry at positions 1 and 2 of the cyclohexyl ring:

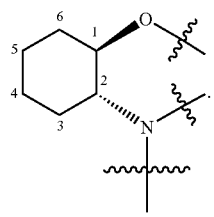

It is understood, however, that compounds of formula (I) having the following stereochemistry at positions 1 and 2 of the cyclohexyl ring:

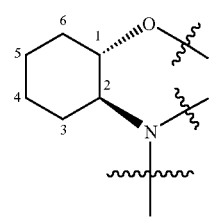

can be prepared in a similar manner using the appropriate chiral starting material or chiral reagent.

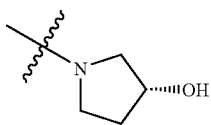

It is understood, however, that compounds of formula (I) having the following stereochemistry at position 3 of the pyrrolidinyl ring:

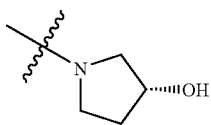

can be prepared in a similar manner using the appropriate chiral starting material or chiral reagent.

In the following Reaction Scheme 2, the compound of formula (I-1) is prepared.

The compound of formula (I-1) is a compound of formula (I) wherein $R^1$, $R^2$, $R^3$ and $R^4$ are each deuterium; $R^5$, $R^6$, $R^7$ and $R^8$ are each hydrogen; $R^9$ and $R^{10}$ are each methoxy; and $R^{11}$, $R^{12}$ and $R^{13}$ are each hydrogen, and $R^{14}$, $R^{15}$, and $R^{16}$ are each hydrogen:

REACTION SCHEME 2

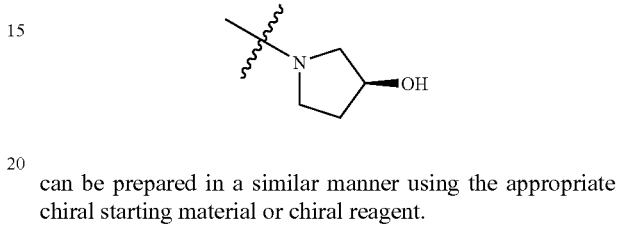

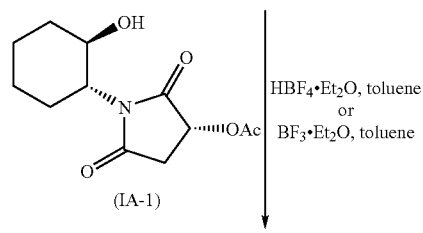

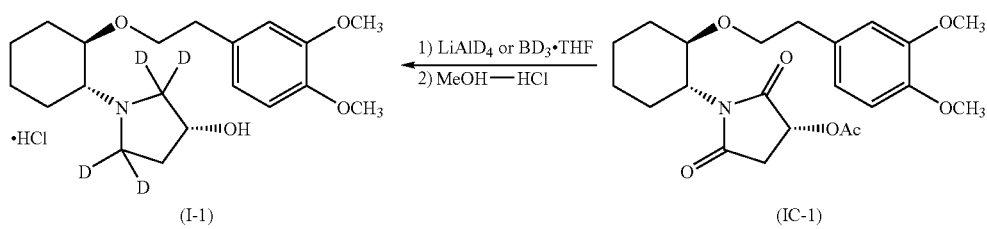

In addition, the following Reaction Schemes 2-16 illustrate various aspects of the methods of preparing compounds of formula (I) having the following stereochemistry at position 3 of the pyrrolidinyl ring:

The compound of formula (IG) is commercially available, for example, from Aldrich Chemical Co., or can be prepared by methods known to one skilled in the art. Deuterated borane and lithium aluminum deuteride are commercially available, for example, from Cambridge Isotope Laboratories. Compounds of formula (IA-1) can be prepared by the methods disclosed herein.

In general for the preparation of the compounds of formula (I-1), the compound of formula (IG) is treated with trichloroacetonitrile in the presence of a catalyst, preferably DBU, to form the compound of formula (IB-1). Etherification of compound of formula (IB-1) with compound of formula (IA-1) under catalytic Lewis acid conditions (e.g., $HBF_4$ etherate or $BF_3$ etherate in an aprotic solvent, such as toluene) gives the corresponding imido-ether of formula (IC-1). Successive reduction of compound of formula (IC-1) with a suitable deuterated reducing agent, for example, deuterated borane, $NaBD_4$/Lewis acid, $KBD_4$, or lithium aluminum deuteride, provides the compound of formula (I-1). Subsequent treatment with hydrogen chloride in methanol under standard conditions gives the hydrochloride salt of the compound of formula (I-1).

In the following Reaction Scheme 3, the compound of formula (I-2) is prepared. The compound of formula (I-2) is a compound of formula (I) wherein $R^1$, $R^2$, $R^3$ and $R^4$ are each deuterium; $R^5$ and $R^6$ are each hydrogen, $R^7$ and $R^8$ are each deuterium; $R^9$ and $R^{10}$ are each methoxy; and $R^{11}$, $R^{12}$ and $R^{13}$ are each hydrogen, and $R^{14}$, $R^{15}$, and $R^{16}$ are each hydrogen:

The compound of formula (IH) is commercially available, for example, from CDN Isotopes. Deuterated borane and lithium aluminum deuteride are commercially available, for example, from Cambridge Isotope Laboratories. Compounds of formula (IA-1) can be prepared by the methods disclosed herein.

In general for the preparation of the compound of formula (I-2), the compound of formula (IH) is treated with a suitable reducing agent, for example, lithium aluminum hydride or borane, under standard reducing conditions to form the compound of formula (IJ). The compound of formula (IJ) is treated with trichloroacetonitrile in the presence of a catalyst, preferably DBU, in an aprotic solvent, preferably dichloromethane, to form the compound of formula (IB-2). Etherification of compound of formula (IB-2) with compound of formula (IA-1) under catalytic Lewis acid conditions (e.g., $HBF_4$ etherate or $BF_3$ etherate in an aprotic solvent, such as toluene) gives the corresponding imido-ether of formula (IC-2). Successive reduction of compound of formula (IC-2) with a suitable deuterated reducing agent, for example, deuterated borane, $NaBD_4$/Lewis acid, $KBD_4$, or lithium aluminum deuteride, provides the compound of formula (I-2). Subsequent treatment with hydrogen chloride in methanol under standard conditions gives the hydrochloride salt of the compound of formula (I-2).

REACTION SCHEME 3

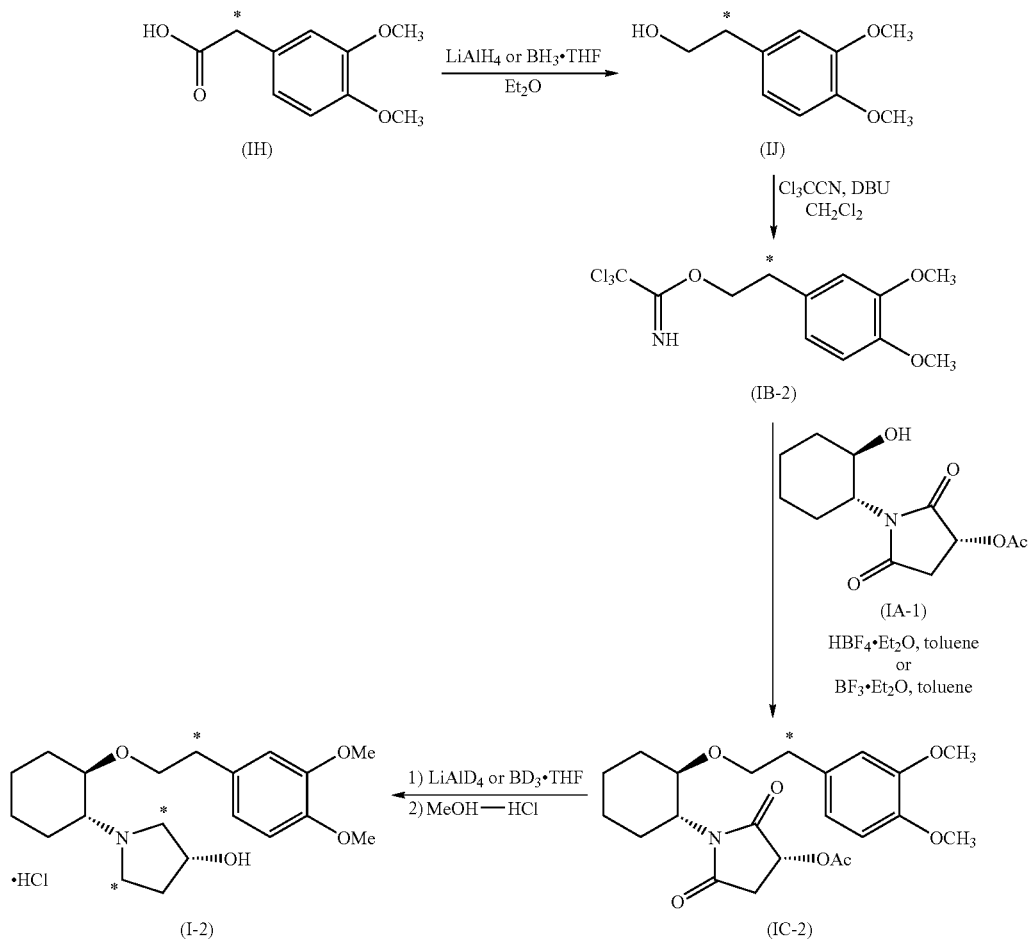

* = $D_2$

In the following Reaction Scheme 4, the compound of formula (I-3) and the compound of formula (I-4) are prepared. The compound of formula (I-3) is a compound of formula (I) wherein $R^1$, $R^2$, $R^3$ and $R^4$ are each deuterium; $R^5$, $R^6$, $R^7$ and $R^8$ are each deuterium; $R^9$ and $R^{10}$ are each methoxy; and $R^{11}$, $R^{12}$ and $R^{13}$ are each hydrogen. The compound of formula (I-4) is a compound of formula (I) wherein $R^1$, $R^2$, $R^3$ and $R^4$ are each hydrogen; $R^5$, $R^6$, $R^7$ and $R^8$ are each deuterium; $R^9$ and $R^{10}$ are each methoxy; and $R^{11}$, $R^{12}$ and $R^{13}$ are each hydrogen, and $R^{14}$, $R^{15}$, and $R^{16}$ are each hydrogen:

trile in the presence of a catalyst, preferably DBU, in an aprotic solvent, preferably dichloromethane, to form the compound of formula (IB-3). Etherification of compound of formula (IB-3) with compound of formula (IA-1) under catalytic Lewis acid conditions (e.g., $HBF_4$ etherate or $BF_3$ etherate in an aprotic solvent, such as toluene) gives the corresponding imido-ether of formula (IC-3). Successive reduction of compound of formula (IC-3) with a suitable deuterated reducing agent, for example, deuterated borane, $NaBD_4$/Lewis acid, $KBD_4$, or lithium aluminum deuteride, provides the compound of formula (I-3). Subsequent treat-

REACTION SCHEME 4

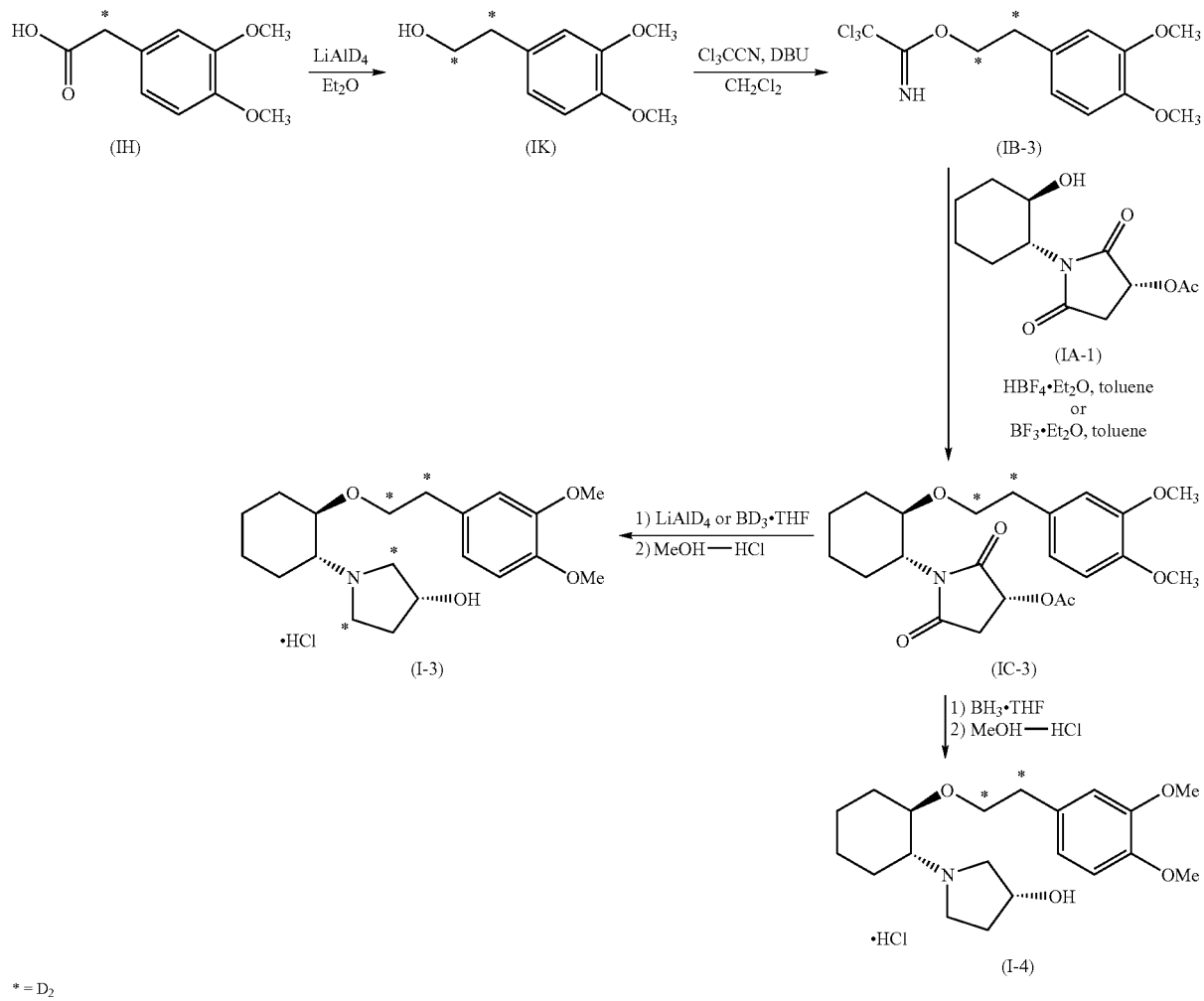

\* = $D_2$

The compound of formula (IH) is commercially available, for example, from CDN Isotopes. Deuterated borane and lithium aluminum deuteride are commercially available, for example, from Cambridge Isotope Laboratories. Compounds of formula (IA-1) can be prepared by the methods disclosed herein.

In general for the preparation of the compound of formula (I-3) and the compound of formula (I-4), the compound of formula (IH) is treated with a suitable reducing agent, for example, lithium aluminum deuteride, under standard reducing conditions to form the compound of formula (IK). The compound of formula (IK) is treated with trichloroacetoniment with hydrogen chloride in methanol under standard conditions gives the hydrochloride salt of the compound of formula (I-3). Alternatively, successive reduction of compound of formula (IC-3) with a suitable reducing agent, for example, borane, $NaBH_4$/Lewis acid, $KBH_4$, or lithium aluminum hydride, provides the compound of formula (I-4). Subsequent treatment with hydrogen chloride in methanol under standard conditions gives the hydrochloride salt of the compound of formula (I-4).

In the following Reaction Scheme 5, the compound of formula (I-5) is prepared. The compound of formula (I-5) is a compound of formula (I) wherein $R^1$, $R^2$, $R^3$ and $R^4$ are each deuterium; $R^5$, $R^6$, $R^7$ and $R^8$ are each hydrogen; $R^9$ is methoxy; $R^{10}$ is —$OCD_3$; and $R^{11}$, $R^{12}$ and $R^{13}$ are each hydrogen, and $R^{14}$, $R^{15}$, and $R^{16}$ are each hydrogen:

of formula (IC-4). Successive reduction of compound of formula (IC-4) with a suitable deuterated reducing agent, for example, deuterated borane, $NaBD_4$/Lewis acid, $KBD_4$, or lithium aluminum deuteride, provides the compound of formula (I-5). Subsequent treatment with hydrogen chloride in methanol under standard conditions gives the hydrochloride salt of the compound of formula (I-5).

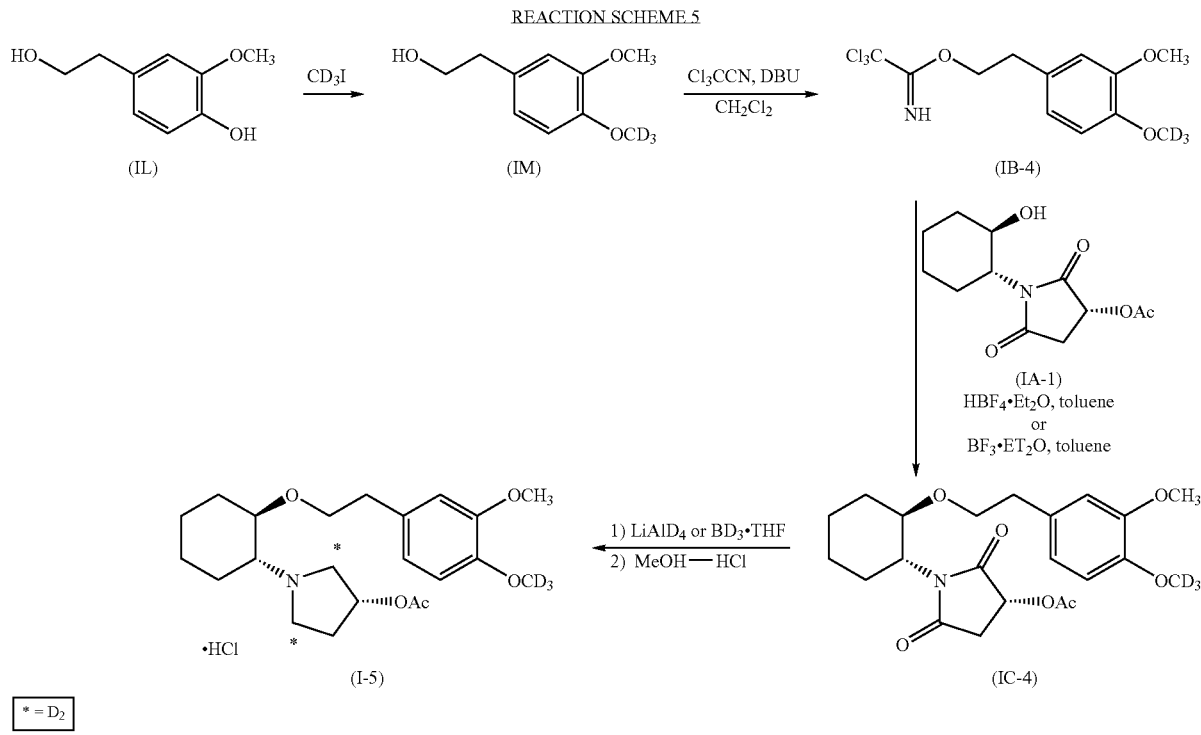

The compound of formula (IL) is commercially available, for example, from Aldrich Chemical Co., or can be prepared by methods known to one skilled in the art. $CD_3I$ is commercially available. Deuterated borane and lithium aluminum deuteride are commercially available, for example, from Cambridge Isotope Laboratories. Compounds of formula (IA-1) can be prepared by the methods disclosed herein.

In general for the preparation of the compound of formula (I-5), the compound of formula (IL) is treated with $CD_3I$ under standard aromatic nucleophilic substitution conditions to form a compound of formula (IM). The compound of formula (IM) is then treated with trichloroacetonitrile in the presence of a catalyst, preferably DBU, in an aprotic solvent, preferably dichloromethane, to form the compound of formula (IB-4). Etherification of compound of formula (IB-4) with compound of formula (A-1) under catalytic Lewis acid conditions (e.g., $HBF_4$ etherate or $BF_3$ etherate in an aprotic solvent, such as toluene) gives the corresponding imido-ether In the following Reaction Scheme 6, the compound of formula (I-5) and the compound of (1-6) are prepared. As noted above, the compound of formula (I-5) is a compound of formula (I) wherein $R^1$, $R^2$, $R^3$ and $R^4$ are each deuterium; $R^5$, $R^6$, $R^7$ and $R^8$ are each hydrogen; $R^9$ is methoxy; $R^{10}$ is —$OCD_3$; and $R^{11}$, $R^{12}$ and $R^{13}$ are each hydrogen. The compound of formula (1-6) is a compound of formula (I) wherein $R^1$, $R^2$, $R^3$ and $R^4$ are each deuterium; $R^5$ and $R^6$ are each deuterium; $R^7$ and $R^8$ are each hydrogen; $R^9$ is methoxy; $R^{10}$ is —$OCD_3$; and $R^{11}$, $R^{12}$ and $R^{13}$ are each hydrogen, and $R^{14}$, $R^{15}$, and $R^{16}$ are each hydrogen:

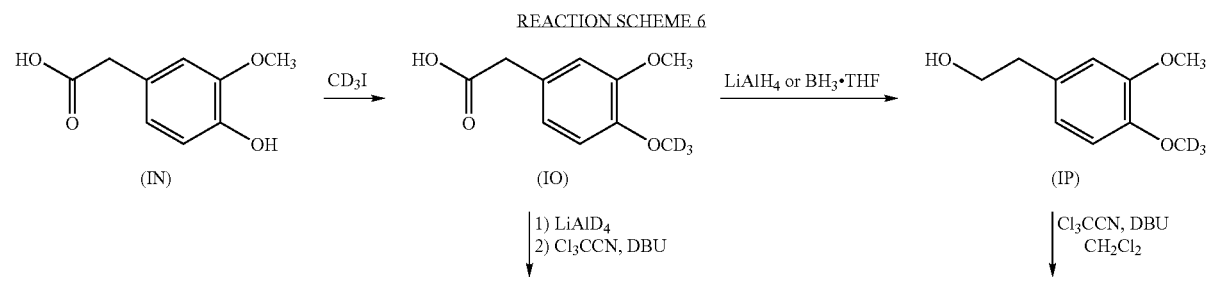

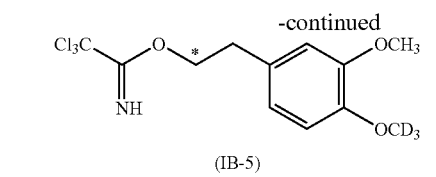
(IB-5)

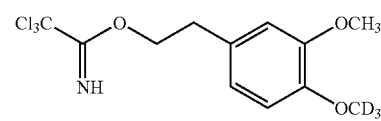
(IB-6)

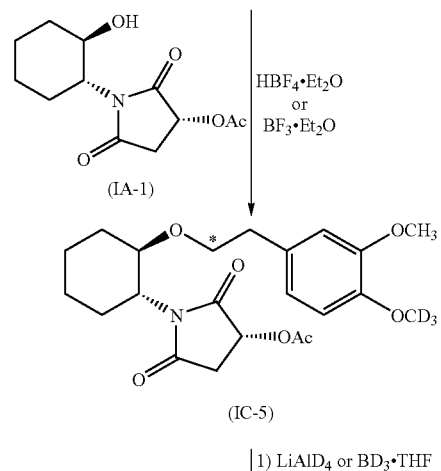
(IA-1) → (IC-5)

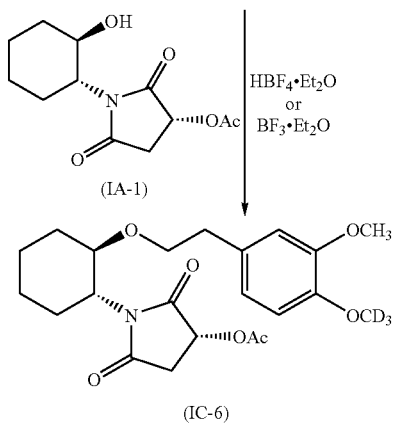
(IA-1) → (IC-6)

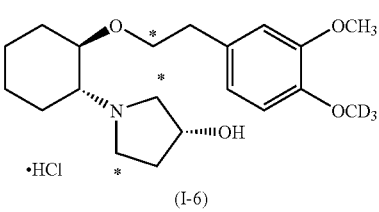
(I-6)

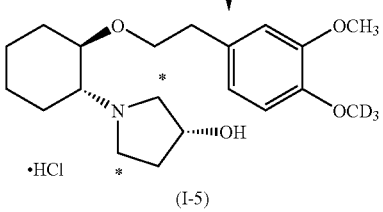
(I-5)

\* = D₂

The compound of formula (IN) is commercially available, for example, from Aldrich Chemical Co., or can be prepared by methods known to one skilled in the art. CD₃I is commercially available. Deuterated borane and lithium aluminum deuteride are commercially available, for example, from Cambridge Isotope Laboratories.

Compounds of formula (IA-1) can be prepared by the methods disclosed herein.

In general for the preparation of the compound of formula (I-6), the compound of formula (IN) is treated with CD₃I under standard aromatic nucleophilic substitution conditions to form a compound of formula (IO). The compound of formula (IO) is then treated with a deuterated reducing agent, such as lithium aluminum deuteride, under standard reducing conditions and then treated with trichloroacetonitrile in the presence of a catalyst, preferably DBU, to form the compound of formula (IB-5). Etherification of compound of formula (IB-5) with compound of formula (IA-1) under catalytic Lewis acid conditions (e.g., HBF₄ etherate or BF₃ etherate in an aprotic solvent, such as toluene) gives the corresponding imido-ether of formula (IC-5). Successive reduction of compound of formula (IC-5) with a suitable deuterated reducing agent, for example, deuterated borane, NaBD₄/Lewis acid, KBD₄, or lithium aluminum deuteride, provides the compound of formula (I-6). Subsequent treatment with hydrogen chloride in methanol under standard conditions gives the hydrochloride salt of the compound of formula (I-6).

In general for the preparation of the compound of formula (I-5), the compound of formula (IN) is treated with CD₃I under standard aromatic nucleophilic substitution conditions to form a compound of formula (IO). The compound of formula (IO) is then treated with a reducing agent, such as lithium aluminum hydride or borane, under standard reducing conditions to form a compound of formula (IP). The compound of formula (IP) is then treated with trichloroacetonitrile in the presence of a catalyst, preferably DBU, in an aprotic solvent, preferably dichloromethane, to form the compound of formula (IB-6). Etherification of compound of formula (IB-6) with compound of formula (IA-1) under catalytic Lewis acid conditions (e.g., HBF₄ etherate or BF₃ etherate in an aprotic solvent, such as toluene) gives the corresponding imido-ether of formula (IC-6). Successive reduction of compound of formula (IC-6) with a suitable deuterated reducing agent, for example, deuterated borane, NaBD₄/Lewis acid, KBD₄, or lithium aluminum deuteride, provides the compound of formula (I-5). Subsequent treatment with hydrogen chloride in methanol under standard conditions gives the hydrochloride salt of the compound of formula (I-5).

In the following Reaction Scheme 7, the compound of formula (I-7) and the compound of (1-8) are prepared. The compound of formula (I-7) is a compound of formula (I) wherein $R^1$, $R^2$, $R^3$ and $R^4$ are each deuterium; $R^5$ and $R^6$ are each deuterium; $R^7$ and $R^8$ are each hydrogen; $R^9$ is —OCD₃; $R^{10}$ is methoxy; and $R^{11}$, $R^{12}$, and $R^{13}$ are each hydrogen. The compound of formula (I-8) is a compound of formula (1) wherein $R^1$, $R^2$, $R^3$ and $R^4$ are each deuterium; $R^5$, $R^6$, $R^7$ and $R^8$ are each hydrogen; $R^9$ is —$OCD_3$; $R^{10}$ is methoxy; and $R^{11}$, $R^{12}$ and $R^{13}$ are each hydrogen, and $R^{14}$, $R^{15}$, and $R^{16}$ are each hydrogen:

deuteride, followed by treatment with trichloroacetonitrile in the presence of a catalyst, preferably DBU, in an aprotic solvent, preferably dichloromethane, to form the compound of formula (IB-7). Etherification of compound of formula (IB-7) with compound of formula (IA-1) under catalytic

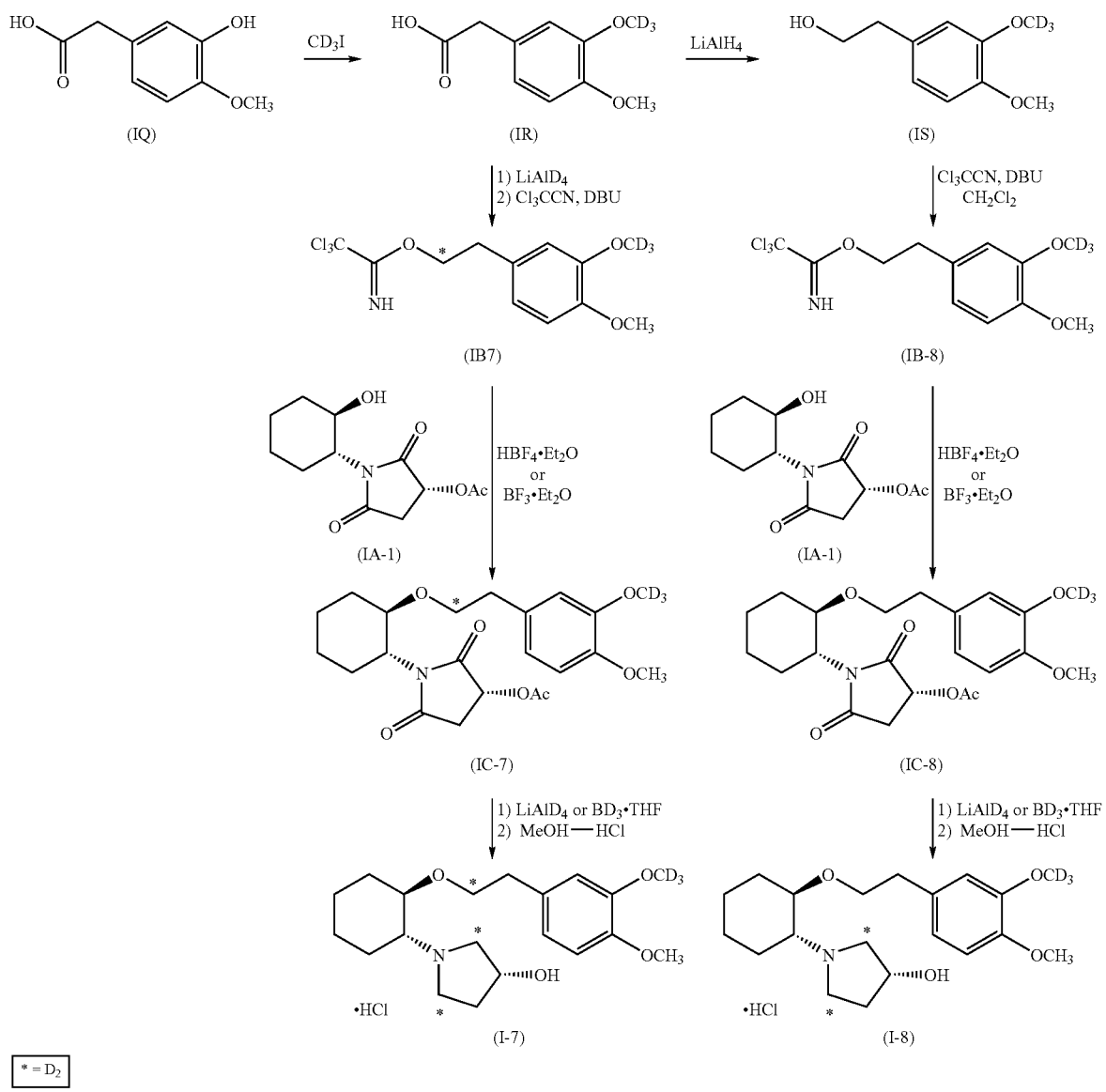

REACTION SCHEME 7

The compound of formula (IQ) is commercially available, for example, from Aldrich Chemical Co., or can be prepared by methods known to one skilled in the art. Deuterated borane, lithium aluminum deuteride and $CD_3I$ are also commercially available, for example, from Cambridge Isotope Laboratories. Compound of formula (IA-1) can be prepared by the methods disclosed herein.

In general for the preparation of the compound of formula (I-7) or the compound of formula (I-8), the compound of formula (IQ) is treated with $CD_3I$ under standard aromatic nucleophilic substitution conditions to form a compound of formula (IR). The compound of formula (IR) is then treated with a deuterated reducing agent, such as lithium aluminum Lewis acid conditions (e.g., $HBF_4$ etherate or $BF_3$ etherate in an aprotic solvent, such as toluene) gives the corresponding imido-ether of formula (IC-7). The compound of formula (IC-7) is then treated with a deuterated reducing agent, such as lithium aluminum deuteride or deuterated borane, in an aprotic solvent, such as THF, followed by workup with methanolic hydrochloride, for example, to produce the hydrochloride salt of the compound of formula (I-7).

Alternatively, the compound of formula (I-8) is prepared, as set forth above in Reaction Scheme 7, by reducing a compound of formula (IR) with a reducing agent such as lithium aluminum hydride to produce compound of formula (IS). Treatment of compound of formula (IS) with trichloroacetonitrile in the presence of a catalyst, preferably DBU, in an aprotic solvent, preferably dichloromethane, forms the compound of formula (IB-8). Etherification of compound of formula (IB-8) with compound of formula (IA-1) under catalytic Lewis acid conditions (e.g., HBF$_4$ etherate or BF$_3$ etherate in an aprotic solvent, such as toluene) gives the corresponding imido-ether of formula (IC-8). The compound of formula (IC-8) is then treated with a deuterated reducing agent, such as lithium aluminum deuteride or deuterated borane in an aprotic solvent such as THF followed by workup with methanolic hydrochloride, for example, to produce the hydrochloride salt of the compound of formula (I-8).

In the following Reaction Scheme 8, the compound of formula (I-9), the compound of formula (I-10), the compound of formula (I-11) and the compound of (1-12) are prepared. The compound of formula (I-9) is a compound of formula (I) wherein R$^1$, R$^2$, R$^3$ and R$^4$ are each hydrogen; R$^5$ and R$^6$ are each deuterium; R$^7$ and R$^8$ are each hydrogen; R$^9$ and R$^{10}$ are both —OCD$_3$; and R$^{11}$, R$^{12}$ and R$^{13}$ are each hydrogen. The compound of formula (I-10) is a compound of formula (I) wherein R$^1$, R$^2$, R$^3$ and R$^4$ are each hydrogen; R$^5$ and R$^6$ each hydrogen; R$^7$ and R$^8$ are each hydrogen; R$^9$ and R$^{10}$ are both —OCD$_3$; and R$^{11}$, R$^{12}$ and R$^{13}$ are each hydrogen. The compound of formula (I-11) is a compound of formula (I) wherein R$^1$, R$^2$, R$^3$ and R$^4$ are each deuterium; R$^5$ and R$^6$ are each deuterium; R$^7$ and R$^8$ are each hydrogen; R$^9$ and R$^{10}$ are both —OCD$_3$; and R$^{11}$, R$^{12}$ and R$^{13}$ are each hydrogen. The compound of formula (I-12) is a compound of formula (I) wherein R$^1$, R$^2$, R$^3$ and R$^4$ are each deuterium; R$^5$ and R$^6$ are each hydrogen; R$^7$ and R$^8$ are each hydrogen; R$^9$ and R$^{10}$ are both —OCD$_3$; and R$^{11}$, R$^{12}$ and R$^{13}$ are each hydrogen, and R$^{14}$, R$^{15}$, and R$^{16}$ are each hydrogen:

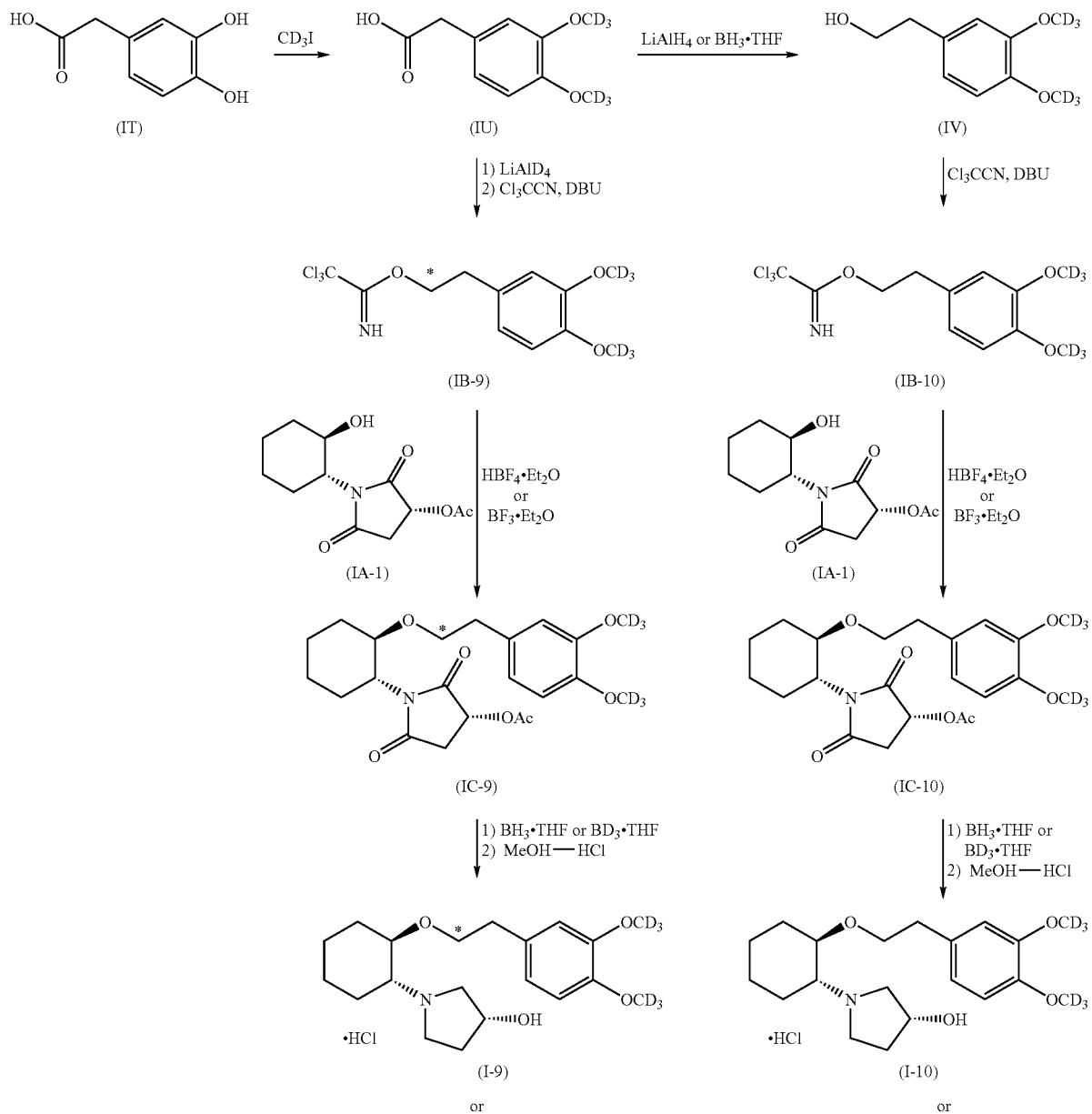

REACTION SCHEME 8

-continued

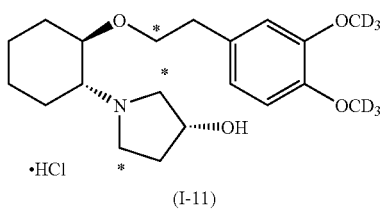
(I-11)

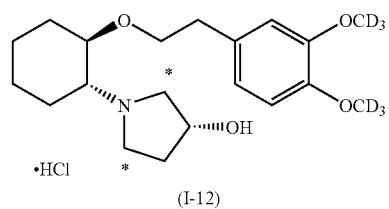
(I-12)

* = D₂

The compound of formula (IT) is commercially available, for example, from Aldrich Chemical Co., or can be prepared by methods known to one skilled in the art. Deuterated borane, lithium aluminum deuteride and CD₃I are also commercially available, for example, from Cambridge Isotope Laboratories. Compound of formula (IA-1) can be prepared by the methods disclosed herein.

In general for the preparation of the compound of formula (I-9) or the compound of formula (I-11), the compound of formula (IT) is treated with CD₃I under standard aromatic nucleophilic substitution conditions to form a compound of formula (IU). The compound of formula (IU) is then treated with a deuterated reducing agent such as lithium aluminum deuteride followed by treatment with trichloroacetonitrile in the presence of a catalyst, preferably DBU, in an aprotic solvent, preferably dichloromethane, to form the compound of formula (IB-9). Etherification of compound of formula (IB-9) with compound of formula (IA-1) under catalytic Lewis acid conditions (e.g., HBF₄ etherate or BF₃ etherate in an aprotic solvent, such as toluene) gives the corresponding imido-ether of formula (IC-9). The compound of formula (IC-9) is then treated with a reducing agent, such as borane, in an aprotic solvent, such as THF, followed by workup with methanolic hydrochloride, for example, to produce the hydrochloride salt of the compound of formula (I-9).

Alternatively, the compound of formula (IC-9) is treated with a deuterated reducing agent, such as deuterated borane, in an aprotic solvent, such as THF, followed by workup with methanolic hydrochloride, for example, to produce the hydrochloride salt of the compound of formula (I-11).

In general for the preparation of the compound of formula (I-10) or the compound of formula (I-12), a compound of formula (IU) can be reduced with a reducing agent, such as lithium aluminum hydride or borane, to produce compound of formula (IV). Treatment of compound of formula (IV) with trichloroacetonitrile in the presence of a catalyst, preferably DBU, in an aprotic solvent, preferably dichloromethane, forms the compound of formula (IB-10). Etherification of compound of formula (IB-10) with compound of formula (IA-1) under catalytic Lewis acid conditions (e.g., HBF₄ etherate or BF₃ etherate in an aprotic solvent, such as toluene) gives the corresponding imido-ether of formula (IC-10). The compound of formula (IC-10) is then treated with a reducing agent, such as borane, in an aprotic solvent, such as THF, followed by workup with methanolic hydrochloride, for example, to produce the hydrochloride salt of the compound of formula (I-10).

Alternatively, compound of formula (IC-10) is treated with a deuterated reducing agent, such as deuterated borane, in an aprotic solvent, such as THF, followed by workup with methanolic hydrochloride, for example, to produce the hydrochloride salt of the compound of formula (I-12).

Alternatively, in the following Reaction Scheme 9, the compound of formula (I-10) and the compound of formula (I-12) are prepared. The compound of formula (I-10), as noted above, is a compound of formula (I) wherein $R^1$, $R^2$, $R^3$ and $R^4$ are each hydrogen; $R^5$ and $R^6$ are each hydrogen; $R^7$ and $R^8$ are each hydrogen; $R^9$ and $R^{10}$ are both —OCD₃; and $R^{11}$, $R^{12}$ and $R^{13}$ are each hydrogen. The compound of formula (I-12) is a compound of formula (I) wherein $R^1$, $R^2$, $R^3$ and $R^4$ are each deuterium; $R^5$ and $R^6$ are each hydrogen; $R^7$ and $R^8$ are each hydrogen; $R^9$ and $R^{10}$ are both —OCD₃; and $R^{11}$, $R^{12}$ and $R^{13}$ are each hydrogen, and $R^{14}$, $R^{15}$, and $R^{16}$ are each hydrogen:

REACTION SCHEME 9

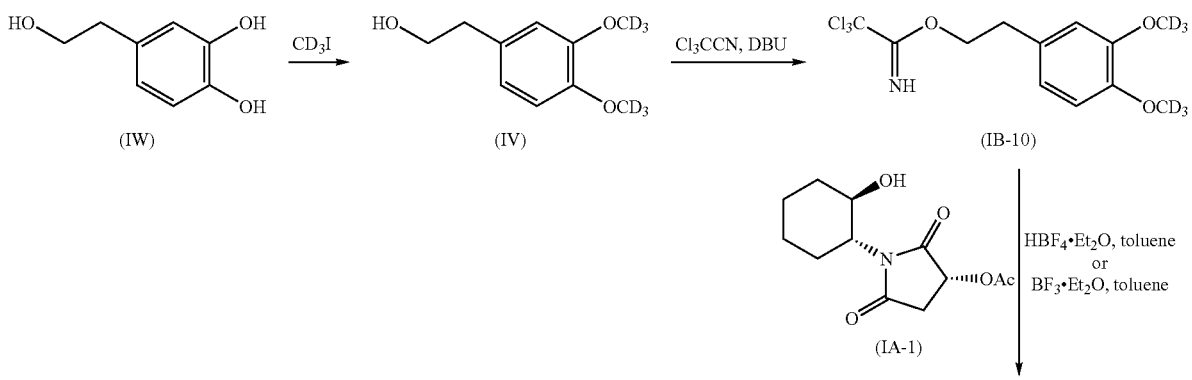

-continued

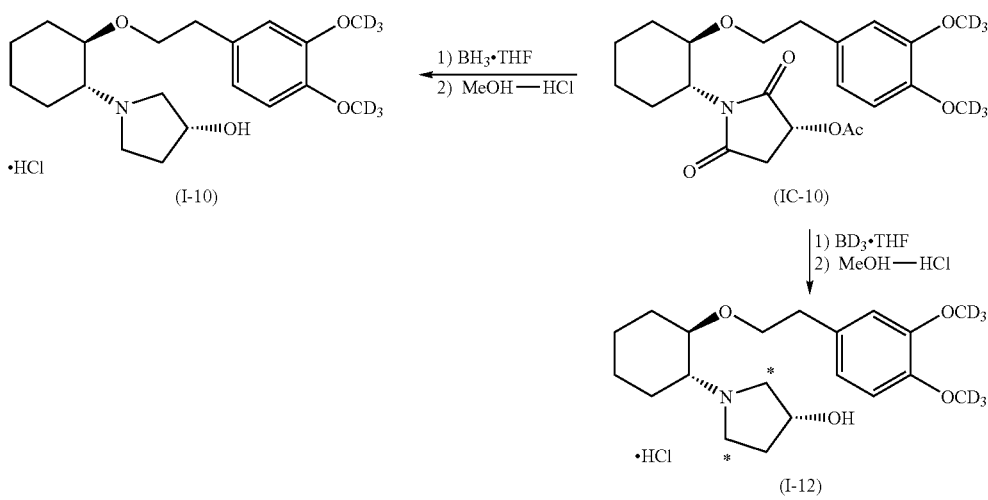

The compound of formula (IW) is commercially available, for example, from Aldrich Chemical Co., or can be prepared by methods known to one skilled in the art. Deuterated borane and CD$_3$I are also commercially available, for example, from Cambridge Isotope Laboratories. Compound of formula (IA-1) can be prepared by methods disclosed herein.

In general for the preparation of the compounds of formula (I-10) and the compound of formula (I-12), the compound of formula (IW) is treated with CD$_3$I under standard aromatic nucleophilic substitution conditions to form a compound of formula (IV). The compound of formula (IV) is then treated with trichoroacetonitrile in the presence of a catalyst, preferably DBU, in an aprotic solvent, preferably dichloromethane, to form the compound of formula (IB-10). Etherification of compound of formula (IB-10) with a compound of formula (IA-1) under catalytic Lewis acid conditions (e.g., HBF$_4$ etherate or BF$_3$ etherate in an aprotic solvent, such as toluene) gives the corresponding imido-ether of formula (IC-10). The compound of formula (IC-10) is then treated with a reducing agent, such as borane, in an aprotic solvent, such as THF, followed by a workup with methanolic hydrochloride, for example, to produce the hydrochloride salt of the compound of formula (I-10).

Alternatively, the compound of formula (IC-10) is treated with a deuterated reducing agent, such as deuterated borane, in an aprotic solvent, such as THF, followed by workup with methanolic hydrochloride, for example, to produce the hydrochloride salt of the compound of formula (I-12).

In the following Reaction Scheme 10, the compound of formula (I-13) and the compound of (1-14) are prepared. The compound of formula (I-13) is a compound of formula (I) wherein $R^1$, $R^2$, $R^3$ and $R^4$ are each hydrogen; $R^5$ and $R^6$ are each hydrogen; $R^7$ and $R^8$ are each deuterium; $R^9$ is methoxy, $R^{10}$ is —OCD$_3$; and $R^{11}$, $R^{12}$ and $R^{13}$ are each hydrogen. The compound of formula (I-12) is a compound of formula (I) wherein $R^1$, $R^2$, $R^3$ and $R^4$ are each deuterium; $R^5$ and $R^6$ are each hydrogen; $R^7$ and $R^8$ are each deuterium; $R^9$ is methoxy, $R^{10}$ is —OCD$_3$; and $R^{11}$, $R^{12}$ and $R^{13}$ are each hydrogen, and $R^{14}$, $R^{15}$, and $R^{16}$ are each hydrogen:

REACTION SCHEME 10

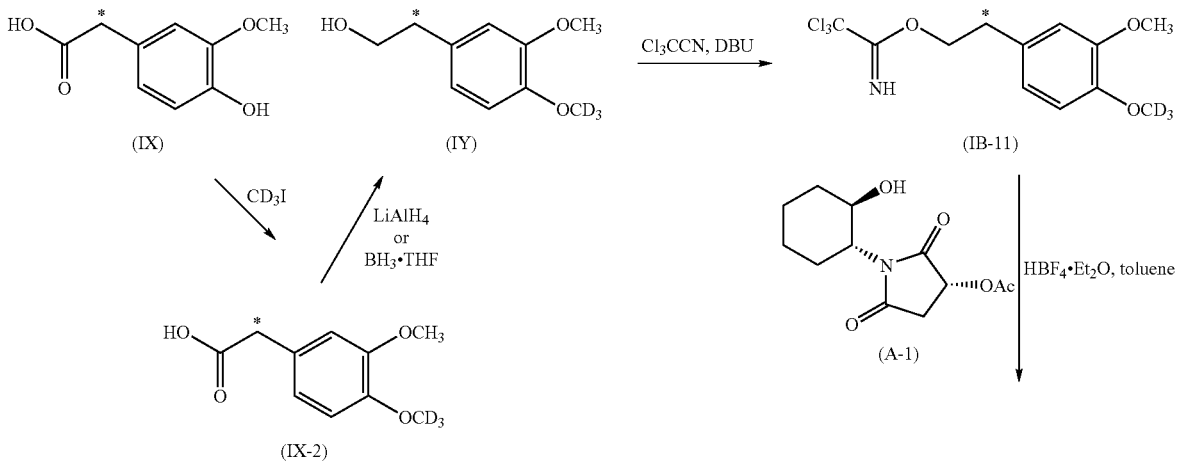

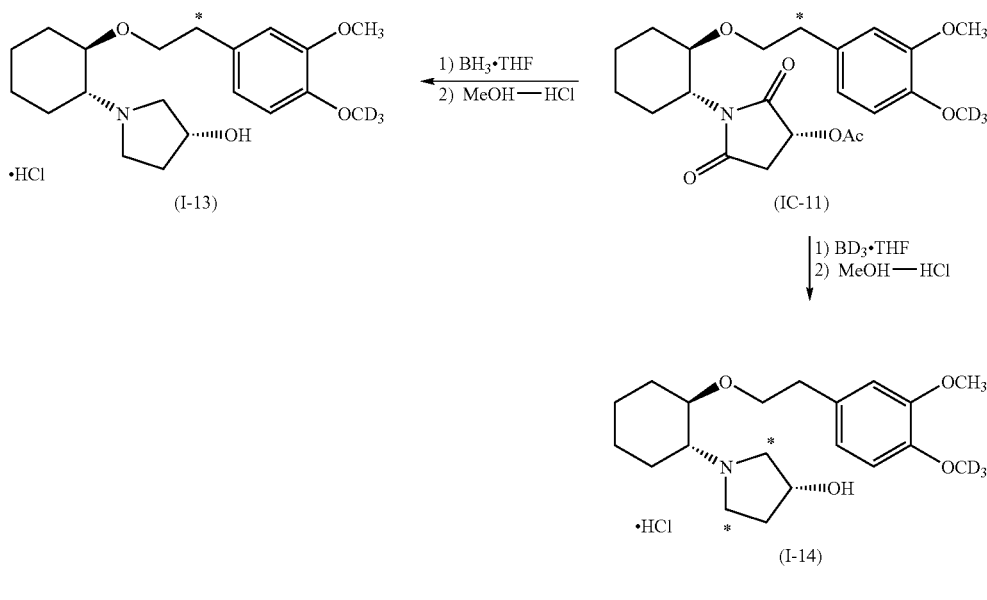

(I-13)

(IC-11)

1) BH₃•THF
2) MeOH—HCl

1) BD₃•THF
2) MeOH—HCl (I-14)

* = D₂

The compound of formula (IX) is commercially available, for example, from CDN Isotopes, or can be prepared by methods known to one skilled in the art. Deuterated borane and CD₃I are also commercially available, for example, from Cambridge Isotope Laboratories. Compound of formula (IA-1) can be prepared by the methods disclosed herein.

In general for the preparation of the compound of formula (I-13) or the compound of formula (I-14), the compound of formula (IX) is treated with CD₃I under standard aromatic nucleophilic substitution conditions to form a compound of formula (IX-2). The compound of formula (IX-2) is treatred with a reducing agent such as lithium aluminum hydride, under standard reducing conditions to form a compound of formula (IY). The compound of formula (IY) is then treated trichloroacetonitrile in the presence of a catalyst, preferably DBU, in an aprotic solvent, preferably dichloromethane, to form the compound of formula (IB-11). Etherification of compound of formula (IB-11) with compound of formula (IA-1) under catalytic Lewis acid conditions (e.g., HBF₄ etherate or BF₃ etherate in an aprotic solvent, such as toluene)

gives the corresponding imido-ether of formula (IC-11). The compound of formula (IC-11) is then treated with a reducing agent, such as borane, in an aprotic solvent, such as THF, followed by workup with methanolic hydrochloride, for example, to produce the hydrochloride salt of the compound of formula (I-13).

Alternatively, compound of formula (IC-11) is treated with a deuterated reducing agent, such as deuterated borane, in an aprotic solvent, such as THF, followed by workup with methanolic hydrochloride, for example, to produce the hydrochloride salt of the compound of formula (I-14).

In the following Reaction Scheme 11, the compound of formula (I-15) and the compound of (I-16) are prepared. The compound of formula (I-15) is a compound of formula (I) wherein $R^1$, $R^2$, $R^3$ and $R^4$ are each hydrogen; $R^5$, $R^6$, $R^7$ and $R^8$ are each deuterium; $R^9$ and $R^{10}$ are both methoxy; and $R^{11}$, $R^{12}$ and $R^{13}$ are each deuterium. The compound of formula (I-16) is a compound of formula (I) wherein $R^1$, $R^2$, $R^3$ and $R^4$ are each deuterium; $R^5$, $R^6$, $R^7$ and $R^8$ are each deuterium; $R^9$ and $R^{10}$ are both methoxy; and $R^{11}$, $R^{12}$ and $R^{13}$ are each deuterium, and $R^{14}$, $R^{15}$, and $R^{16}$ are each hydrogen:

REACTION SCHEME 11

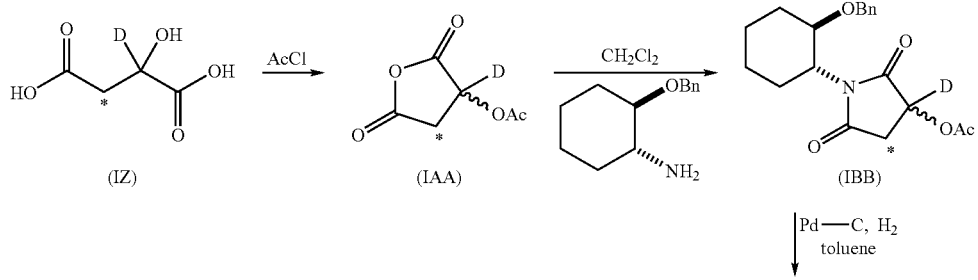

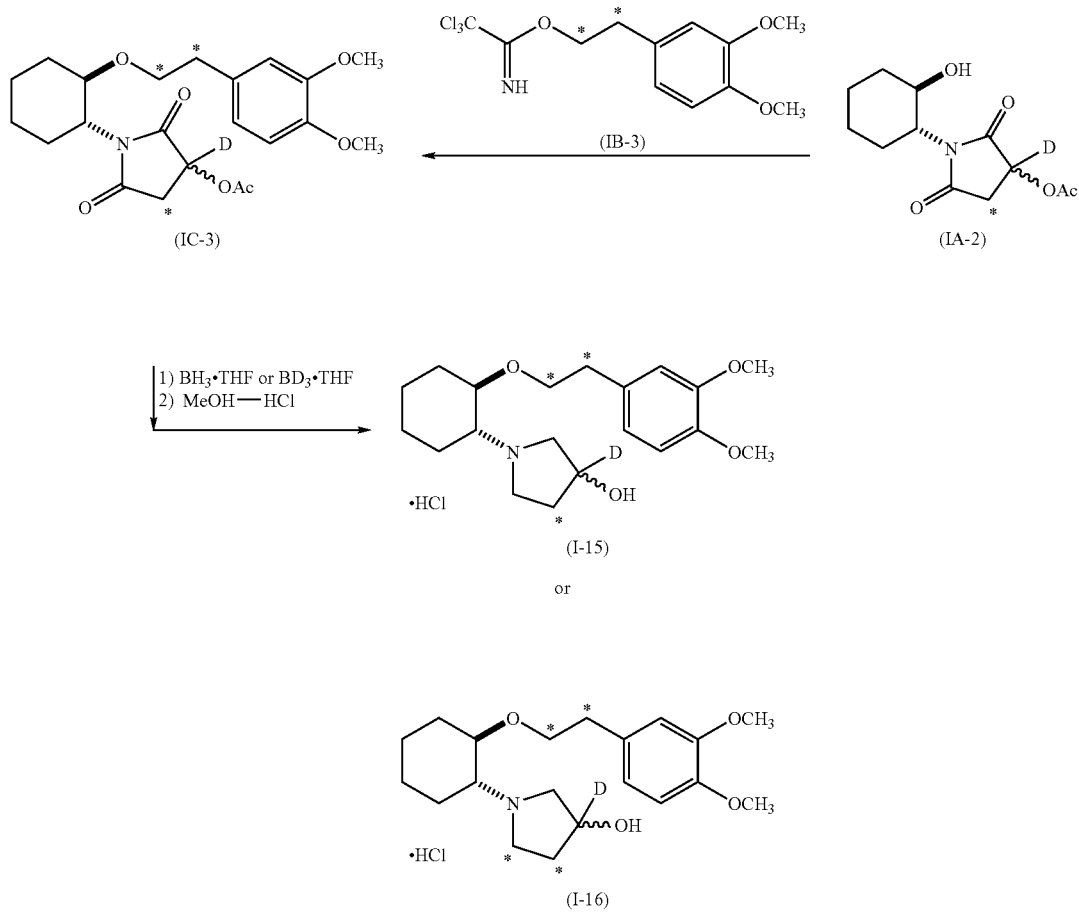

\* = D$_2$

The compound of formula (IZ) is commercially available, for example, from CDN Isotope, or can be prepared by methods known to one skilled in the art. The compound of formula (IB-3) can be prepared according to methods disclosed herein. Deuterated borane is also commercially available, for example, from Cambridge Isotope Laboratories.

In general, the compound of formula (IZ) is treated with a C$_2$-C$_5$ acyl chloride according to the procedures described in Henrot, S. et al., *Synthetic Communications* (1986), Vol. 16, No. 2, pp. 183-190 to form a compound of formula (IAA). The compound of formula (IAA) is condensed with trans-2-(benzyloxy)cyclohexanamine in a suitable solvent, preferably dichloromethane, to form a compound of formula (IBB). The compound of formula (IBB) is subjected to standard hydrogenolysis condition (Pd/C, H$_2$ in a suitable solvent, such as toluene, methanol, ethyl acetate, Ra—Ni—H$_2$, Pt/C—H$_2$) at ambient temperature to remove the benzyl group to give compound of formula (IA-2). Etherification of compound of formula (IA-2) with compound of formula (IB-3) under catalytic Lewis acid conditions (e.g., HBF$_4$ etherate or BF$_3$ etherate) gives the corresponding compound of formula (IC-12). Successive reduction of compound of formula (IC-12) with a suitable deuterated reducing agent, for example, deuterated borane, NaBD$_4$/Lewis acid, KBD$_4$, or lithium aluminum deuteride, provides the compound of formula (I-16). Subsequent treatment with hydrogen chloride in methanol under standard conditions gives the hydrochloride salt of the compound of formula (I-16).

Alternatively, successive reduction of compound of formula (IC-12) with a suitable reducing agent, for example, borane, NaBH$_4$/Lewis acid, KBH$_4$, or lithium aluminum hydride, provides the compound of formula (I-15). Subsequent treatment with hydrogen chloride in methanol under standard conditions gives the hydrochloride salt of the compound of formula (I-15).

In the following Reaction Scheme 12, the compound of formula (I-17) is prepared. The compound of formula (I-17) is a compound of formula (I) wherein R$^1$, R$^2$, R$^3$ and R$^4$ are each deuterium; R$^5$, R$^6$, R$^7$ and R$^8$ are each hydrogen; R$^9$ is methoxy and R$^{10}$ is hydroxy; and R$^{11}$, R$^{12}$ and R$^{13}$ are each hydrogen, and R$^{14}$, R$^{15}$, and R$^{16}$ are each hydrogen:

REACTION SCHEME 12

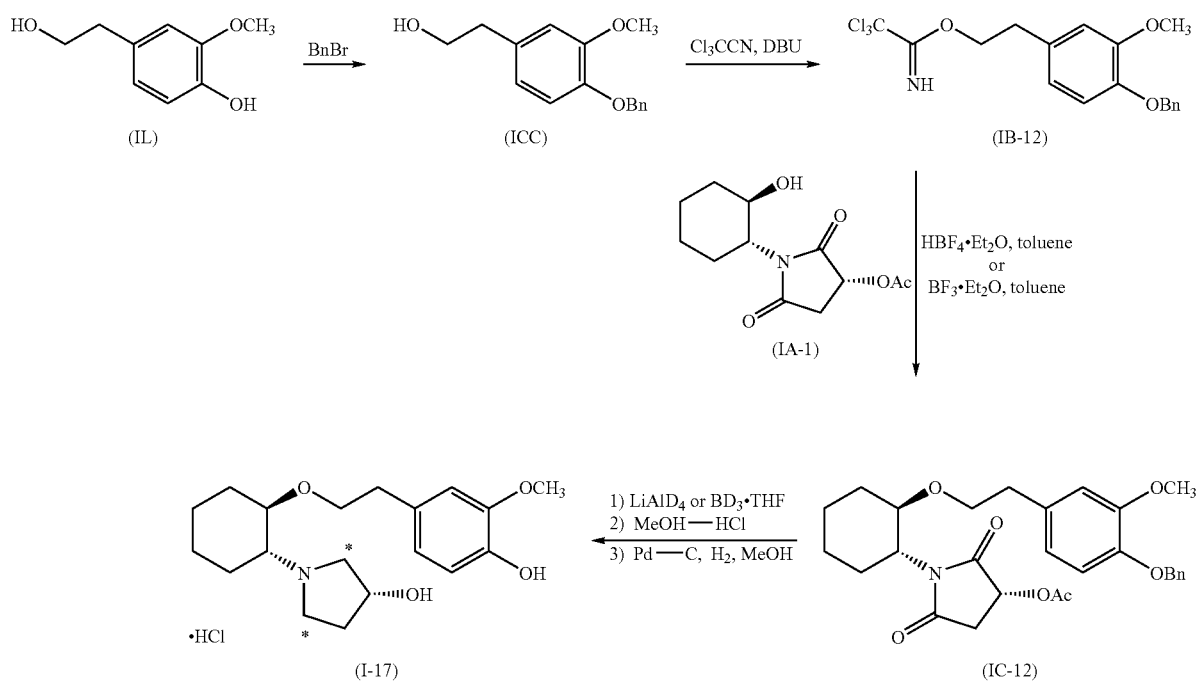

The compound of formula (IL) and benzyl bromide are commercially available, for example, from Aldrich Chemical Co., or can be prepared by methods known to one skilled in the art. Deuterated borane and lithium aluminum deuteride are commercially available, for example, from Cambridge Isotope Laboratories. The compound of formula (IA-1) can be prepared by methods disclosed herein.

In general for the preparation of the compound of formula (I-17), the compound of formula (IL) is treated with benzyl bromide under standard aromatic nucleophilic substitution conditions to form the compound of formula (ICC). The compound of formula (ICC) is then treated with trichloracetonitrile in the presence of a catalyst, preferably DBU, in an aprotic solvent to form the compound of formula (IB-12). Etherification of the compounds of formula (IB-12) with the compound of formula (IA-1) under catalytic Lewis acid conditions (e.g., $HBF_4$ etherate or $BF_3$ etherate in an aprotic solvent, such as toluene) gives the corresponding imido-ether compound of formula (IC-12). Reduction of the compound of formula (IC-12) with a suitable deuterated reducing agent, for example, deuterated borane, $NaBD_4$/Lewis acid, $KBD_4$ or lithium aluminum deuteride, in an aprotic solvent, such as tetrahydrofuran, followed by workup with methanolic hydrochloride and hydrogenation over Pd—C in methanol provides the hydrochloride salt of the compound of formula (I-17).

In the following Reaction Scheme 13, the compound of formula (I-18) is prepared. The compound of formula (I-18) is a compound of formula (II) wherein $R^1$, $R^2$, $R^3$ and $R^4$ are each deuterium; $R^5$ and $R^6$ are each deuterium; $R^7$ and $R^8$ are each hydrogen; $R^9$ is methoxy and $R^{10}$ is hydroxy; and $R^{11}$, $R^{12}$ and $R^{13}$ are each hydrogen, and $R^{14}$, $R^{15}$, and $R^{16}$ are each hydrogen:

REACTION SCHEME 13

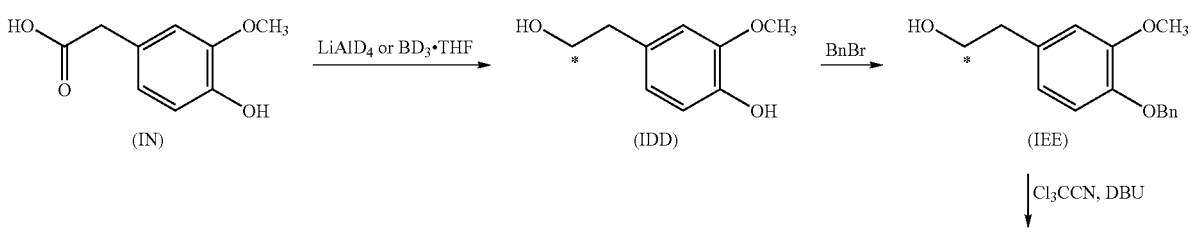

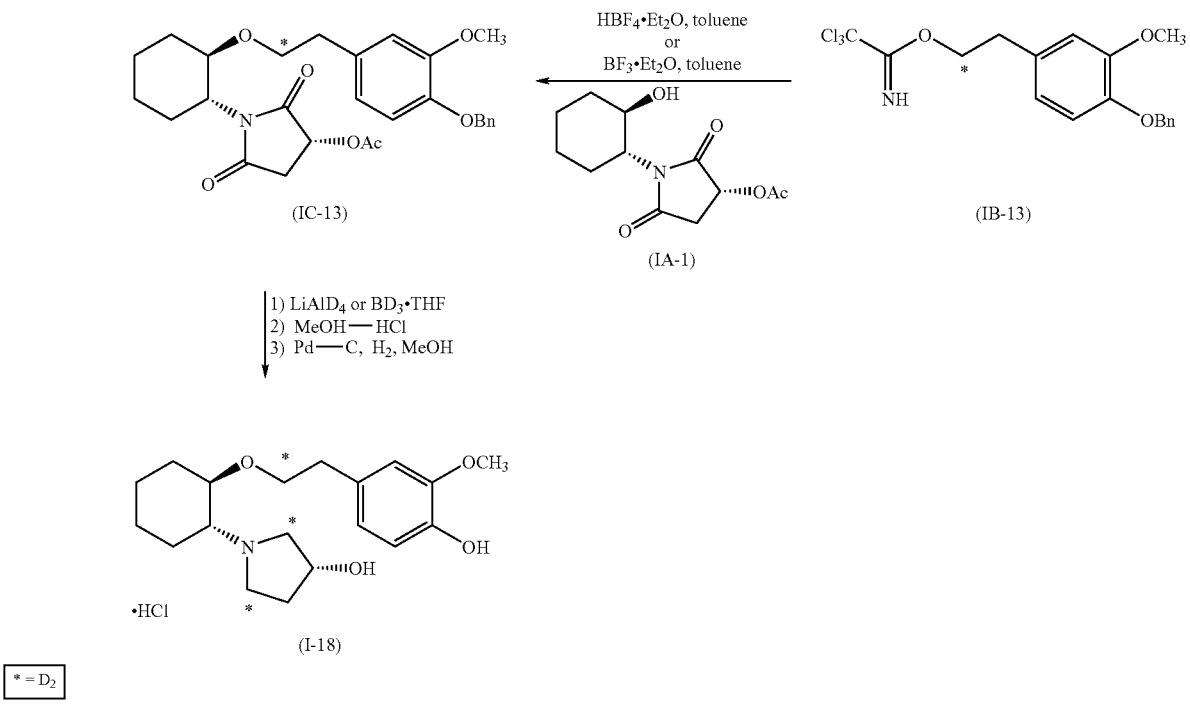

The compound of formula (IN) and benzyl bromide is commercially available, for example, from Aldrich Chemical Co, or can be prepared by methods known to one skilled in the art. Deuterated borane and lithium aluminum deuteride are commercially available, for example, from Cambridge Isotope Laboratories. The compound of formula (IA-1) can be prepared by methods disclosed herein.

In general for the preparation of the compound of formula (I-18), the compound of formula (IN) is reduced with a reducing agent, such as lithium aluminum deuteride or deuterated borate, under standard reducing conditions, for example, in the presence of an aprotic solvent, such as tetrahydrofuran, to yield a compound of formula (IDD). The compound of formula (IDD) is then treated with benzyl bromide under standard aromatic nucleophilic substitution conditions to produce the compound of formula (IEE). The compound of formula (IEE) is then treated with trichloracetonitrile in the presence of a catalyst, preferably DBU, in an aprotic solvent to form the compound of formula (IB-13). Etherification of the compounds of formula (B-13) with the compound of formula (IA-1) under catalytic Lewis acid conditions (e.g., $HBF_4$ etherate or $BF_3$ etherate in an aprotic solvent, such as toluene) gives the corresponding imido-ether compound of formula (IC-13). Reduction of the compound of formula (IC-13) with a suitable deuterated reducing agent, for example, deuterated borane, $NaBD_4$/Lewis acid, $KBD_4$ or lithium aluminum deuteride, in an aprotic solvent, such as tetrahydrofuran, followed by workup with methanolic hydrochloride and hydrogenation over Pd—C in methanol provides the hydrochloride salt of the compound of formula (I-18).

In the following Reaction Scheme 14, the compound of formula (I-19) and the compound of formula (I-20) are prepared. The compound of formula (I-19) is a compound of formula (I) wherein $R^1$, $R^2$, $R^3$ and $R^4$ are each hydrogen; $R^5$, $R^6$, $R^7$ and $R^8$ are each deuterium; $R^9$ is methoxy and $R^{10}$ is hydroxy; and $R^{11}$, $R^{12}$ and $R^{13}$ are each hydrogen. The compound of formula (I-20) is a compound of formula (I) wherein $R^1$, $R^2$, $R^3$ and $R^4$ are each deuterium; $R^5$, $R^6$, $R^7$ and $R^8$ are each deuterium; $R^9$ is methoxy and $R^{10}$ is hydroxy; and $R^{11}$, $R^{12}$ and $R^{13}$ are each hydrogen, and $R^{14}$, $R^{15}$, and $R^{16}$ are each hydrogen:

REACTION SCHEME 14

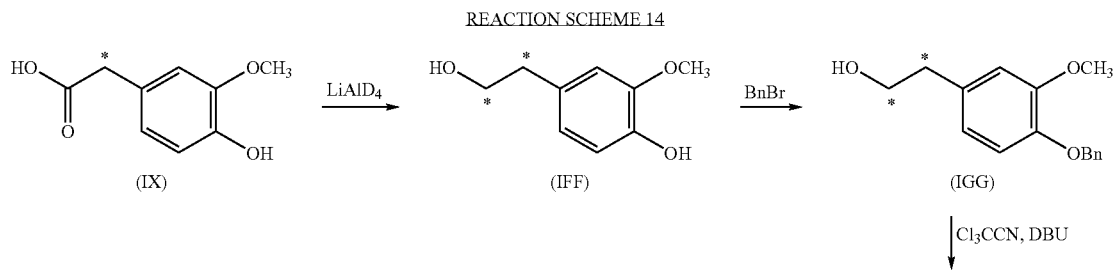

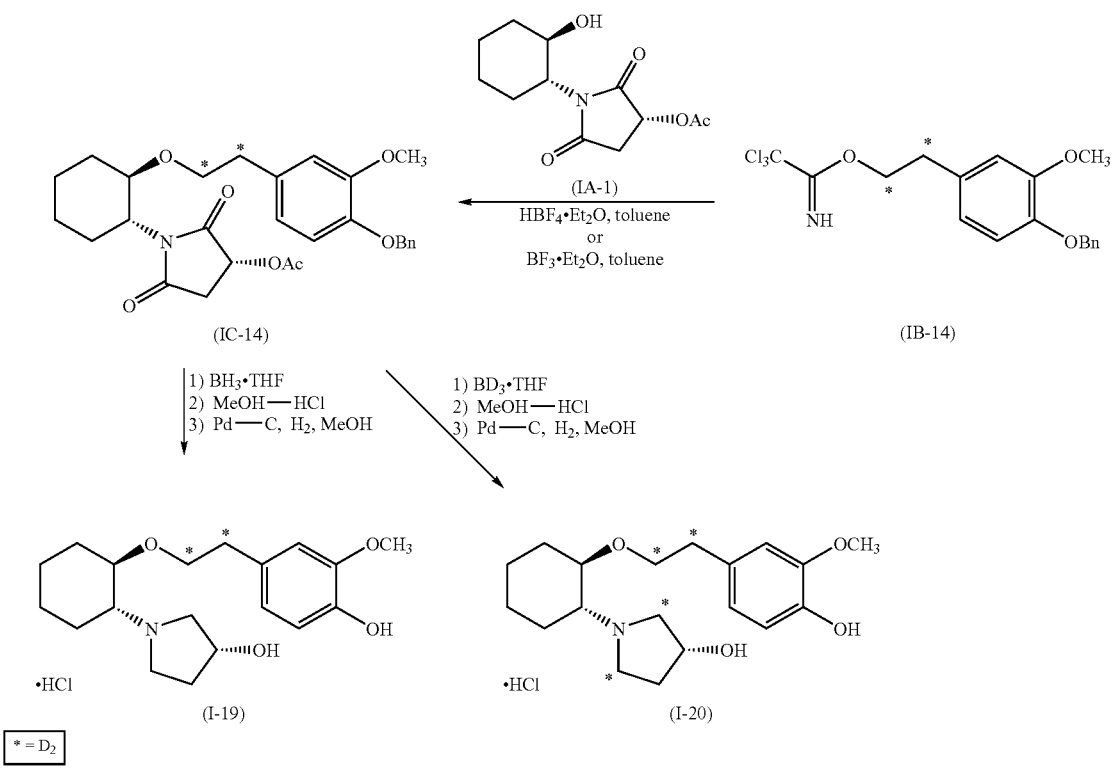

The compound of formula (IX) is commercially available, for example, from CDN Isotope, or can be prepared by methods known to one skilled in the art. Benzyl bromide is commercially available, for example, from Aldrich Chemical Co., or can be prepared according to methods known to one skilled in the art. Deuterated borane and lithium aluminum deuteride are commercially available, for example, from Cambridge Isotope Laboratories. The compound of formula (IA-1) can be prepared by methods disclosed herein.

In general for the preparation of the compound of formula (I-19), the compound of formula (IX) is reduced with a reducing agent, such as lithium aluminum deuteride, in the presence of an aprotic solvent to yield a compound of formula (IFF). The compound of formula (IFF) is then treated with benzyl bromide under standard aromatic nucleophilic substitution conditions to produce the compound of formula (IGG). The compound of formula (IGG) is then treated with trichloracetonitrile in the presence of a catalyst, preferably DBU, in an aprotic solvent to form the compound of formula (B-14).

Etherification of the compounds of formula (IB-14) with the compound of formula (IA-1) under catalytic Lewis acid conditions (e.g., $HBF_4$ etherate or $BF_3$ etherate in an aprotic solvent, such as toluene) gives the corresponding imido-ether compound of formula (IC-14). Reduction of the compound of formula (IC-14) with a suitable deuterated reducing agent, for example, deuterated borane, in an aprotic solvent, such as tetrahydrofuran, followed by workup with methanolic hydrochloride and hydrogenation over Pd—C in methanol provides the hydrochloride salt of the compound of formula (I-20).

Alternatively, the compound of formula (IC-14) is reduced with a suitable reducing agent, for example, borane, in an aprotic solvent, such as tetrahydrofuran, followed by workup with methanolic hydrochloride and hydrogenation over Pd—C in methanol to provide the hydrochloride salt of the compound of formula (I-19).

Alternatively, in the following Reaction Scheme 15, the compound of formula (I-19) and the compound of formula (I-20), as defined above in Reaction Scheme 14, are prepared:

REACTION SCHEME 15

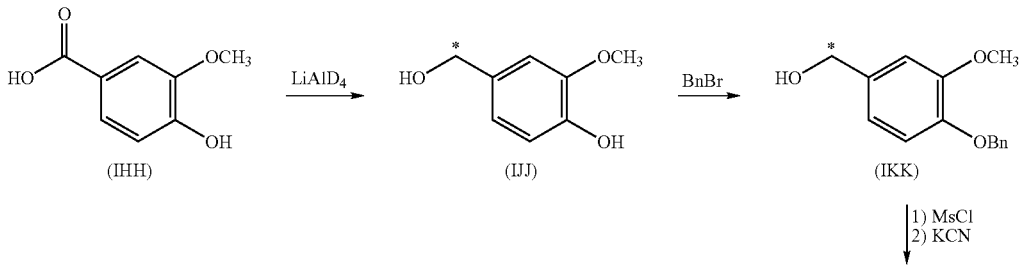

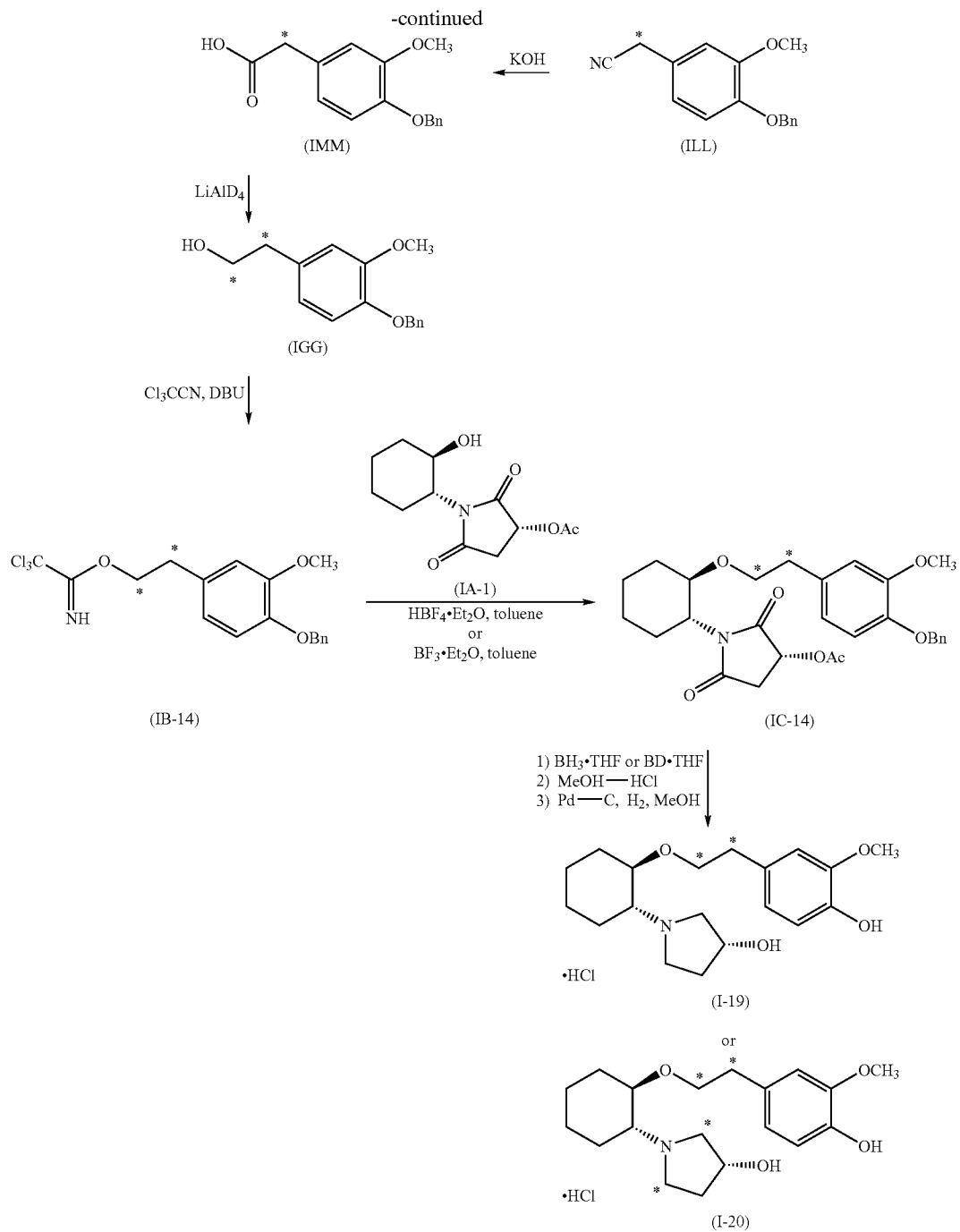

* = D₂

The compound of formula (IHH) is commercially available, for example, from Aldrich Chemical Co., or can be prepared by methods known to one skilled in the art. Benzyl bromide is commercially available, for example, from Aldrich Chemical Co., or can be prepared according to methods known to one skilled in the art. Deuterated borane and lithium aluminum deuteride are commercially available, for example, from Cambridge Isotope Laboratories. The compound of formula (IA-1) can be prepared by methods disclosed herein.

In general for the preparation of the compound of formula (I-19), the compound of formula (IHH) is reduced with a deuterated reducing agent, such as lithium aluminum deuteride, in the presence of an aprotic solvent to yield a compound of formula (IJJ). The compound of formula (IJJ) is then treated with benzyl bromide under standard aromatic nucleophilic substitution conditions to produce the compound of formula (IK). The compound of formula (IKK) is then reacted with mesylate chloride under standard mesylation conditions to form the mesylate intermediate, which is then treated with potassium cyanide under standard nucleophilic substitution conditions to form the compound of formula (ILL). The compound of formula (ILL) is then hydrolyzed under standard hydrolysis conditions, such as treatment with potassium hydroxide, to form the compound of formula (IMM). The compound of formula (IMM) is then reduced with a deuterated reducing agent, such as lithium aluminum deuteride, in the presence of an aprotic solvent to yield a compound of formula (IGG). The compound of formula (IGG) is then treated with trichloracetonitrile in the presence of a catalyst, preferably DBU, in an aprotic solvent to form the compound of formula (IB-14). Etherification of the compounds of formula (IB-14) with the compound of formula (A-1) under catalytic Lewis acid conditions (e.g., HBF$_4$ etherate or BF$_3$ etherate in an aprotic solvent, such as toluene) gives the corresponding imido-ether compound of formula (C-14). Reduction of the compound of formula (IC-14) with a suitable deuterated reducing agent, for example, deuterated borane, in an aprotic solvent, such as tetrahydrofuran, followed by workup with methanolic hydrochloride and hydrogenation over Pd—C in methanol provides the hydrochloride salt of the compound of formula (I-20). Alternatively, the compound of formula (IC-14) is reduced with a suitable reducing agent, for example, borane, in an aprotic solvent, such as tetrahydrofuran, followed by workup with methanolic hydrochloride and hydrogenation over Pd—C in methanol to provide the hydrochloride salt of the compound of formula (I-19).

In the following Reaction Scheme 16, the compound of formula (I-21) is prepared. The compound of formula (I-21) is a compound of formula (I) wherein $R^1$, $R^2$, $R^3$ and $R^4$ are each deuterium; $R^5$ and $R^6$ are each deuterium, $R^7$ and $R^8$ are each hydrogen; $R^9$ is hydroxy and $R^{10}$ is methoxy; and $R^{11}$, $R^{12}$ and $R^{13}$ are each hydrogen, and $R^{14}$, $R^{15}$, and $R^{16}$ are each hydrogen:

The compound of formula (IQ) is commercially available, for example, from Aldrich Chemical Co, or can be prepared by methods known to one skilled in the art. Benzyl bromide is commercially available, for example, from Aldrich Chemical Co., or can be prepared according to methods known to one skilled in the art. Deuterated borane and lithium aluminum deuteride are commercially available, for example, from Cambridge Isotope Laboratories. The compound of formula (IA-1) can be prepared by methods disclosed herein.

In general for the preparation of the compound of formula (I-21), the compound of formula (IQ) is reduced with a reducing agent, such as lithium aluminum deuteride or deuterated borane, in the presence of an aprotic solvent, such as tetrahydrofuran, to yield a compound of formula (IOO). The compound of formula (IOO) is then treated with benzyl bromide under standard aromatic nucleophilic substitution conditions to produce the compound of formula (IPP). The compound of formula (IPP) is then treated with trichloracetonitrile in the presence of a catalyst, preferably DBU, in an aprotic solvent to form the compound of formula (IB-15). Etherification of the compounds of formula (IB-15) with the compound of formula (IA-1) under catalytic Lewis acid conditions (e.g., HBF$_4$ etherate or BF$_3$ etherate in an aprotic solvent, such as toluene) gives the corresponding imido-ether compound of formula (IC-15). Reduction of the compound of formula (IC-15) with a suitable deuterated reducing agent, for example, deuterated borane or lithium aluminum deuteride, in an aprotic solvent, such as tetrahydrofuran, followed by workup with methanolic hydrochloride and hydrogenation over Pd—C in methanol provides the hydrochloride salt of the compound of formula (I-21).

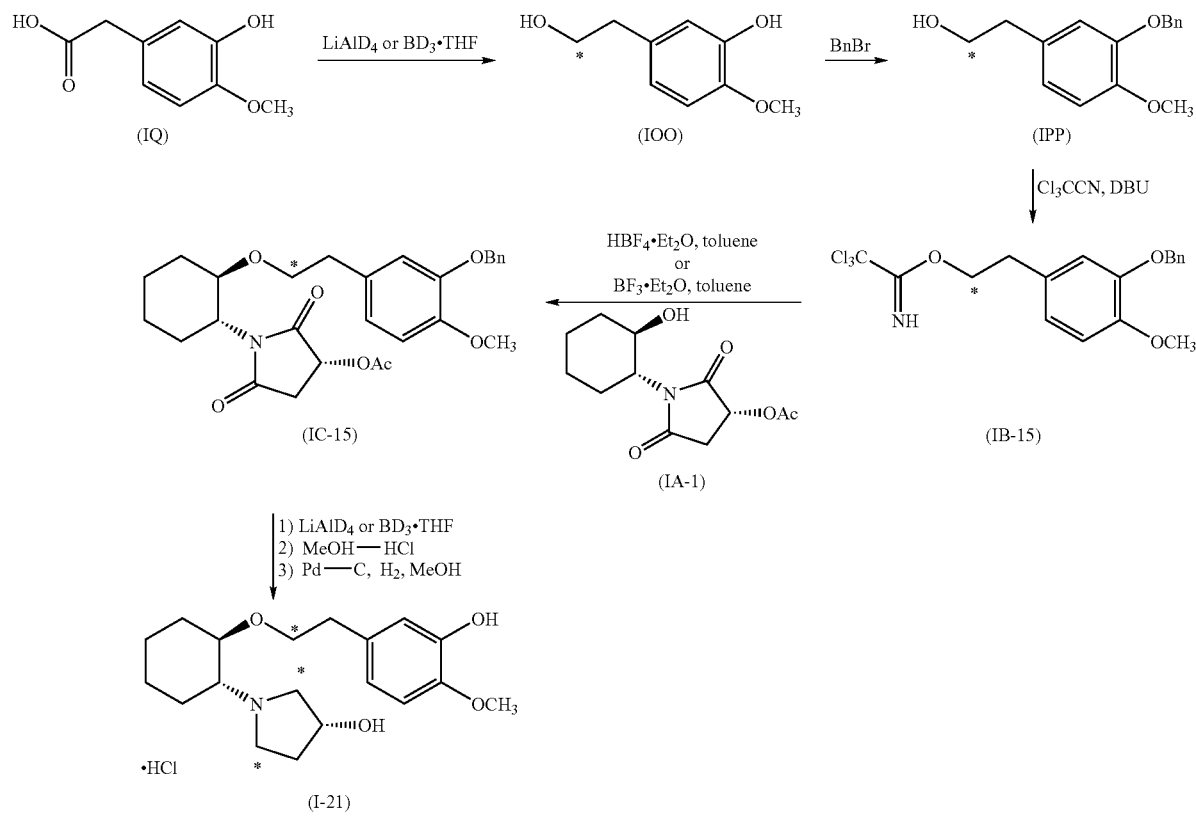

In the following Reaction Scheme 16a, the compound of formula (I-22) is prepared. The compound of formula (I-22) is a compound of formula (I) wherein $R^1$, $R^2$, $R^3$, $R^4$, $R^5$, $R^6$, $R^7$, $R^8$, $R^{11}$, $R^{12}$, $R^{13}$ are all hydrogen; $R^9$ and $R^{10}$ are both methoxy; and $R^{14}$, $R^{15}$ and $R^{16}$ are each deuterium:

REACTION SCHEME 16A

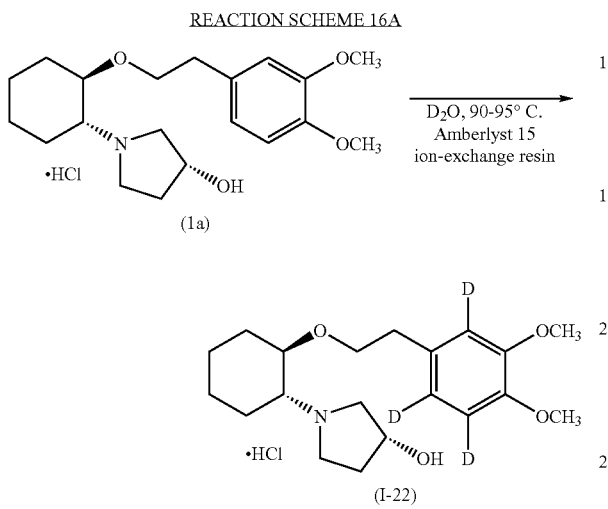

The compound of formula (Ia) is a compound of formula (1), as defined herein, and is prepared according to the methods disclosed in PCT Published Patent Application, WO 2004/099137.

In general, Compound (1-22) was synthesized according to Reaction Scheme 16a using the procedure of Tuck et al. (K. L. Tuck, Tan, H-W, Hayball, P. J.; J. *Labelled Cpd. Radiopharma.* 2000, 43, 817-823), as described in more detail below in Example 5A below.

It is understood that any of the compounds of formula (I) prepared above in Reaction Schemes 1-16 can be used as the starting material in the above Reaction Scheme 16a to produce the corresponding compounds of formula (I-22) wherein the phenyl ring is deuterated.

In addition to the above Reaction Schemes, compounds of formula (I) wherein $R^1$ and $R^2$ are both hydrogen and $R^3$ and $R^4$ are both deuterium or compounds of formula (I) wherein $R^1$ and $R^2$ are both deuterium and $R^3$ and $R^4$ are both hydrogen can be prepared by treating the appropriate compound of formula (C) with a reducing agent under mild conditions to form the following intermediate compounds:

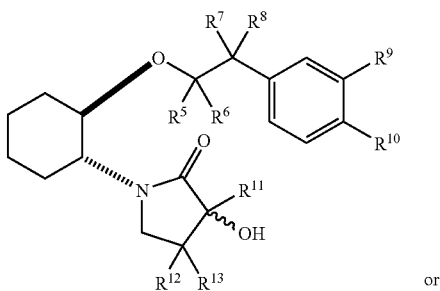

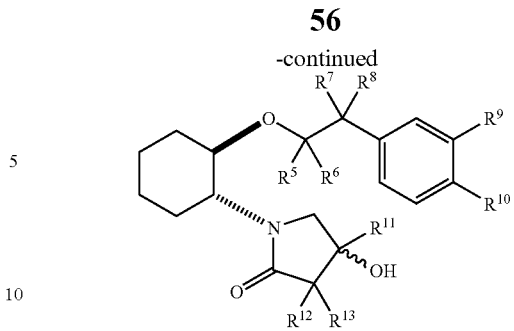

where $R^5$, $R^6$, $R^7$, $R^8$, $R^9$, $R^{10}$, $R^{11}$, $R^{12}$, and $R^{13}$ are as defined above for compounds of formula (I), which can then be treated with a deuterated reducing agent under mild conditions to prepare compounds of formula (I) wherein $R^1$ and $R^2$ are both hydrogen and $R^3$ and $R^4$ are both deuterium or compounds of formula (I) wherein $R^1$ and $R^2$ are both deuterium and $R^3$ and $R^4$ are both hydrogen. Alternatively, the appropriate compound of formula (C) can be first treated with a deuterated reducing agent under mild conditions to form the following intermediate compounds:

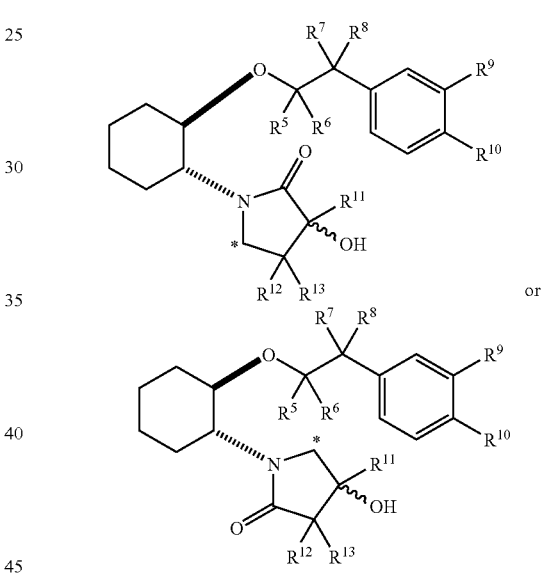

where $R^5$, $R^6$, $R^7$, $R^8$, $R^9$, $R^{10}$, $R^{11}$, $R^{12}$ and $R^{13}$ are as defined above for compounds of formula (I), which can then be treated with a reducing agent under mild conditions to prepare compounds of formula (I) wherein $R^1$ and $R^2$ are both hydrogen and $R^3$ and $R^4$ are both deuterium or compounds of formula (I) wherein $R^1$ and $R^2$ are both deuterium and $R^3$ and $R^4$ are both hydrogen.

B. Preparation of Compounds of Formula (II)

In the following Reaction Scheme 17 compounds of formula (II) are illustrated as being prepared. It is understood that the specific stereoisomers of compounds of formula (II) can be prepared in a similar fashion utilizing the appropriately substituted chiral starting material. The present invention also encompasses the preparation of the pharmaceutically acceptable salts of the compounds of formula (II).

In general, compounds of formula (II), as set forth above in the Summary of the Invention, can be prepared by the method disclosed in Reaction Scheme 17 wherein $R^1$, $R^2$, $R^3$, $R^4$, $R^5$, $R^6$, $R^7$, $R^8$, $R^9$, $R^{10}$, $R^{11}$ and $R^{12}$ are as described above in the Summary of the Invention for compounds of formula (II), R is $C_2$-$C_5$acyl and Q is a leaving group, preferably trihaloacetimidate:

REACTION SCHEME 17

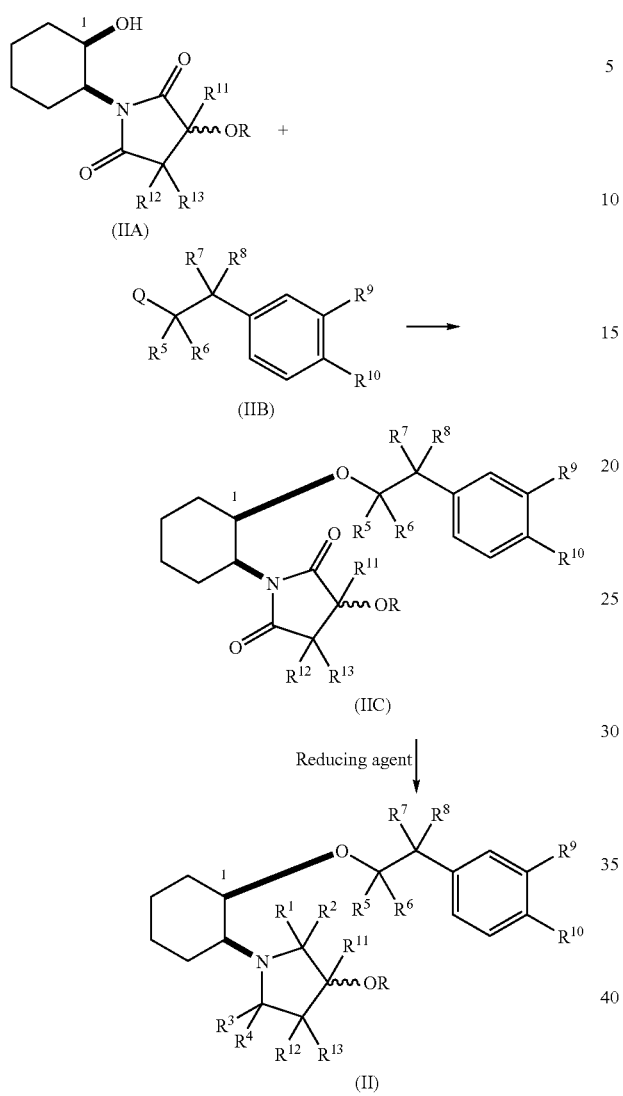

Compounds of formula (IIA) and compounds of formula (IIB) can be prepared by methods known to one skilled in the art or by methods disclosed herein or can be obtained commercially.

Compounds of formula (II) are prepared as illustrated above in Reaction Scheme 17 by first treating a compound of formula (IIA) with a compound of formula (IIB) under suitable etherification conditions such that upon reaction of the compound of formula (IIA) with the compound of formula (IIB), the stereochemical configuration of the carbon at the 1-position of the compound of formula (IIA) is retained in the resulting compound of formula (IIC). Preferably, such suitable conditions are catalytic Lewis acid conditions (e.g., $HBF_4$ etherate or $BF_3$ etherate). The compound of formula (IIC) is then reduced with a suitable deuterated or non-deuterated reducing agent to yield a compound of formula (II). Salts of the compound of formula (II) can be prepared by standard methods.

Compounds of formula (IIA) can be prepared as illustrated below in Reaction Scheme 17A wherein PG is an oxygen-protecting group, preferably optionally substituted benzyl; $R^2$ is selected to form a compound of formula (IIF) upon treatment with the compound of formula (IID), followed by cyclization, and is selected, but is not limited to, from the following radicals wherein the ∼∼∼ line in the following represents the ∼∼∼ bond between $R^2$ and the OR group in compounds of formula (IIE):

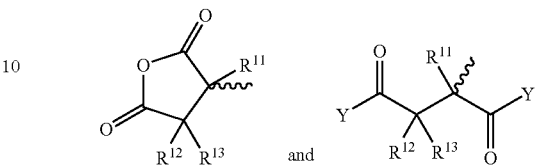

where each Y is halo; R is H, $C_2$-$C_5$acyl or an oxygen-protecting group; and $R^{11}$, $R^{12}$ and $R^{13}$ are as defined above in the Summary of the Invention for the compounds of formula (II):

REACTION SCHEME 17A

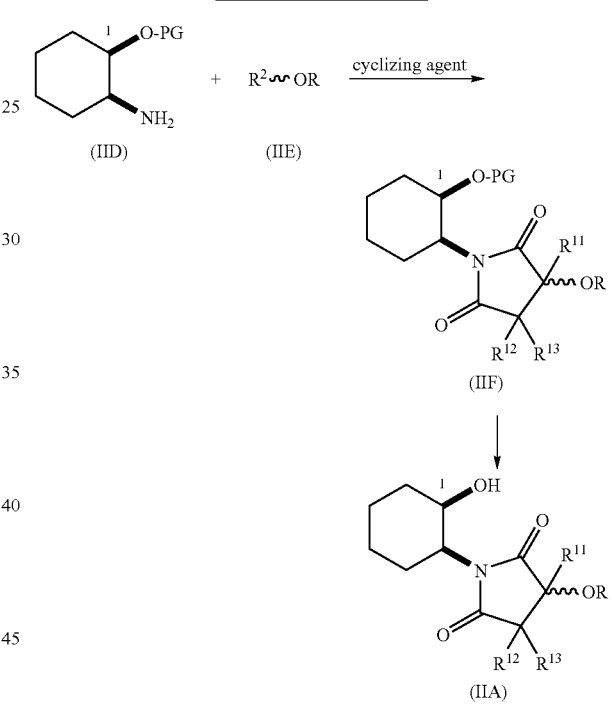

In general, the compounds of formula (IIA) are prepared in Reaction Scheme 17A by first treating a compound of formula (IID) with a compound of formula (11E) in an aprotic solvent, such as toluene, dichloromethane, or ethyl acetate, followed by the treatment with an cyclizing agent, such as a $C_2$-$C_5$acyl halide or $C_2$-$C_5$acyl anhydride, at temperatures of between about 0° C. to reflux temperature, preferably at reflux temperature, to form a compound of formula (IIF). Alternatively, a compound of formula (IID) is first treated with a compound of formula (11E) in an aprotic solvent to yield a corresponding intermediate, which is then treated with a cyclizing agent to form compounds of formula (IIF). Compounds of formula (IIF) are then subjected to standard deprotection conditions known to one skilled in the art, such as hydrogenation in the presence of a catalyst under appropriate conditions, to form the compound of formula (IIA), which is isolated from the reaction mixture by standard isolation techniques.

The compounds of formula (II) can be prepared according to methods similar to those described above in Reaction Schemes 2-16 using the appropriate chiral starting material or chiral reagent. In particular, compounds of formula (II) having the following cis stereochemistry at positions 1 and 2 of the cyclohexyl ring may be prepared:

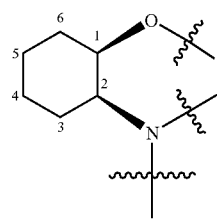

It is understood, however, that compounds of formula (II) having the following stereochemistry at positions 1 and 2 of the cyclohexyl ring:

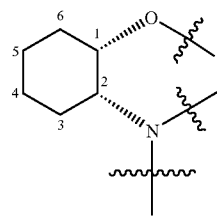

can be prepared in a similar manner using the appropriate chiral starting material or chiral reagent.

The invention is further defined by reference to the following Synthetic Examples and Biological Examples, which describe the preparation of several exemplary embodiments of the compounds described herein and methods for their use. It will be apparent to the skilled artisan that many modifications, both to the materials and methods, may be practiced without departing from the scope of the invention.

SYNTHETIC EXAMPLE 1

PREPARATION OF (1R,2R)/(1S,2S)-2-[(3R)-HYDROXYPYRROLIDINYL]-1-(3-METHOXY-4-$D_3$-METHOXYPHENETHOXY CYCLOHEXANE

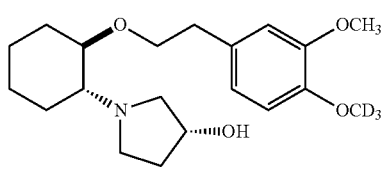

A. Homo vanillyl alcohol (1.0 g, 5.95 mmol) was dissolved in anhydrous DME (25 mL) followed by the addition of cesium carbonate (3.87 g, 11.89 mmol). The mixture was stirred under argon for 1h and deuterium iodomethane (1.29 g, 8.92 mmol, 555 µL) was added. The reaction mixture was refluxed for 2.5 h and concentrated. The residue dissolved in ethyl acetate and washed with sat. NaHCO₃, water and dried over MgSO₄, filtered, concentrated to give a light yellow oil (1.03 g, 93%); ¹H NMR (300 MHz, CDCl₃): δ6.82-6.74 (m, 3H, aromatic), 3.86 (s, 3H, OCH₃), 3.82 (t, 2H), 2.79 (t, 2H), 1.47 (s, 1 H).

B. To an oven dried round bottom flask (100 mL) charged with argon and cooled was added NaH (197 mg, 8.2 mmol). A solution of the yellow oil (690 mg, 4.09 mmol) in anhydrous DME (20 mL) was added slowly to the reaction mixture and stirred for 1 h, then a solution of (1R,2R)/(1S,2S)-1-[(3R)-benzyloxypyrrolidinyl]-2-chlorocyclohexane (1.0 g, 3.41 mmol) in DME (20 mL) was added and the resultant mixture was heated to 80-85° C. for 18 h. To the cooled mixture was added, 2M NaHCO₃ (10 mL), water (30 mL) and ethyl acetate (40 mL). The organic layer was collected and washed with brine, dried over MgSO₄ and concentrated in vacuo to give (1R,2R)/(1S,2S)-2-[(3R)-Benzyloxypyrrolidinyl-1-(3-methoxy-4-d₃-methoxyphenethoxy)cyclohexane (1.4 g, 93% yield).

C. To a solution of (1R,2R)/(1S,2S)-2-[(3R)-Benzyloxypyrrolidinyl-1-(3-methoxy-4-d₃-methoxyphenethoxy)cyclohexane (1.3 g, 2.94 mmol) in absolute ethanol (40 mL) was added palladium, 10 wt. % activated carbon (520 mg), 6M HCl (2 mL). The resultant reaction mixture was stirred for 18 h under a positive hydrogen atmosphere. The reaction mixture was filtered through celite 545 and concentrated to give 1.06 g of (1R,2R)/(1S,2S)-2-[(3R)-Hydroxypyrrolidinyl-1-(3-methoxy-4-d₃-methoxyphenethoxy)cyclohexane (92.6%); ¹H NMR (300 MHz, DMSO-d₆) δ10.9-10.34 (m, 1H, NH), 6.86-6.73 (m, 3H), 5.49 (s, 1H), 4.33 (s, 1H), 4 (q, 1H), 3.73 (s, 3H, OCH₃), 3.57-3.02 (m, 6H), 2.78 (d, 2H, J 5.06), 2.18-1.62 (m, 6H), 1.39-1.05 (m, 4H); MS (ES+) [M +H]⁺353.10.

SYNTHETIC EXAMPLE 2

PREPARATION OF (1R,2R)/(1S,2S)-2- [(3R)-HYDROXYPYRROLIDINYL]-1-(3,4-DI-D₃-METHOXYPHENETHOXY)CYCLOHEXANE

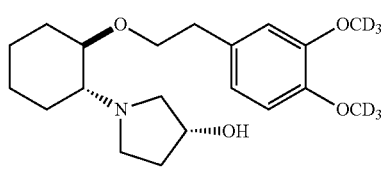

Following the same synthetic methodology as described above in Example 1, except that 3,4-dihydroxyphenethyl alcohol is used as the starting material, (1R,2R)/(1S,2S)-2-[(3R) -hydroxypyrrolidinyl]-1-(3,4-di-d₃-methoxyphenethoxy)cyclonehexane was prepared: ¹H NMR (300 MHz, CDCl₃) δ6.77-6.74 (m, 3H), 4.21-4.16 (m, 1H), 3.83-3.67 (m, 1H), 3.58-3.50 (m, 1H), 3.04-2.90 (m, 1H), 2.83-2.77 (m, 3H), 2.71-2.60 (m, 1H), 2.50-2.42 (m, 2H), 2.05-1.84 (m, 3H), 1.72-1.60 (m, 3H), 1.37-1.19 (m, 4H); ¹³C NMR (300 MHz, CDCl₃) δ148.70 (+), 147.40 (+), 131.80 (+), 120.71 (−), 112.36 (−), 111.16 (−), 79.28/79.14 (−), 70.92/70.59 (−), 69.59/69.47 (+), 63.80/63.69 (−), 59.78/59.58 (+), 50.62 (−), 49.07/48.70 (+), 36.34 (+), 34.29/34.08 (+), 29.13 (+), 27.26/27.18 (+), 23.54 (+), 23.05 (+); MS (ES+) [M+H]⁺356.2.

SYNTHETIC EXAMPLE 3

PREPARATION OF (1R,2R)-2-[(3R)-HYDROXY-2,2,5,5-D₄-PYRROLIDINYL]-1-(3,4-DIMETHOXYPHENETHOXY)CYCLOHEXANE

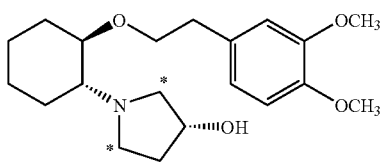

(1R,2R)-2-[(3R)-Hydroxy-2,2,5,5-d₄-pyrrolidinyl]-1-(3,4-dimethoxyphenethoxy)cyclohexane was prepared by adding 476 mL of a solution of 1M BD₃.THF via an additional funnel under nitrogen over a period of 30 mins to a cooled solution (0° C.) of (1R,2R)-2-[(3R)-2,5-dioxo-3-acetoxypyrrolidinyl]-1-(3,4-dimethoxyphenethoxy)cyclohexane (57 g) in of anhydrous THF (200 mL). The reaction mixture was heated to 70° C.-75° C. (oil bath temperature) under nitrogen and stirred for 2 hours. The reaction mixture was cooled to 0° C. To the cooled solution, MeOH was slowly added over a period of 15 minutes and concentrated to remove solvent to a volume of approximately 150 mL. MeOH—HCl (380 mL) was added via addition funnel over a period of 15 min and then heated to 70° C.-75° C. (oil bath temperature) for 1 hour. The reaction mixture was then cooled to ambient temperature and concentrated under reduced pressure to provide of (1R,2R)-2-[(3R)-hydroxy-2,2,5,5-d₄-pyrrolidinyl]-1-(3,4-dimethoxyphenethoxy)cyclohexane hydrochloride (54 g).

SYNTHETIC EXAMPLE 4

PREPARATION OF (1R,2R)-1(2-[2-(4-BENZYLOXY-3-METHOXYPHENYL)ETHOXY]CYCLOHEXYL)-(3R)-2,2,5,5-D₄-PYRROLIDINYL-3-OL

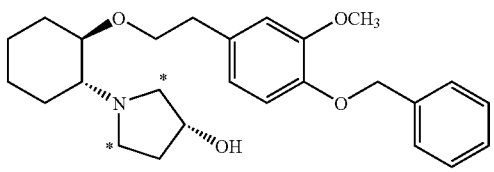

BD₃.THF (459 mL) was added via addition funnel under nitrogen over a period of 45 minutes to a 0° C. solution of (1R,2R)-2-[(3R)-2,5-dioxo-3-Acetoxypyrrolidinyl]-1-(3-methoxy-4-ophenethoxy)cyclohexane (65 g) in anhydrous THF (220 mL). The reactrion mixture was heated to 70° C.-75° C. (oil bath temperature) under nitrogen for 1 hour. The reaction mixture was then cooled to 0° C. and MeOH (50 mL) was added dropwise over a period of 30 minutes. The resultant reaction mixture was concentrated to a volume of approximately 150 mL to remove solvents. A solution of MeOH—HCl (370 mL) was added dropwise to the concentrated solution at 0° C. over a period of 30 min. The resulting reaction mixture was heated to reflux at 70° C.-75° C. for 1 hour and then allowed to cool to ambient temperature. The ambient temperature mixture was concentrated under reduced pressure to provide (1R,2R)-[(242-(4-benzyloxy-3-methoxyphenyl)ethoxy]cyclohexyl)-(3R)-2,2,5,5-d₄-pyrrolidin-3-ol hydrochloride (61.13 g).

SYNTHETIC EXAMPLE 5

PREPARATION OF (1R,2R)-2-[(3R)-HYDROXY-2,2,5,5-D₄-PYRROLIDINYL]-1-(3-METHOXY-4-HYDROXYPHENETHOXY)CYCLOHEXANE

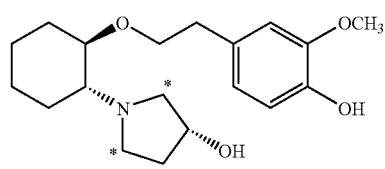

(1R,2R)-[(242-(4-benzyloxy-3-methoxyphenyl)ethoxy] cyclohexyl)-(3R)-2,2,5,5-d₄-pyrrolidin-3-ol (57 g) was dissolved in MeOH (250 mL). To the solution was added 5.7 g of Pd/C (loading 10% wt. supported activated carbon) in small portions while maintaining a nitrogen atmosphere throughout the reaction mixture. Using a Parr hydrogenator, a parr bottle containing the reaction mixture was evacuated and backfilled with hydrogen gas and repeated four times. Hydrogen pressure (60 psi) was then applied and the reaction vessel was shaken for 18 hours at ambient temperature. The reaction mixture was then filtered through a Celite™ pad with MeOH and the Pd/C was further washed with 50 mL of MeOH. The combined filtrates were concentrated under reduced pressure and then dried in vacuo to (1R,2R)-2-[(3R)-Hydroxy-2,2,5,5-d₄-pyrrolidinyl]-1-(3-methoxy-4-hydroxyphenethoxy)cyclohexane hydrochloride (45 g).

SYNTHETIC EXAMPLE 5A

PREPARATION OF (1R,2R)-2-[(3R)-HYDROXY-PYRROLIDINYL-1-(3,4-DIMETHOXY-2,5,6-D₃-PHENETHOXY)CYCLOHEXANE

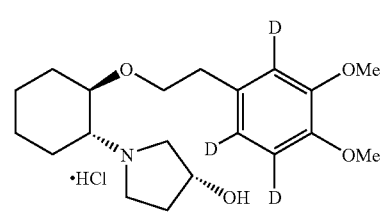

To a solution of (1R,2R)-2-[(3R)-hydroxypyrrolidinyl-1-(3,4-dimethoxyphenethoxy)cyclohexane hydrochloride (0.6 g, 1.6 mmol) in D₂O (2.0 mL, 99% D enrichment) was added Amberlyst 15 ion-exchange resin (0.6 g, Sigma-Aldrich, CAS # 39389-20-3). The mixture was heated in a sealed vessel for 24 h. On completion, the vessel was cooled, and the solution was filtered to remove the resin and washed with H₂O (2×5 mL). To the filtered solution was added a brine solution (15 mL) and the aqueous solution was extracted with CH₂Cl₂ (4×10 mL). The combined organic extracts were dried (MgSO₄), filtered, and concentrated under reduced pressure to obtain a foamy solid (0.5 g), which was further recrystallized from isopropyl alcohol to give (1R,2R)-2-[(3R)-hydroxypyrrolidinyl-1-(3,4-dimethoxy-2,5,6-d₃-phenethoxy)cyclohexane hydrochloride as a white solid (0.4 g). $R_f$=0.51 (1:1, v/v, EtOAc:MeOH with 5% iPrNH₂); MS (ES) Found=351.1 [M]⁺, 352.1 [M]⁺, 353.1 [M]⁺ (ratio~66%:100%:33% by MS).

SYNTHETIC EXAMPLE 6

Compounds of Formula (I)

Using the methods described in the above Reaction Schemes and Synthetic Examples, the following representative compounds of formula (I), where D is deuterium and an asterisk (*) represents a carbon wherein two deuterium atoms are attached, can be prepared:

| # | Compound | Chemical name |
|---|---|---|
| 1 | | (1R,2R/1S,2S)-2-[(3R/3S)-Hydroxy-2,2,5,5-d₄-pyrrolidinyl]-1-(3,4-dimethoxyphenethoxy)cyclohexane |
| 2 | | (1R,2R/1S,2S)-2-[(3R/3S)-Hydroxy-2,2,5,5-d₄-pyrrolidinyl]-1-(3,4-dimethoxyphen-2,2-d₂-ethoxy)cyclohexane |
| 3 | | (1R,2R/1S,2S)-2-[(3R/3S)-Hydroxy-2,2,5,5-d₄-pyrrolidinyl]-1-(3,4-dimethoxyphen-1,1,2,2-d₄-ethoxy)cyclohexane |
| 4 | | (1R,2R/1S,2S)-2-[(3R/3S)-Hydroxypyrrolidinyl]-1-(3,4-dimethoxyphen-1,1,2,2-d₄-ethoxy)cyclohexane |
| 5 | | (1R,2R/1S,2S)-2-[(3R/3S)-Hydroxy-2,2,5,5-d₄-pyrrolidinyl]-1-(3-methoxy-4-d₃-methoxyphenethoxy)cyclohexane |
| 6 | | (1R,2R/1S,2S)-2-[(3R/3S)-Hydroxy-2,2,5,5-d₄-pyrrolidinyl]-1-(3-methxoy-4-d₃-methoxyphen-1,1-d₂-ethoxy)cyclohexane |
| 7 | | (1R,2R/1S,2S)-2-[(3R/3S)-Hydroxy-2,2-d₂-pyrrolidinyl]-1-(3-methoxy-4-d₃-methoxyphen-1,1-d₂-ethoxy)cyclohexane |

-continued

| # | Compound | Chemical name |
|---|---|---|
| 8 | | (1R,2R/1S,2S)-2-[(3R/3S)-Hydroxy-5,5-d₂-pyrrolidinyl]-1-(3-methoxy-4-d₃-methoxyphen-1,1-d₂-ethoxy)cyclohexane |
| 9 | | (1R,2R/1S,2S)-2-[(3R/3S)-Hydroxypyrrolidinyl]-1-(3,4-di-d₃-methoxyphen-1,1-d₂-ethoxy)cyclohexane |
| 10 | | (1R,2R/1S,2S)-2-[(3R/3S)-Hydroxypyrrolidinyl]-1-(3,4-di-d₃-methoxyphenethoxy)cyclohexane |
| 11 | | (1R,2R/1S,2S)-2-[(3R/3S)-Hydroxy-2,2,5,5-d₄-pyrrolidinyl]-1-(3,4-di-d₃-methxoyphen-1,1-d₂-ethoxy)cyclohexane |
| 12 | | (1R,2R/1S,2S)-2-[(3R/3S)-Hydroxy-2,2,5,5-d₄-pyrrolidinyl]-1-(3,4-di-d₃-methxoyphenethoxy)cyclohexane |
| 13 | | (1R,2R/1S,2S)-2-[(3R/3S)-Hydroxypyrrolidinyl]-1-(3-methoxy-4-d₃-methoxyphen-2,2-d₂-ethoxy)cyclohexane |
| 14 | | (1R,2R/1S,2S)-2-[(3R/3S)-Hydroxy-2,2,5,5-d₄-pyrrolidinyl]-1-(3-methoxy-4-d₃-methoxyphen-2,2-d₂-ethoxy)cyclohexane |
| 15 | | (1R,2R/1S,2S)-2-[(3R/3S)-Hydroxypyrrolidinyl]-1-(3-d₃-methoxy-4-methoxyphen-1,1-d₂-ethoxy)cyclohexane |
| 16 | | (1R,2R/1S,2S)-2-[(3R/3S)-Hydroxy-2,2,5,5-d₄-pyrrolidinyl]-1-(3-d₃-methoxy-4-methoxyphen-1,1-d₂-ethoxy)cyclohexane |

-continued

| # | Compound | Chemical name |
|---|---|---|
| 17 | | (1R,2R/1S,2S)-2-[(3R/3S)-Hydroxypyrrolidinyl]-1-(3-d$_3$-methoxy-4-methoxyphenethoxy)cyclohexane |
| 18 | | (1R,2R/1S,2S)-2-[(3R/3S)-Hydroxypyrrolidinyl]-1-(3-methoxy-4-d$_3$-methoxyphenethoxy)cyclohexane |
| 19 | | (1R,2R/1S,2S)-2-[(3R/3S)-Hydroxy-2,2,5,5-d$_4$-pyrrolidinyl]-1-(3-d$_3$-methoxy-4-methoxyphenethoxy)cyclohexane |
| 20 | | (1R,2R/1S,2S)-2-[(3R/3S)-Hydroxy-3,4,4-d$_3$-pyrrolidinyl]-1-(3,4-dimethoxyphen-1,1-d$_2$-ethxoy)cyclohexane |
| 21 | | (1R,2R/1S,2S)-2-[(3R/3S)-Hydroxy-2,2,3,4,4,5,5-d$_7$-pyrrolidinyl]-1-(3,4-dimethoxyphen-1,1-d$_2$-ethoxy)cyclohexane |
| 22 | | (1R,2R/1S,2S)-2-[(3R/3S)-Hydroxy-3,4,4-d$_3$-pyrrolidinyl]-1-(3,4-dimethoxyphen-2,2-d$_2$-ethoxy)cyclohexane |
| 23 | | (1R,2R/1S,2S)-2-[(3R/3S)-Hydroxy-2,2,3,4,4,5,5-d$_7$-pyrrolidinyl]-1-(3,4-dimethoxyphen-2,2-d$_2$-ethoxy)cyclohexane |
| 24 | | (1R,2R/1S,2S)-2-[(3R/3S)-Hydroxy-3,4,4,-d$_3$-pyrrolidinyl]-1-(3-d$_3$-methoxy-4-methoxyphen-1,1,2,2-d$_4$-ethoxy)cyclohexane |

-continued

| # | Compound | Chemical name |
|---|---|---|
| 25 | | (1R,2R/1S,2S)-2-[(3R/3S)-Hydroxy-2,2,3,4,4,5,5-$d_7$-pyrrolidinyl]-1-(3-$d_3$-methoxy-4-methoxyphen-1,1,2,2-$d_4$-ethoxy)cyclohexane |
| 26 | | (1R,2R/1S,2S)-2-[(3R/3S)-Hydroxy-3,4,4-$d_3$-pyrrolidinyl]-1-(3-methxoy-4-$d_3$-methoxyphen-1,1,2,2-$d_4$-ethxoy)cyclohexane |
| 27 | | (1R,2R/1S,2S)-2-[(3R/3S)-Hydroxy-2,2,3,4,4,5,5-$d_7$-pyrrolidinyl]-1-(3-methoxy-4-$d_3$-methoxyphen-1,1,2,2-$d_4$-ethoxy)cyclohexane |
| 28 | | (1R,2R/1S,2S)-2-[(3R/3S)-Hydroxy-3,4,4-$d_3$-pyrrolidinyl]-1-(3-$d_3$-methoxy-4-methoxyphen-2,2-$d_2$-ethoxy)cyclohexane |
| 29 | | (1R,2R/1S,2S)-2-[(3R/3S)-Hydroxy-2,2,3,4,4,5,5-$d_7$-pyrrolidinyl]-1-(3-$d_3$-methoxy-4-methoxyphen-2,2-$d_2$-ethxoy)cyclohexane |
| 30 | | (1R,2R/1S,2S)-2-[(3R/3S)-Hydroxy-3,4,4-$d_3$-pyrrolidinyl]-1-(3-methoxy-4-$d_3$-methoxyphen-2,2-$d_2$-ethoxy)cyclohexane |
| 31 | | (1R,2R/1S,2S)-2-[(3R/3S)-Hydroxy-2,2,3,4,4,5,5-$d_7$-pyrrolidinyl]-1-(3-methoxy-4-$d_3$-methoxyphen-2,2-$d_2$-ethoxy)cyclohexane |

| # | Compound | Chemical name |
|---|---|---|
| 32 | | (1R,2R/1S,2S)-2-[(3R/3S)-Hydroxy-3,4,4-d$_3$-pyrrolidinyl]-1-(3-d$_3$-methoxy-4-methoxyphen-1,1-d$_2$-ethoxy)cyclohexane |
| 33 | | (1R,2R/1S,2S)-2-[(3R/3S)-Hydroxy-2,2,3,4,4,5,5-d$_7$-pyrrolidinyl]-1-(3-d$_3$-methoxy-4-methoxyphen-1,1-d$_2$-ethoxy)cyclohexane |
| 34 | | (1R,2R/1S,2S)-2-[(3R/3S)-Hydroxy-3,4,4-d$_3$-pyrrolidinyl]-1-(3-methoxy-4-d$_3$-methoxyphen-1,1-d$_2$-ethoxy)cyclohexane |
| 35 | | (1R,2R/1S,2S)-2-[(3R/3S)-Hydroxy-2,2,3,4,4,5,5-d$_7$-pyrrolidinyl]-1-(3-methoxy-4-d$_3$-methoxyphen-1,1-d$_2$-ethoxy)cyclohexane |
| 36 | | (1R,2R/1S,2S)-2-[(3R/3S)-Hydroxy-2,2,5,5-d$_4$-pyrrolidinyl]-1-(3-methoxy-4-hydroxyphenethoxy)cyclohexane |
| 37 | | (1R,2R/1S,2S)-2-[(3R/3S)-Hydroxy-2,2,5,5-d$_4$-pyrrolidinyl]-1-(3-methoxy-4-hydorxyphen-1,1-d$_2$-ethoxy)cyclohexane |
| 38 | | (1R,2R/1S,2S)-2-[(3R/3S)-Hydroxy-2,2,5,5-d$_4$-pyrrolidinyl]-1-(3-methoxy-4-hydroxyphen-2,2-d$_2$-ethoxy)cyclohexane |
| 39 | | (1R,2R/1S,2S)-2-[(3R/3S)-Hydroxypyrrolidinyl]-1-(3-methoxy-4-hydroxphen-1,1,2,2-d$_4$-ethoxy)cyclohexane |

| # | Compound | Chemical name |
|---|---|---|
| 40 | | (1R,2R/1S,2S)-2-[(3R/3S)-Hydroxy-2,2,5,5-$d_4$-pyrrolidinyl]-1-(3-methoxy-4-hydroxyphen-1,1,2,2-$d_4$-ethoxy)cyclohexane |
| 41 | | (1R,2R/1S,2S)-2-[(3R/3S)-Hydroxy-2,2,3,4,4,5,5-$d_7$-pyrrolidinyl]-1-(3-methoxy-4-hydroxyphenethoxy)cyclohexane |
| 42 | | (1R,2R/1S,2S)-2-[(3R/3S)-Hydroxy-2,2,3,4,4,5,5-$d_7$-pyrrolidinyl]-1-(3-methoxy-4-hydroxyphen-2,2-$d_2$-ethoxy)cyclohexane |
| 43 | | (1R,2R/1S,2S)-2-[(3R/3S)-Hydroxy-2,2,3,4,4,5,5-$d_7$-pyrrolidinyl]-1-(3-methoxy-4-hydroxyphen-1,1-$d_2$-ethoxy)cyclohexane |
| 44 | | (1R,2R/1S,2S)-2-[(3R/3S)-Hydroxy-3,4,4-$d_3$-pyrrolidinyl]-1-(3-methoxy-4-hydroxyphen-1,1,2,2-$d_4$-ethoxy)cyclohexane |
| 45 | | (1R,2R/1S,2S)-2-[(3R/3S)-Hydroxy-3,4,4,-$d_3$-pyrrolidinyl]-1-(3-methoxy-4-hydroxyphen-2,2-$d_2$-ethoxy)cyclohexane |
| 46 | | (1R,2R/1S,2S)-2-[(3R/3S)-Hydroxy-3,4,4-$d_3$-pyrrolidinyl]-1-(3-methoxy-4-hydroxyphen-1,1-$d_2$-ethoxy)cyclohexane |
| 47 | | (1R,2R/1S,2S)-2-[(3R/3S)-Hydroxy-3,4,4-$d_3$-pyrrolidinyl]-1-(3-methoxy-4-hydroxyphenethoxy)cyclohexane |

| # | Compound | Chemical name |
|---|---|---|
| 48 | | (1R,2R/1S,2S)-2-[(3R/3S)-Hydroxy-2,2,3,4,4,5,5-d$_7$-pyrrolidinyl]-1-(3-methoxy-4-hydroxyphen-1,1,2,2-d$_4$-ethoxy)cyclohexane |
| 49 | | (1R,2R/1S,2S)-2-[(3R/3S)-Hydroxy-2,2,5,5-d$_4$-pyrrolidinyl]-1-(3-hydroxy-4-methoxyphenethoxy)cyclohexane |
| 50 | | (1R,2R/1S,2S)-2-[(3R/3S)-Hydroxy-2,2,5,5-d$_4$-pyrrolidinyl]-1-(3-hydroxy-4-methoxyphen-1,1-d$_2$-ethoxy)cyclohexane |
| 51 | | (1R,2R/1S,2S)-2-[(3R/3S)-Hydroxy-2,2,5,5-d$_4$-pyrrolidinyl]-1-(3-hydroxy-4-methoxyphen-2,2-d$_2$-ethoxy)cyclohexane |
| 52 | | (1R,2R/1S,2S)-2-[(3R/3S)-Hydroxypyrrolidinyl]-1-(3-hydroxy-4-methoxyphen-1,1,2,2-d$_4$-ethoxy)cyclohexane |
| 53 | | (1R,2R/1S,2S)-2-[(3R/3S)-Hydroxy-2,2,5,5-d$_4$-pyrrolidinyl]-1-(3-hydroxy-4-methoxyphen-1,1,2,2-d$_4$-ethoxy)cyclohexane |
| 54 | | (1R,2R/1S,2S)-2-[(3R/3S)-Hydroxy-2,2,3,4,4,5,5-d$_7$-pyrrolidinyl]-1-(3-hydroxy-4-methoxyphenethoxy)cyclohexane |
| 55 | | (1R,2R/1S,2S)-2-[(3R/3S)-Hydroxy-2,2,3,4,4,5,5-d$_7$-pyrrolidinyl]-1-(3-hydroxy-4-methoxyphen-2,2-d$_2$-ethoxy)cyclohexane |

| # | Compound | Chemical name |
|---|---|---|
| 56 | | (1R,2R/1S,2S)-2-[(3R/3S)-Hydroxy-2,2,3,4,4,5,5-$d_7$-pyrrolidinyl]-1-(3-hydroxy-4-methoxyphen-1,1-$d_2$-ethoxy)cyclohexane |
| 57 | | (1R,2R/1S,2S)-2-[(3R/3S)-Hydroxy-2,2,3,4,4,5,5-$d_7$-pyrrolidinyl]-1-(3-hydroxy-4-methoxyphen-1,1,2,2-$d_4$-ethoxy)cyclohexane |
| 58 | | (1R,2R/1S,2S)-2-[(3R/3S)-Hydroxy-3,4,4-$d_3$-pyrrolidinyl]-1-(3-hydroxy-4-methoxyphen-1,1,2,2-$d_4$-ethoxy)cyclohexane |
| 59 | | (1R,2R/1S,2S)-2-[(3R/3S)-Hydroxy-3,4,4-$d_3$-pyrrolidinyl]-1-(3-hydroxy-4-methoxyphen-2,2-$d_2$-ethoxy)cyclohexane |
| 60 | | (1R,2R/1S,2S)-2-[(3R/3S)-Hydroxy-3,4,4-$d_3$-pyrrolidinyl]-1-(3-hydroxy-4-methoxyphen-1,1-$d_2$-ethoxy)cyclohexane |
| 61 | | (1R,2R/1S,2S)-2-[(3R/3S)-Hydroxy-3,4,4-$d_3$-pyrrolidinyl]-1-(3-hydroxy-4-methoxyphenethoxy)cyclohexane |
| 62 | | (1R,2R/1S,2S)-2-[(3R/3S)-Hydroxy-2,2,3,4,4,5,5-$d_7$-pyrrolidinyl]-1-(3-$d_3$-methoxy-4-hydroxyphen-1,1,2,2-$d_4$-ethoxy)cyclohexane |
| 63 | | (1R,2R/1S,2S)-2-[(3R/3S)-Hydroxy-2,2,3,4,4,5,5-$d_7$-pyrrolidinyl]-1-(3-hydroxy-4-$d_3$-methoxyphen-1,1,2,2-$d_4$-ethoxy)cyclohexane |

-continued

| # | Compound | Chemical name |
|---|---|---|
| 64 | | (1R,2R/1S,2S)-2-[(3R/3S)-Hydroxy-2,2,3,4,4,5,5-$d_7$-pyrrolidinyl]-1-(3,4-di-$d_3$-methoxyphen-1,1,2,2-$d_4$-ethoxy)cyclohexane |
| 65 | | (1R,2R)-2-[(3R)-Hydroxy-2,2,5,5-$d_4$-pyrrolidinyl]-1-(3,4-dimethoxyphen-2,2-$d_2$-ethoxy)cyclohexane |
| 66 | | (1R,2R)-2-[(3R)-Hydroxy-2,2,5,5-$d_4$-pyrrolidinyl]-1-(3,4-dimethoxyphen-1,1,2,2-$d_4$-ethoxy)cyclohexane |
| 67 | | (1R,2R)-2-[(3R)-Hydroxypyrrolidinyl]-1-(3,4-dimethoxyphen-1,1,2,2-$d_4$-ethoxy)cyclohexane |
| 68 | | (1R,2R)-2-[(3R)-Hydroxy-2,2,5,5-$d_4$-pyrrolidinyl]-1-(3-methoxy-4-$d_3$-methoxyphenethoxy)cyclohexane |
| 69 | | (1R,2R)-2-[(3R)-Hydroxy-2,2,5,5-$d_4$-pyrrolidinyl]-1-(3-methoxy-4-$d_3$-methoxyphen-1,1-$d_2$-ethoxy)cyclohexane |
| 70 | | (1R,2R)-2-[(3R)-Hydroxy-2,2-$d_2$-pyrrolidinyl]-1-(3-methoxy-4-$d_3$-methxoyphen-1,1-$d_2$-ethoxy)cyclohexane |
| 71 | | (1R,2R)-2-[(3R)-Hydroxy-5,5-$d_2$-pyrrolidinyl]-1-(3-methoxy-4-$d_3$-methoxyphen-1,1-$d_2$-ethoxy)cyclohexane |

-continued

| # | Compound | Chemical name |
|---|---|---|
| 72 | | (1R,2R)-2-[(3R)-Hydroxypyrrolidinyl]-1-(3,4-di-$d_3$-methoxyphen-1,1-$d_2$-ethoxy)cyclohexane |
| 73 | | (1R,2R)-2-[(3R)-Hydroxy-2,2,5,5-$d_4$-pyrrolidinyl]-1-(3,4-di-$d_3$-methoxyphen-1,1-$d_2$-ethoxy)cyclohexane |
| 74 | | (1R,2R)-2-[(3R)-Hydroxy-2,2,5,5-$d_4$-pyrrolidinyl]-1-(3,4-di-$d_3$-methoxyphenethoxy)cyclohexane |
| 75 | | (1R,2R)-2-[(3R)-Hydroxypyrrolidinyl]-1-(3-methoxy-4-$d_3$-methoxyphen-2,2-$d_2$-ethoxy)cyclohexane |
| 76 | | (1R,2R)-2-[(3R)-Hydroxy-2,2,5,5-$d_4$-pyrrolidinyl]-1-(3-methoxy-4-$d_3$-methoxyphen-2,2-$d_2$-ethoxy)cyclohexane |
| 77 | | (1R,2R)-2-[(3R)-Hydroxypyrrolidinyl]-1-(3-$d_3$-methxoy-4-methoxyphen-1,1-$d_2$-ethoxy)cyclohexane |
| 78 | | (1R,2R)-2-[(3R)-Hydroxy-2,2,5,5-$d_4$-pyrrolidinyl]-1-(3-$d_3$-methoxy-4-methoxyphen-1,1-$d_2$-ethoxy)cyclohexane |
| 79 | | (1R,2R)-2-[(3R)-Hydroxypyrrolidinyl]-1-(3-$d_3$-methoxy-4-methoxyphenethoxy)cyclohexane |
| 80 | | (1R,2R)-2-[(3R)-Hydroxy-2,2,5,5-$d_4$-pyrrolidinyl]-1-(3-$d_3$-methoxy-4-methoxyphenethoxy)cyclohexane |

-continued

| # | Compound | Chemical name |
|---|---|---|
| 81 | | (1R,2R)-2-[(3R)-Hydroxy-3,4,4-d₃-pyrrolidinyl]-1-(3,4-dimethoxyphen-1,1-d₂-ethoxy)cyclohexane |
| 82 | | (1R,2R)-2-[(3R)-Hydroxy-2,2,3,4,4,5,5-d₇-pyrrolidinyl]-1-(3,4-dimethoxyphen-1,1-d₂-ethoxy)cyclohexane |
| 83 | | (1R,2R)-2-[(3R)-Hydroxy-3,4,4-d₃-pyrrolidinyl]-1-(3,4-dimethoxyphen-2,2-d₂-ethxoy)cyclohexane |
| 84 | | (1R,2R)-2-[(3R)-Hydroxy-2,2,3,4,4,5,5-d₇-pyrrolidinyl]-1-(3,4-dimethoxyphen-2,2-d₂-ethoxy)cyclohexane |
| 85 | | (1R,2R)-2-[(3R)-Hydroxy-3,4,4-d₃-pyrrolidinyl]-1-(3-d₃-methoxy-4-methoxyphen-1,1,2,2-d₄-ethoxy)cyclohexane |
| 86 | | (1R,2R)-2-[(3R)-Hydroxy-2,2,3,4,4,5,5-d₇-pyrrolidinyl]-1-(3-d₃-methoxy-4-methoxyphen-1,1,2,2-d₄-ethoxy)cyclohexane |
| 87 | | (1R,2R)-2-[(3R)-Hydroxy-3,4,4-d₃-pyrrolidinyl]-1-(3-methoxy-4-d₃-methoxyphen-1,1,2,2-d₄-ethoxy)cyclohexane |

| # | Compound | Chemical name |
|---|---|---|
| 88 | | (1R,2R)-2-[(3R)-Hydroxy-2,2,3,4,4,5,5-d₇-pyrrolidinyl]-1-(3-methoxy-4-d₃-methoxyphen-1,1,2,2-d₄-ethoxy)cyclohexane |
| 89 | | (1R,2R)-2-[(3R)-Hydroxy-3,4,4-d₃-pyrrolidinyl]-1-(3-d₃-methxoy-4-methoxyphen-2,2-d₂-ethoxy)cyclohexane |
| 90 | | (1R,2R)-2-[(3R)-Hydroxy-2,2,3,4,4,5,5-d₇-pyrrolidinyl]-1-(3-d₃-methoxy-4-methoxyphen-2,2-d₂-ethoxy)cyclohexane |
| 91 | | (1R,2R)-2-[(3R)-Hydroxy-3,4,4-d₃-pyrrolidinyl]-1-(3-methoxy-4-d₃-methoxyphen-2,2-d₂-ethoxy)cyclohexane |
| 92 | | (1R,2R)-2-[(3R)-Hydroxy-2,2,3,4,4,5,5-d₇-pyrrolidinyl]-1-(3-methoxy-4-d₃-methoxyphen-2,2-d₂-ethoxy)cyclohexane |
| 93 | | (1R,2R)-2-[(3R)-Hydroxy-3,4,4-d₃-pyrrolidinyl]-1-(3-d₃-methoxy-4-methoxyphen-1,1-d₂-ethoxy)cyclohexane |
| 94 | | (1R,2R)-2-[(3R)-Hydroxy-2,2,3,4,4,5,5-d₇-pyrrolidinyl]-1-(3-d₃-methoxy-4-methoxyphen-1,1-d₂-ethoxy)cyclohexane |
| 95 | | (1R,2R)-2-[(3R)-Hydroxy-3,4,4-d₃-pyrrolidinyl]-1-(3-methoxy-4-d₃-methoxyphen-1,1-d₂-ethoxy)cyclohexane |

| # | Compound | Chemical name |
|---|---|---|
| 96 | | (1R,2R)-2-[(3R)-Hydroxy-2,2,3,4,4,5,5-d₇-pyrrolidinyl]-1-(3-methoxy-4-d₃-methoxyphen-1,1-d₂-ethoxy)cyclohexane |
| 97 | | (1R,2R)-2-[(3R)-Hydroxy-2,2,5,5-d₄-pyrrolidinyl]-1-(3-methoxy-4-hydroxyphen-1,1-d₂-ethoxy)cyclohexane |
| 98 | | (1R,2R)-2-[(3R)-Hydroxy-2,2,5,5-d₄-pyrrolidinyl]-1-(3-methoxy-4-hydroxyphen-2,2-d₂-ethoxy)cyclohexane |
| 99 | | (1R,2R)-2-[(3R0-Hydroxypyrrolidinyl]-1-(3-methoxy-4-hydroxyphen-1,1,2,2-d₄-ethoxy)cyclohexane |
| 100 | | (1R,2R)-2-[(3R)-Hydroxy-2,2,5,5-d₄-pyrrolidinyl]-1-(3-methoxy-4-hydroxyphen-1,1,2,2-d₄-ethoxy)cyclohexane |
| 101 | | (1R,2R)-2-[(3R)-Hydroxy-2,2,3,4,4,5,5-d₇-pyrrolidinyl]-1-(3-methoxy-4-hydroxyphenethoxy)cyclohexane |
| 102 | | (1R,2R)-2-[(3R)-Hydroxy-2,2,3,4,4,5,5-d₇-pyrrolidinyl]-1-(3-methoxy-4-hydroxphen-2,2-d₂-ethoxy)cyclohexane |
| 103 | | (1R,2R)-2-[(3R)-Hydroxy-2,2,3,4,4,5,5-d₇-pyrrolidinyl]-1-(3-methoxy-4-hydroxyphen-1,1,-d₂-ethoxy)cyclohexane |

-continued

| # | Compound | Chemical name |
|---|---|---|
| 104 | | (1R,2R)-2-[(3R)-Hydroxy-3,4,4-d$_3$-pyrrolidinyl]-1-(3-methoxy-4-hydroxyphen-1,1,2,2-d$_4$-ethoxy)cyclohexane |
| 105 | | (1R,2R)-2-[(3R)-Hydroxy-3,4,4-d$_3$-pyrrolidinyl]-1-(3-methoxy-4-hydroxyphen-2,2-d$_2$-ethoxy)cyclohexane |
| 106 | | (1R,2R)-2-[(3R)-Hydroxy-3,4,4-d$_3$-pyrrolidinyl]-1-(3-methoxy-4-hydroxyphen-1,1-d$_2$-ethoxy)cyclohexane |
| 107 | | (1R,2R)-2-[(3R)-Hydroxy-3,4,4-d$_3$-pyrrolidinyl]-1-(3-methoxy-4-hydroxyphenethoxy)cyclohexane |
| 108 | | (1R,2R)-2-[(3R)-Hydroxy-2,2,3,4,4,5,5-d$_7$-pyrrolidinyl]-1-(3-methoxy-4-hydroxyphen-1,1,2,2-d$_4$-ethoxy)cyclohexane |
| 109 | | (1R,2R)-2-[(3R)-Hydroxy-2,2,5,5-d$_4$-pyrrolidinyl]-1-(3-hydroxy-4-methoxyphenethoxy)cyclohexane |
| 110 | | (1R,2R)-2-[(3R)-Hydroxy-2,2,5,5-d$_4$-pyrrolidinyl]-1-(3-hydroxy-4-methoxyphen-1,1-d$_2$-ethoxy)cyclohexane |
| 111 | | (1R,2R)-2-[(3R)-Hydroxy-2,2,5,5-d$_4$-pyrrolidinyl]-1-(3-hydroxy-4-methoxyphen-2,2-d$_2$-ethoxy)cyclohexane |

-continued

| # | Compound | Chemical name |
|---|---|---|
| 112 | | (1R,2R)-2-[(3R)-Hydroxypyrrolidinyl]-1-(3-hydroxy-4-methoxyphen-1,1,2,2-$d_4$-ethoxy)cyclohexane |
| 113 | | (1R,2R)-2-[(3R)-Hydroxy-2,2,5,5-$d_4$-pyrrolidinyl]-1-(3-hydroxy-4-methoxyphen-1,1,2,2-$d_4$-ethoxy)cyclohexane |
| 114 | | (1R,2R)-2-[(3R)-Hydroxy-2,2,3,4,4,5,5-$d_7$-pyrrolidinyl]-1-(3-hydroxy-4-methoxyphenethoxy)cyclohexane |
| 115 | | (1R,2R)-2-[(3R)-Hydroxy-2,2,3,4,4,5,5-$d_7$-pyrrolidinyl]-1-(3-hydroxy-4-methoxyphen-2,2-$d_2$-ethoxy)cyclohexane |
| 116 | | (1R,2R)-2-[(3R)-Hydroxy-2,2,3,4,4,5,5-$d_7$-pyrrolidinyl]-1-(3-hydroxy-4-methoxyphen-1,1-$d_2$-ethoxy)cyclohexane |
| 117 | | (1R,2R)-2-[(3R)-Hydroxy-2,2,3,4,4,5,5,-$d_7$-pyrrolidinyl]-1-(3-hydroxy-4-methoxyphen-1,1,2,2-$d_4$-ethoxy)cyclohexane |
| 118 | | (1R,2R)-2-[(3R)-Hydroxy-3,4,4,-$d_3$-pyrrolidinyl]-1-(3-hydroxy-4-methoxyphen-1,1,2,2-$d_4$-ethoxy)cyclohexane |
| 119 | | (1R,2R)-2-[(3R)-Hydroxy-3,4,4-$d_3$-pyrrolidinyl]-1-(3-hydroxy-4-methoxyphen-2,2-$d_2$-ethoxy)cyclohexane |

-continued

| # | Compound | Chemical name |
|---|---|---|
| 120 | [structure] | (1R,2R)-2-[(3R)-Hydroxy-3,4,4-$d_3$-pyrrolidinyl]-1-(3-hydroxy-4-methoxyphen-1,1-$d_2$-ethoxy)cyclohexane |
| 121 | [structure] | (1R,2R)-2-[(3R)-Hydroxy-3,4,4-$d_3$-pyrrolidinyl]-1-(3-hydroxy-4-methoxyphenethoxy)cyclohexane |
| 122 | [structure] | (1R,2R)-2-[(3R)-Hydroxy-2,2,3,4,4,5,5-$d_7$-pyrrolidinyl]-1-(3-$d_3$-methoxy-4-hydroxyphen-1,1,2,2-$d_4$-ethoxy)cyclohexane |
| 123 | [structure] | (1R,2R)-2-[(3R)-Hydroxy-2,2,3,4,4,5,5-$d_7$-pyrrolidinyl]-1-(3-hydroxy-4-$d_3$-methoxyphen-1,1,2,2-$d_4$-ethoxy)cyclohexane |
| 124 | [structure] | (1R,2R)-2-[(3R)-Hydroxy-2,2,3,4,4,5,5-$d_7$-pyrrolidinyl]-1-(3,4-di-$d_3$-methoxyphen-1,1,2,2-$d_4$-ethoxy)cyclohexane |

BIOLOGICAL EXAMPLE 1

Determining the Concentration of a Compound of Formula (1) or a Compound of Formula (2) in a Biological Matrix The following describes an assay wherein compounds of the invention were used to determine the concentration of a compound of formula (1) in a biological matrix. The same assay may be used to determine the concentration of a compound of formula (2) in a biological matrix.

Stock solutions of 3-pyrrolidinol, 1-[(1R,2R)-2-[2-(3,4-dimethoxyphenyl)ethoxy]-cyclohexyl]-, hydrochloride, 3(R) (hereinafter "R-StS") and 3-pyrrolidinol, 1-[(1R,2R)-2-[2-(3,4-dimethoxyphenyl)ethoxy]cyclohexyl]-, hydrochloride, 3(S) (hereinafter "S-StS") (compounds of formula (1)) were prepared separately in water at 1 mg/mL for preparation of standard curve and QC samples. The concentrations of the stock solutions were corrected for chemical potency and molecular weight of the free base. Aliquots of each stock solution were mixed together to prepare a working solution (WS1) containing 60 μg/mL each of R-StS and S-StS. An internal standard solution (IS) containing (1R,2R)-2-[(3R)-hydroxy-2,2,5,5-$d_4$-pyrrolidinyl]-1-(3,4-dimethoxyphenethoxy)cyclohexane hydrochloride and (1R,2R)-2-[(3R)-hydroxy-2,2,5,5-$d_4$-pyrrolidinyl]-1-(3-methoxy-4-hydroxyphenethoxy)cyclohexane hydrochloride was prepared at 0.5 μg/mL in water.

A series of standard spiking solutions (SpS) were prepared according to Table 1.

TABLE 1

| SpS | Core Solution Used | Volume of Core Solution Used (μL) | Volume of Water (μL) | Total Volume (μL) | Concentration of R-StS (ng/mL) | Concentration of S-StS (ng/mL) |
|---|---|---|---|---|---|---|
| SpS1 | ws1 | 200 | 3800 | 4000 | 2999 | 3001 |
| SpS2 | ws1 | 150 | 3850 | 4000 | 2249 | 2251 |
| SpS3 | ws1 | 90 | 3910 | 4000 | 1350 | 1350 |
| SpS4 | ws1 | 60 | 3940 | 4000 | 900 | 900 |
| SpS5 | SpS1 | 600 | 3400 | 4000 | 450 | 450 |
| SpS6 | SpS1 | 240 | 3760 | 4000 | 180 | 180 |
| SpS7 | SpS1 | 120 | 3880 | 4000 | 90.0 | 90.0 |
| SpS8 | SpS1 | 60 | 3940 | 4000 | 45.0 | 45.0 |
| SpS9 | SpS6 | 667 | 3333 | 4000 | 30.0 | 30.0 |
| SpS10 | SpS6 | 333 | 3667 | 4000 | 15.0 | 15.0 |

TABLE 1-continued

| SpS | Core Solution Used | Volume of Core Solution Used (μL) | Volume of Water (μL) | Total Volume (μL) | Concentration of R-StS (ng/mL) | Concentration of S-StS (ng/mL) |
|---|---|---|---|---|---|---|
| SpS11 | SpS6 | 111 | 3889 | 4000 | 4.99 | 5.00 |
| SpS12 | SpS6 | 56 | 3944 | 4000 | 2.52 | 2.52 |

The standard spiking solutions (SpS) were then spiked into blank rat plasma together with internal standard solution (1S) to obtain standard calibrators (STD) according to Table 2.

TABLE 2

| STD | Standard Spiking Solution | Blank Plasma Volume (μL) | SpS Volume (μL) | IS Volume (μL) | Final Concentration in Rat Plasma (ng/mL of plasma) | |
|---|---|---|---|---|---|---|
| | | | | | R-StS | S-StS |
| STD1 | SpS1 | 20 | 40 | 50 | 5998 | 6002 |
| STD2 | SpS2 | 20 | 40 | 50 | 4499 | 4501 |
| STD3 | SpS3 | 20 | 40 | 50 | 2699 | 2701 |
| STD4 | SpS4 | 20 | 40 | 50 | 1800 | 1800 |
| STD5 | SpS5 | 20 | 40 | 50 | 900 | 900 |
| STD6 | SpS6 | 20 | 40 | 50 | 360 | 360 |
| STD7 | SpS7 | 20 | 40 | 50 | 180 | 180 |
| STD8 | SpS8 | 20 | 40 | 50 | 90.0 | 90.0 |
| STD9 | SpS9 | 20 | 40 | 50 | 60.0 | 60.0 |
| STD10 | SpS10 | 20 | 40 | 50 | 30.0 | 30.0 |
| STD11 | SpS11 | 20 | 40 | 50 | 9.99 | 9.99 |
| STD12 | SpS12 | 20 | 40 | 50 | 5.04 | 5.04 |

Quality control spiking solutions (QCS) were prepared according to Table 3.

TABLE 3

| QCS | Core Solution Used | Volume of Core solution (μL) | Volume of Water (μL) | Total Volume (μL) | Concentration of R-StS (ng/mL) | Concentration of S-StS (n/mL) |
|---|---|---|---|---|---|---|
| QCS1 | ws1 | 200 | 3800 | 4000 | 2999 | 3001 |
| QCS2 | ws1 | 150 | 3850 | 4000 | 2249 | 2251 |
| QCS4 | ws1 | 60 | 3940 | 4000 | 900 | 900 |
| QCS6 | QCS1 | 240 | 3760 | 4000 | 180 | 180 |
| QCS10 | QCS6 | 333 | 3667 | 4000 | 15.0 | 15.0 |

The QC spiking solutions were then spiked into blank rat plasma together with internal standard to obtain QC samples according to Table 4. QC samples were prepared in six replicates for each level.

TABLE 4

| QC | Standard Spiking Solution | Blank Plasma Volume (μL) | Volume of QCS (μL) | IS Volume (μL) | Final concentration in Rat Plasma (ng/mL of plasma) | |
|---|---|---|---|---|---|---|
| | | | | | R-StS | S-StS |
| H | QCS2 | 20 | 40 | 50 | 4499 | 4501 |
| M | QCS4 | 20 | 40 | 50 | 1800 | 1800 |
| L | QCS6 | 20 | 40 | 50 | 360 | 360 |
| LL | QCS10 | 20 | 40 | 50 | 30.0 | 30.0 |

Extraction Procedure

Thaw blank plasma at room temperature. Transfer 20 μL of blank plasma to 1 mL 96-deep well plate. Add 40 μL of spiking standard solution or spiking QC solution (or water for a test sample). Add 50 μL of internal standard solution. Lower pH to approximately 2.0 by adding 50 μL of 2% phosphoric acid and vortex sample mixture. Add 200 μL of methanol to a microelution plate (comprising a mixture cation exchange/reversse phase coloumn) and apply vacuum. Add 200 μL of water to the microelution plate and apply vacuum. Transfer samples to the microelution plate and apply vacuum. Add 200 μL of 2% formic acid to the microelution plate and apply vacuum. Add 200 μL of methanol to a microelution plate and apply vacuum. Replace waste plate with 350 μL 96-deep well collection plate. Add 100 μL of 40/60 (v/v) acetonitrile/isopropanol in 5% ammonium hydroxide and apply vacuum. Evaporate samples under $N_2$ stream to dryness (10 mins). Add 50 μL of mobile phase to reconstitute eluted sample for analysis. Vortex and sonicate reconstituted sample for 1 min. Seal plate with plastic mat and inject samples.

The LC/MS/MS conditions used to determine the concentration of the compounds of formula (1) in the samples are set out in Table 5:

TABLE 5

| Column temperature | 26° C. |
|---|---|
| Sample temperature | 10° C. |
| Mobile phase | Isocratic, 13:87 (v/v) of 0.1% formic acid in methanol to 0.1% formic acid in water |
| Flowrate | 0.35 mL/min |
| Injection volume | 10 μL |
| Runtime | 18 min |
| MS/MS acquisition | ESI, +ve MRM mode |

The above assay demonstrated that the use of the compounds of the invention as internal standards was effective in determining the concentration of compounds of formula (1) in a biological matrix, such as plasma.

BIOLOGICAL EXAMPLE 2

Assessment of Antiarrhythmic Efficacy

Antiarrhythmic efficacy may be assessed by investigating the effect of a compound of the invention on the incidence of cardiac arrhythmias in anesthetized rats subjected to coronary artery occlusion. Rats weighing 200-300 g are subjected to preparative surgery and assigned to groups in a random block design. In each case, the animal is anesthetized with pentobarbital during surgical preparation. The left carotid artery is cannulated for measurement of mean arterial blood pressure and withdrawal of blood samples. The left jugular vein is also cannulated for injection of drugs. The thoracic cavity is opened and a polyethylene occluder loosely placed around the left anterior descending coronary artery. The thoracic cavity is then closed.

An ECG is recorded by insertion of electrodes placed along the anatomical axis of the heart. In a random and double-blind manner, an infusion of vehicle or the compound to be tested is given about 15 min post-surgery. After 5 minutes infusion, the occluder is pulled so as to produce a coronary artery occlusion. ECG, arrhythmias, blood pressure, heart rate and mortality are monitored for 15 minutes after occlusion. Arrhythmias are recorded as ventricular tachycardia (VT) and ventricular fibrillation (VF) and scored according to Curtis, M. J. and Walker, M. J. A., *Cardiovasc. Res.* 22:656 (1988).

Rats are excluded from the study if they did not exhibit pre-occlusion serum potassium concentrations within the range of 2.9-3.9 mM. Occlusion is associated with increases in R-wave height and "S-T" segment elevation; and an occluded zone (measured after death by cardiogreen dye perfusion) in the range of 25%-50% of total left-ventricular weight.

Results of the test compounds may be expressed as values of a given infusion rate in micromol/kg/min. ($ED_{50}AA$) which will reduce the arrhythmia score in treated animals to 50% of that shown by animals treated only with the vehicle in which the test compound(s) is dissolved.

BIOLOGICAL EXAMPLE 3

Measurement of Cardiovascular and Behavioral Effects

Preparative surgery is performed in Sprague Dawley rats weighing 200-300 g and anaesthetized with 65 mg/kg (i.p.) pentobarbital. The femoral artery and vein are cannulated using polyethylene (PE)-10 tubing. Prior to surgery, this PE-10 tubing had been annealed to a wider gauge (PE-50) tubing for externalization. The cannulated PE-10/PE-50 tubing is passed through a trocar and exteriorised together with three (lead II) limb ECG leads (see below). The trocar is threaded under the skin of the back and out through a small incision at the mid-scapular region. A ground ECG electrode is inserted subcutaneously using a 20 gauge needle with the lead wire threaded through it. To place the other ECG electrodes, a small incision is made in the anterior chest region over the heart and ECG leads are inserted into the subcutaneous muscle layer in the region of the heart using a 20 gauge needle. Other ECG leads are inserted into the subcutaneous muscle layer in the region near the base of the neck and shoulder (right side). The animal is returned to a clean recovery-cage with free access to food and water. The treatment and observational period for each animal commenced after a 24-hour recovery period.

A 15 min observational period is recorded followed by the intravenous infusion regime of the test compound at an initial dose of 2.0 µmol/kg/min (at 1 mL/hr). This rate is doubled every 5 minutes until one of the following effects is observed:
 a) partial or complete convulsions
 b) severe arrhythmias
 c) bradycardia below 120 beats/min
 d) hypotension below 50 mmHg
 e) the dose exceeds 32 times the initial starting dose (i.e. 64 µmol/kg/min).

Blood pressure (BP), heart rate (HR) and ECG variables are continuously recorded while behavioral responses are also monitored and the total accumulative drug dose and drug infusion rate at which the response (such as convulsion, piloerection, ataxia, restlessness, compulsive chewing, lip-smacking, wet dog shake etc.) occurred are recorded.

Estimates of plasma concentrations of the test compound are determined by removing a 0.5 mL blood sample at the end of the experiment. Blood samples are centrifuged for 5 min at 4600×g and the plasma decanted. Brain tissue samples are also extracted and kept frozen (−20° C.) along with the plasma samples for chemical analysis.

Electrocardiograph (ECG) parameters: PR, QRS, $QT_1$ (peak of T-wave), $QT_2$ (midpoint of T-wave deflection) and hemodynamic parameters: BP and HR are analyzed using the automated analysis function in LabView (National Instruments) with a customized autoanalysis software (Nortran Pharmaceuticals). The infused dose producing 25% from control ($D_{25}$) for all recorded ECG variables is determined.

Results of the tests can be expressed as $D_{25}$ (micromol/kg) which are the doses required to produce a 25% increase in the ECG parameter measured. The increases in P-R interval and QRS interval indicate cardiac sodium channel blockade while the increase in Q-T interval indicates cardiac potassium channel blockade.

BIOLOGICAL EXAMPLE 4

Electrophysiological Test (In Vivo)

Male Sprague-Dawley rats weighing between 250-350 g are used. They are randomly selected from a single group and anesthetized with pentobarbital (65 mg/kg, ip.) with additional anesthetic given if necessary.

The trachea is cannulated and the rat is artificially ventilated at a stroke volume of 10 mL/kg, 60 strokes/minute. The right external jugular vein and the left carotid artery are cannulated for intravenous injections of compounds and blood pressure (BP) recording, respectively.

Needle electrodes are subcutaneously inserted along the suspected anatomical axis (right atrium to apex) of the heart for ECG measurement. The superior electrode is placed at the level of the right clavicle about 0.5 cm from the midline, while the inferior electrode is placed on the left side of the thorax, 0.5 cm from the midline and at the level of the ninth rib.

Two Teflon-coated silver electrodes are inserted through the chest wall using 27 G needles as guides and implanted in the epicardium of left ventricle (4-5 mm apart). Square pulse stimulation is provided by a stimulator controlled by a computer. In-house programmed software is used to determine the following: threshold current (iT) for induction of extra systoles, maximum following frequency (MFF), effective refractory period (ERP) and ventricular flutter threshold (VTt). Briefly, iT is measured as the minimal current (in µA) of a square wave stimulus required to capture and pace the heart at a frequency of 7.5 Hz and a pulse width of 0.5 msec; ERP is the minimum delay (in msec) for a second stimulus required to cause an extra systole with the heart entrained at a frequency of 7.5 Hz (1.5×iT and 0.2 msec pulse width), MFF is the maximum stimulation frequency (in Hz) at which the heart is unable to follow stimulation (1.5×iT and 0.2 msec pulse width); VTt is the minimum pulse current (in µA) to evoke a sustained episode of VT (0.2 msec pulse width and 50 Hz) (Howard, P. G. and Walker, M. J. A., *Proc. West. Pharmacol. Soc.* 33:123-127 (1990)).

Blood pressure (BP) and electrocardiographic (ECG) parameters are recorded and analyzed using LabView (National Instruments) with a customized autoanalysis software (Nortran Pharmaceuticals Inc.) to calculate mean BP (mmHg, ⅔ diastolic+⅓ systolic blood pressure), HR (bpm, 60/R—R interval); PR (msec, the interval from the beginning of the P-wave to the peak of the R-wave), QRS (msec, the interval from the beginning of the R-wave due to lack of Q wave in rat ECG, to the peak of the S-wave), QT (msec, the interval from the beginning of the R-wave to the peak of the T-wave).

The initial infusion dose is chosen based on a previous toxicology study of the test compound in conscious rats. This is an infusion dose that did not produce a 10% change from pre-drug levels in haemodynamic or ECG parameters.

The animal is left to stabilize prior to the infusion treatment according to a predetermined random and blind table. The initial infusion treatment is started at a rate of 0.5 mL/hr/300 g (i.e., 0.5 µmol/kg/min). Each infusion dose is doubled (in rate) every 5 minutes. All experiments are terminated at 32 mL/hr/300 g (i.e., 32 µmol/kg/min). Electrical stimulation protocols are initiated during the last two minutes of each infusion level.

Responses to test compounds are calculated as percent changes from pre-infusion values; this normalization is used

What is claimed is:

1. A method of treating arrhythmia in a human, wherein the method comprises administering to the human in need thereof a therapeutically effective amount of a compound of formula (I):

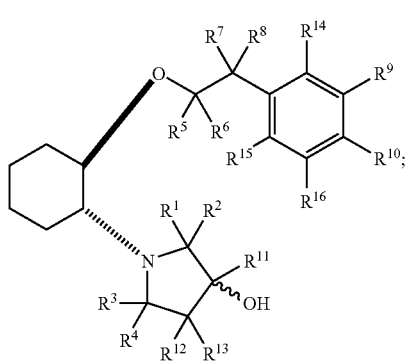

wherein:
$R^1$, $R^2$, $R^3$, $R^4$, $R^5$, $R^6$, $R^7$, $R^8$, $R^{11}$, $R^{12}$, $R^{13}$, $R^{14}$, $R^{15}$ and $R^{16}$ are each independently hydrogen or deuterium; and
$R^9$ and $R^{10}$ are each independently hydroxy, methoxy or —$OCD_3$;
where at least one of $R^1$, $R^2$, $R^3$, $R^4$, $R^5$, $R^6$, $R^7$, $R^8$, $R^{11}$, $R^{12}$, $R^{13}$, $R^{14}$, $R^{15}$ and $R^{16}$ is deuterium or at least one of $R^9$ and $R^{10}$ is —$OCD_3$;
or an isolated stereoisomer thereof;
or a pharmaceutically acceptable salt thereof;
wherein the deuterium present in the compound is present at greater than the natural abundance of deuterium.

2. The method of claim 1 wherein:
$R^1$ and $R^2$ are both hydrogen or are both deuterium;
$R^3$ and $R^4$ are both hydrogen or are both deuterium;
$R^5$ and $R^6$ are both hydrogen or are both deuterium;
$R^7$ and $R^8$ are both hydrogen or are both deuterium;
$R^9$ and $R^{10}$ are each independently hydroxy, methoxy or —$OCD_3$;
$R^{11}$ is hydrogen or deuterium;
$R^{12}$ and $R^{13}$ are both hydrogen or are both deuterium; and
$R^{14}$, $R^{15}$, and $R^{16}$ are all hydrogen or all deuterium.

3. The method of claim 1 wherein:
$R^1$ and $R^2$ are both hydrogen or are both deuterium;
$R^3$ and $R^4$ are both hydrogen or are both deuterium;
$R^5$ and $R^6$ are both deuterium;
$R^7$ and $R^8$ are both hydrogen or are both deuterium;
$R^9$ and $R^{10}$ are each independently hydroxy, methoxy or —$OCD_3$;
$R^{11}$ is hydrogen or deuterium;
$R^{12}$ and $R^{13}$ are both hydrogen or are both deuterium; and
$R^{14}$, $R^{15}$, and $R^{16}$ are all hydrogen or all deuterium.

4. The method of claim 1 wherein:
$R^1$ and $R^2$ are both hydrogen or are both deuterium;
$R^3$ and $R^4$ are both hydrogen or are both deuterium;
$R^5$ and $R^6$ are both hydrogen or are both deuterium;
$R^7$ and $R^8$ are both deuterium;
$R^9$ and $R^{10}$ are each independently hydroxy, methoxy or —$OCD_3$;
$R^{11}$ is hydrogen or deuterium;
$R^{12}$ and $R^{13}$ are both hydrogen or are both deuterium; and
$R^{14}$, $R^{15}$, and $R^{16}$ are all hydrogen or all deuterium.

5. The method of claim 1 wherein:
$R^1$ and $R^2$ are both deuterium;
$R^3$ and $R^4$ are both deuterium;
$R^5$ and $R^6$ are both hydrogen or are both deuterium;
$R^7$ and $R^8$ are both hydrogen or are both deuterium;
$R^9$ and $R^{10}$ are each independently hydroxy, methoxy or —$OCD_3$;
$R^{11}$ is hydrogen or deuterium;
$R^{12}$ and $R^{13}$ are both hydrogen or are both deuterium; and
$R^{14}$, $R^{15}$, and $R^{16}$ are all hydrogen or all deuterium.

6. The method of claim 1 wherein:
$R^1$ and $R^2$ are both hydrogen or are both deuterium;
$R^3$ and $R^4$ are both hydrogen or are both deuterium;
$R^5$ and $R^6$ are both hydrogen or are both deuterium;
$R^7$ and $R^8$ are both hydrogen or are both deuterium;
$R^9$ is —$OCD_3$;
$R^{10}$ is hydroxy, methoxy or —$OCD_3$;
$R^{11}$ is hydrogen or deuterium;
$R^{12}$ and $R^{13}$ are both hydrogen or are both deuterium; and
$R^{14}$, $R^{15}$, and $R^{16}$ are all hydrogen or all deuterium.

7. The method of claim 1 wherein:
$R^1$ and $R^2$ are both hydrogen or are both deuterium;
$R^3$ and $R^4$ are both hydrogen or are both deuterium;
$R^5$ and $R^6$ are both hydrogen or are both deuterium;
$R^7$ and $R^8$ are both hydrogen or are both deuterium;
$R^9$ is hydroxy, methoxy or —$OCD_3$;
$R^{10}$ is —$OCD_3$;
$R^{11}$ is hydrogen or deuterium;
$R^{12}$ and $R^{13}$ are both hydrogen or are both deuterium; and
$R^{14}$, $R^{15}$, and $R^{16}$ are all hydrogen or all deuterium.

8. The method of claim 1 wherein:
$R^1$ and $R^2$ are both hydrogen or are both deuterium;
$R^3$ and $R^4$ are both hydrogen or are both deuterium;
$R^5$ and $R^6$ are both hydrogen or are both deuterium;
$R^7$ and $R^8$ are both hydrogen or are both deuterium;
$R^9$ and $R^{10}$ are each independently hydroxy, methoxy or —$OCD_3$;
$R^{11}$ is deuterium;
$R^{12}$ and $R^{13}$ are both hydrogen or are both deuterium; and
$R^{14}$, $R^{15}$, and $R^{16}$ are all hydrogen or all deuterium.

9. The method of claim 1 wherein:
$R^1$ and $R^2$ are both hydrogen or are both deuterium;
$R^3$ and $R^4$ are both hydrogen or are both deuterium;
$R^5$ and $R^6$ are both hydrogen or are both deuterium;
$R^7$ and $R^8$ are both hydrogen or are both deuterium;
$R^9$ and $R^{10}$ are each independently hydroxy, methoxy or —$OCD_3$;
$R^{11}$ is hydrogen or deuterium;
$R^{12}$ and $R^{13}$ are both deuterium; and
$R^{14}$, $R^{15}$, and $R^{16}$ are all hydrogen or all deuterium.

10. A method of treating arrhythmia in a human, wherein the method comprises administering to the human in need thereof a therapeutically effective amount of a compound of formula (II):

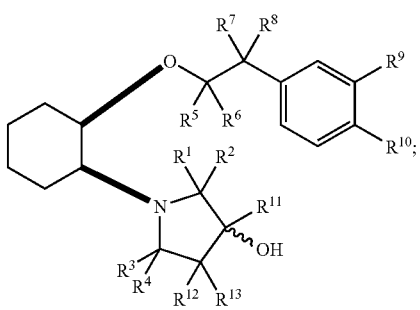

wherein
  $R^1$, $R^2$, $R^3$, $R^4$, $R^5$, $R^6$, $R^7$, $R^8$, $R^{11}$, $R^{12}$ and $R^{13}$ are each independently hydrogen or deuterium; and
  $R^9$ and $R^{10}$ are each independently hydroxy, methoxy or —$OCD_3$;
  where at least one of $R^1$, $R^2$, $R^3$, $R^4$, $R^5$, $R^6$, $R^7$, $R^8$, $R^{11}$, $R^{12}$, $R^{13}$, $R^{14}$, $R^{15}$ and $R^{16}$ is deuterium or at least one of $R^9$ and $R^{10}$ is —$OCD_3$;
  or an isolated stereoisomer thereof;
  or a pharmaceutically acceptable salt thereof;
  wherein the deuterium present in the compound is present at greater than the natural abundance of deuterium.

* * * * *